US012806416B2

(12) United States Patent
Ralston et al.

(10) Patent No.: US 12,806,416 B2
(45) **Date of Patent: *Nov. 24, 2026**

(54) DETECTING AND TREATING NEUROPHYSIOLOGICAL IMPAIRMENT

(71) Applicant: Neursantys, Inc., Menlo Park, CA (US)

(72) Inventors: John D. Ralston, Portola Valley, CA (US); Ryan M. Peters, Calgary (CA); Jordan A. King, Calgary (CA); Osman Darici, Calgary (CA)

(73) Assignee: Neursantys, Inc., Portola Valley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/368,983

(22) Filed: Oct. 24, 2025

(65) Prior Publication Data

US 2026/0115465 A1 Apr. 30, 2026

Related U.S. Application Data

(63) Continuation-in-part of application No. 17/671,176, filed on Feb. 14, 2022, now Pat. No. 12,599,316.

(Continued)

(51) Int. Cl.
*A61N 1/36* (2006.01)

(52) U.S. Cl.
CPC ..... *A61N 1/36025* (2013.01); *A61N 1/36031* (2017.08); *A61N 1/36034* (2017.08); *A61N 1/36036* (2017.08)

(58) Field of Classification Search
CPC ............ A61N 1/36025; A61N 1/36031; A61N 1/36034; A61N 1/36036
See application file for complete search history.

(56) References Cited

U.S. PATENT DOCUMENTS

| | | | |
|---|---|---|---|
| 9,974,478 | B1 | 5/2018 | Brokaw et al. |
| 10,076,655 | B2 | 9/2018 | Paul et al. |

(Continued)

OTHER PUBLICATIONS

Abdollah V, Dief TN, Ralston JD, Ho C, Rouhani H. "Investigating the Validity of a Single Tri-axial Accelerometer Mounted on the head for Monitoring the Activities of Daily Living and the Timed-Up and Go Test." Gait & Posture. Aug. 27, 2021; 90: 137-140. (Abdollah_2021-08-27.pdf).

(Continued)

*Primary Examiner* — Allen Porter
*Assistant Examiner* — Philip C Edwards
(74) *Attorney, Agent, or Firm* — FP Patents; Bruce A. Young; Sikander M. Khan

(57) ABSTRACT

Various embodiments relate to a method of providing restoration of vestibular function of a user. The method includes providing a plurality of treatment sessions, each session including affixing a first electrode on or near the user's mastoid and applying a subthreshold wideband stochastic electrical vestibular stimulation (swsEVS) waveform through the electrode. Persistent restoration of vestibular function is achieved and manifests as one or more of: regeneration of vestibular hair cells; increased synaptic gain between hair cells and vestibular nerve fibers; enhanced conductivity or excitability of afferent vestibular nerve fibers; removal of otoconia from semicircular canals; improved central neural integration and processing of vestibular, visual, and proprioceptive signals; augmented central generation of motor control signals; and elevated efferent feedback from the central nervous system to the vestibular inner ear.

50 Claims, 40 Drawing Sheets

Related U.S. Application Data

(60) Provisional application No. 63/882,262, filed on Sep. 15, 2025, provisional application No. 63/741,968, filed on Jan. 5, 2025, provisional application No. 63/719,613, filed on Nov. 12, 2024, provisional application No. 63/718,970, filed on Nov. 11, 2024, provisional application No. 63/711,642, filed on Oct. 24, 2024, provisional application No. 63/711,630, filed on Oct. 24, 2024, provisional application No. 63/302,094, filed on Jan. 23, 2022, provisional application No. 63/149,319, filed on Feb. 14, 2021.

(56) References Cited

U.S. PATENT DOCUMENTS

| | | | | |
|---|---|---|---|---|
| 2006/0173509 | A1 | 8/2006 | Lee et al. | |
| 2007/0167985 | A1 | 7/2007 | Kirby | |
| 2009/0198305 | A1 | 8/2009 | Naroditsky et al. | |
| 2009/0319004 | A1 | 12/2009 | Sabel | |
| 2010/0037694 | A1 | 2/2010 | Grossman | |
| 2011/0029045 | A1 | 2/2011 | Cevette et al. | |
| 2013/0090704 | A1 | 4/2013 | Kolen et al. | |
| 2014/0336722 | A1 | 11/2014 | Rocon De Lima et al. | |
| 2015/0005841 | A1 | 1/2015 | Pal et al. | |
| 2015/0032186 | A1 | 1/2015 | Cushing et al. | |
| 2015/0282767 | A1 | 10/2015 | Stivoric et al. | |
| 2017/0197081 | A1 | 7/2017 | Charlesworth et al. | |
| 2017/0308671 | A1 | 10/2017 | Bahrami et al. | |
| 2017/0333711 | A1 | 11/2017 | Tass et al. | |
| 2018/0055417 | A1 | 3/2018 | Munaretto | |
| 2018/0110466 | A1 | 4/2018 | Ralston | |
| 2018/0193641 | A1* | 7/2018 | Black | A61N 1/36028 |
| 2018/0272118 | A1 | 9/2018 | Goldwasser et al. | |
| 2018/0345016 | A1* | 12/2018 | Agada | A61B 5/0022 |
| 2018/0361153 | A1 | 12/2018 | Heldman et al. | |
| 2019/0046787 | A1 | 2/2019 | Tyler et al. | |
| 2019/0167095 | A1 | 6/2019 | Krueger et al. | |
| 2019/0371466 | A1 | 12/2019 | Nicolella et al. | |
| 2020/0009383 | A1 | 1/2020 | Waclawik | |
| 2020/0171307 | A1 | 6/2020 | Rockley et al. | |
| 2022/0047196 | A1 | 2/2022 | Kuboi | |
| 2022/0257149 | A1* | 8/2022 | Ralston | G16H 50/50 |
| 2022/0310196 | A1 | 9/2022 | Polykovskiy et al. | |
| 2022/0387781 | A1* | 12/2022 | Ramos de Miguel | A61N 1/0456 |

OTHER PUBLICATIONS

Abdollah V, Noamani A, Ralston JD, Ho C, Rouhani H. "Effect of Test Duration and Sensor Location on the Reliability of Standing Balance Parameters Derived Using Body-Mounted Accelerometers." BioMed Eng OnLine. 2024; 23: 2. doi: 10.1186/s12938-023-01196-7. (Abdollah_2024.pdf).

Ahmed, R.A.M.A., Fahmy, E.M., Awad, A.M. et al. Efficacy of transmastoidal galvanic stimulation on recovery outcomes in patients with unilateral peripheral vestibular disorders: a randomized controlled trial. Egypt J Neurol Psychiatry Neurosurg. 2020; 56: 75. doi: 10.1186/s41983-020-00207-x (Ahmed_2020.pdf).

Anson E, Bigelow RT, Studenski S, Deshpande N, Agrawal Y. "Failure on the Foam Eyes Closed Test of Standing Balance Associated with Reduced Semicircular Canal Function in Healthy Older Adults." Ear Hear. Mar./Apr. 2019, 40 (2): 340-344. (Anson_2019-03-01.pdf).

Araujo CG, de Souza E Silva CG, Laukkanen JA, Fiatarone Singh M, Kunutsor SK, Myers J, Franca JF, Castro CL. "Successful 10-second one-legged stance performance predicts survival in middle-aged and older individuals." Br J Sports Med. Sep. 2022; 56(17): 975-980. (Araujo_2022-09.pdf).

Assländer L, Peterka RJ. "Sensory reweighting dynamics in human postural control." J Neurophysiol. May 2014; 111 (9): 1852-1864. (Asslander_2014-02-05.pdf).

Baloh RW, Jacobson KM, Beykirch K, Honrubia V. "Static and dynamic posturography in patients with vestibular and cerebellar lesions." Arch Neurol. 1998; 55(5): 649-654. (Baloh_1998-05.pdf).

Biomarkers of Aging Consortium; Herzog CMS, Goeminne LJE, Poganik JR, Barzilai N, Belsky DW, Betts-LaCroix J,Chen BH, Chen M, Cohen AA, Cummings SR, Fedichev PO, Ferrucci L, Fleming A, Fortney K, Furman D, Gorbunova V, Higgins-Chen A, Hood L, Horvath S, Justice JN, Kiel DP, Kuchel GA, Lasky-Su J, LeBrasseur NK, Maier AB, Schilling B, Sebastiano V, Slagboom PE, Snyder MP, Verdin E, Widschwendter M, Zhavoronkov A, Moqri M, Gladyshev VN. "Challenges and recommendations for the translation of biomarkers of aging." Nat Aging. Oct. 2024; 4.

C. Fujimoto et al., Noisy galvanic vestibular stimulation induces a sustained improvement in body balance in elderly adults. Sci. Rep., vol. 6, No. 1, p. 37575, Nov. 2016, doi: 10.1038/srep37575. (Fujimoto_2016-11.pdf).

Clendaniel RA. "Outcome measures for assessment of treatment of the dizzy and balance disorder patient." Otolaryngol Clin North Am. Jun. 2000; 33(3): 519-533. (Clendaniel_2020-06.pdf).

De Á. Pires APB, Silva TR, Torres MS, Diniz ML, Tavares MC, Gonçalves DU. Galvanic vestibular stimulation and its applications: a systematic review. Brazilian Journal of Otorhinolaryngology. Nov. 2022; 88: S202-S211. doi: 10.1016/j.bjorl.2022.05.010. (Pires_2022-07-05.pdf).

Dlugaiczyk J, Gensberger KD, Straka H. Galvanic vestibular stimulation: From basic concepts to clinical applications. J Neurophysiol. 2019; 121(6):2237-2255. doi: 10.1152/JN.00035.2019 (Dlugaiczyk_2019-04-17.pdf).

El-Jaroudi A, Redfern MS, Chaparro LF, Furman JM. "The application of time-frequency methods to the analysis of postural sway." Proc IEEE. 1996; 84(9): 1312-1318. (El-Jaroudi_1996-09.pdf).

Ferdjallah M, Harris GF, Wertsch JJ. "Instantaneous spectral characteristics of postural stability using time-frequency analysis." Proc 19th Internat Conf—IEEE/EMBS; Oct. 30-Nov. 2; 1997; Chicago, IL. USA. (Ferdjallah_1997-10-30-pdf).

Ferreira RN, Ribeiro NF, Santos CP. "Fall Risk Assessment Using Wearable Sensors: A Narrative Review." Sensors (Basel). Jan. 27, 2022; 22(3): 984. (Ferreira_2022-01-27.pdf).

Fu W, Bai Y, Wang X. Galvanic vestibular stimulation for postural rehabilitation in neurological disorders: a systematic review. Front. Neurosci. 2025; 19:1580078. doi: 10.3389/fnins.2025.1580078 (Fu_2025-04-16.pdf).

Fujimoto C, Kamogashira T, Kinoshita M, et al. "Power spectral analysis of postural sway during foam posturography in patients with peripheral vestibular dysfunction." Otol Neurotol. 2014; 35(10): e317-e323. (Fujimoto_2014.pdf).

Gill J, et. al., "Trunk Sway Measures of Postural Stability During Clinical Balance Tests: Effects of Age," Journal of Gerentology: Medical Sciences 2001, vol. 56A, No. 7, M438-M447. (Gill_2001.pdf).

Grafton ST, Ralston AB, Ralston JD. Monitoring of postural sway with a head-mounted wearable device: Effects of gender, participant state, and concussion. Medical Devices: Evidence and Research. 2019; 12: 151-164. (Grafton_2019.pdf).

Guyot J. Milestones in the development of a vestibular implant. Curr Opin Neurol. 2019; 32(1): 145-153. (Guyot_2019-02.pdf).

Herssens N, McCrum C. Stimulating balance: recent advances in vestibular stimulation for balance and gait. J Neurophysiol. 2019; 122(2): 447-450. doi: 10.1152/JN.00851.2018 (Herssens_2019-03-13.pdf).

Hope A, Vashisth U, Parker M, Ralston AB, Roper JM, Ralston JD. "Phybrata Sensors and Machine Learning for Enhanced Neurophysiological Diagnosis and Treatment." Sensors 2021, 21, 7417. (Hope_2021-11-08.pdf).

Huang Y, Mao H, Chen Y. Regeneration of Hair Cells in the Human Vestibular System. Front Mol Neurosci. 2022; 15: 854635. doi: 10.3389/FNMOL.2022.854635 (Huang_2022-03-24.pdf).

Hwang TH, Effenberg AO. "Head Trajectory Diagrams for Gait Symmetry Analysis Using a Single Head-Worn IMU." Sensors (Basel). Oct. 5, 2021; 21(19): 6621. (Hwang_2021-10-05.pdf).

Jain A, Sarkar A, Gupta M. Optimizing Balance Using Vestibular Electrical Stimulation to Study its Therapeutic Effect Among Elderly.

(56) References Cited

OTHER PUBLICATIONS

Bioscience Biotechnology Research Communications. Apr.-May-Jun. 2022; 15(2): 313-320. (Jain_2022-06-30.pdf).
King J, Banman C, Walters N, Clark S, Ralston J, Peters R. Electrical Vestibular Stimulation Therapeutics for Balance and Gait in Older Adults. In: Canadian Association on Gerontology 52nd Annual Scientific and Educational Meeting. 2023. (King_2025.pdf).
Kwan A, Forbes PA, Mitchell DE, Blouin JS, Cullen KE. Neural substrates, dynamics and thresholds of galvanic vestibular stimulation in the behaving primate. Nat Commun. 2019; 10(1): 1-15. doi: 10.1038/S41467-019-09738-1 (Kwan_2019.pdf).
Lajoie K, Marigold DS, Valdes BA, Menon C. The potential of noisy galvanic vestibular stimulation for optimizing and assisting human performance. Neuropsychologia. 2021; 152. doi: 10.1016/j.neuropsychologia.2021.107751 (Lajoie_2021-01-09.pdf).
Lei Y, Rios V, Ji J, Duhon B, Boyd H, Xu Y. "Quantifying unsupported sitting posture impairments in humans with cervical spinal cord injury using a head-mounted IMU sensor." Spinal Cord. Feb. 2024; 62(2): 65-70. (Lei_2023-12-29.pdf).
Leopoldo CMS, Nishino LK, Santos MAO. "Use of posturography to identify the risk of falling in elderly people with dizziness." Audiol Commun Res. 2022; 27: e2684 (Leopoldo_2022.pdf).
Lin IS, Lai DM, Ding JJ, Chien A, Cheng CH, Wang SF, Wang JL, Kuo CL, Hsu WL. "Reweighting of the sensory inputs for postural control in patients with cervical spondylotic myelopathy after surgery." J Neuroeng Rehabil. Jul. 25, 2019; 16(1): 96. (Lin_2019-07-25.pdf).
Lockhart TE, Soangra R, Yoon H, Wu T, Frames CW, Weaver R, Roberto KA. "Prediction of fall risk among community-dwelling older adults using a wearable system." Scientific reports. Oct. 25, 2021; 11(1): 1-4. (Lockhart_2021-10-25.pdf).
Lopez C, Cullen KE, Electrical stimulation of the peripheral and central vestibular system. Curr. Opin. Neurol. Feb. 2024; 37(1): 40-51. (Lopez_2024-02.pdf).
Lubetzky AV, Harel D, Krishnamoorthy S, Fu G, Morris B, Medlin A, Wang Z, Perlin K, Roginska A, Cosetti M, Kelly J. "Decrease in head sway as a measure of sensory integration following vestibular rehabilitation: A randomized controlled trial." J Vestib Res. 2023; 33(3): 213-226. (Lubetzky_2023.pdf).
Marchand S, Langlade A, Legois Q. et al. A wide-ranging review of galvanic vestibular stimulation: from its genesis to basic science and clinical applications. Exp Brain Res. 2025: 243: 131. doi: 10.1007/s00221-025-07079-8 (Marchand_2025-04-27.pdf).
Meekes WM, Korevaar JC, Leemrijse CJ, van de Goor IA. "Practical and validated tool to assess falls risk in the primary care setting: a systematic review." BMJ Open. Sep. 29, 2021; 11(9): e045431. (Meekes_2021-09-29.pdf).
Micarelli A, Viziano A, Micarelli B, Di Fulvio G, Alessandrini M. "Usefulness of postural sway spectral analysis in the diagnostic route and clinical integration of cervicogenic and vestibular sources of dizziness: A cross-sectional preliminary study." J Vestib Res. 2021; 31(5): 353-364. (Micarelli_2021.pdf).
Mitsutake T, Sakamoto M, Kawaguchi A, Tamari M, Horikawa E. Greater functional activation during galvanic vestibular stimulation is associated with improved postural stability: a GVS-fMRI study. Somatosens Mot Res. 2020; 37 (4): 257-261. doi:10.1080/08990220.2020.1803256 (Mitsutake_2020-08-05.pdf).
Moqri M, Herzog C, Poganik JR; Biomarkers of Aging Consortium; Justice J, Belsky DW, Higgins-Chen A, Moskalev A, Fuellen G, Cohen AA, Bautmans I, Widschwendter M, Ding J, Fleming A, Mannick J, Han JJ, Zhavoronkov A, Barzilai N, Kaeberlein M, Cummings S, Kennedy BK, Ferrucci L, Horvath S, Verdin E, Maier AB, Snyder MP, Sebastiano V, Gladyshev VN. "Biomarkers of aging for the identification and evaluation of longevity interventions." Cell. Aug. 31, 2023;186(18):3758-3775. (Moqri_2023-08-31.pdf).
Müjdeci B, Aksoy S, Atas A. "Evaluation of balance in fallers and non-fallers elderly." Braz J Otorhinolaryngol. Oct. 2012;78(5):104-9. (Mujdeci_2012-10.pdf).
Pardasaney PK, Slavin MD, Wagenaar RC, Latham NK, Ni P, Jette AM. "Conceptual Limitations of Balance Measures for Community-Dwelling Older Adults." Physical Therapy. 2013; 93(10): 1351-1368. (Pardasaney_2013-05-23.pdf).
Pasma JH, Engelhart D, Maier AB, Schouten AC, van der Kooij H, Meskers CG. Changes in sensory reweighting of proprioceptive information during standing balance with age and disease. J Neurophysiol. Dec. 2015; 114(6): 3220-3233. doi: 10.1152/jn.00414.2015. (Pasma_2015-09-30.pdf).
Peusner KD, Shao M, Reddaway R, Hirsch JC. "Basic Concepts in Understanding Recovery of Function in Vestibular Reflex Networks during Vestibular Compensation." Front Neurol. Feb. 20, 2012; 3: 17. (Peusner_2012-02-20.pdf).
Quijoux F, Vienne-Jumeau A, Bertin-Hugault F, Zawieja P, Lefèvre M, Vidal PP, Ricard D. "Center of pressure displacement characteristics differentiate fall risk in older people: A systematic review with meta-analysis." Ageing Res Rev. Sep. 2020; 62: 101117. (QUIJOUX_2020-09.pdf).
Roshdibenam V, Jogerst GJ, Butler NR, Baek S. "Machine Learning Prediction of Fall Risk in Older Adults Using Timed Up and Go Test Kinematics." Sensors (Basel). May 17, 2021; 21(10): 3481. (Roshdibenam_2021-05-17.pdf).
Singh NB, Taylor WR, Madigan ML, Nussbaum MA. "The spectral content of postural sway during quiet stance: influences of age, vision and somatosensory inputs." J Electromyogr Kinesiol. 2011; 22 (1): 131-136. (Singh_2011.pdf).
Subramaniam S, Faisal Al and Deen MJ. "Wearable Sensor Systems for Fall Risk Assessment: A Review." Front. Digit. Health. 2022; 4: 921506. (Subramaniam_2022-07-14.pdf).
Tao X, Zhu Z, Wang L, Li C, Sun L, Wang W, Gong W. "Biomarkers of Aging and Relevant Evaluation Techniques: A Comprehensive Review." Aging Dis. May 7, 2024; 15(3):977-1005. (Tao_2024-06.pdf).
Torres EB, Mistry S, Caballero C, Whyatt CP. "Stochastic Signatures of Involuntary Head Micro-Movements Can Be Used to Classify Females of ABIDE into Different Subtypes of Neurodevelopmental Disorders." Front Integr Neurosci. Jun. 7, 2017; 11: 10. (Torres_2017-06.pdf).
Wagner AR, Akinsola O, Chaudhari AMW, Bigelow KE, Merfeld DM. "Measuring Vestibular Contributions to Age-Related Balance Impairment: A Review." Front Neurol. Feb. 9, 2021; 12: 635305. (Wagner_2021-02-09.pdf).
[No Author Listed] Neursantys NEURVESTA, retrieved from the internet athttps://cortex-design.com/work/neursantys/, on Jul. 29, 2025, 10 pages.
Agrawal Y. et al. "Vestibular dysfunction: prevalence, impact and need for targetedtreatment," J. Vestib. Res. 2013, 23(3): 113-177.
Araujo C.G. et al. "Successful 10-second one-legged stance performance predictssurvival in middle-aged and older individuals," Br. J. Sports Med., Sep. 2022,56(17):975-980.
Bidargaddi N. et al. "Wavelet based approach for posture transition estimationusing a waist worn accelerometer," In: Annual International Conference of the IEEEEngineering in Medicine and Biology—Proceedings. Annu Int Conf IEEE Eng Med BiolSoc, 2007, pp. 1884-1887.
Deveze A. et al. "Vestibular compensation and vestibular rehabilitation. CurrentConcepts and new trends," Neurophysiol. Clin., Jan. 2014, 44(1):49-57.
Fortino G. et al. "Enabling effective programming and flexible management ofefficient body sensor network applications," IEEE Transactions on Human-MachineSystems, 2013, 43:115-133.
Godfrey A. et al. "Activity classification using a single chest mounted tri-axialaccelerometer," Medical Engineering & Physics, 2011, 33:1127-1135.
Grafton S.T. et al., "Monitoring of postural sway with a head mounted wearabledevice: effects of gender, participant state, and concussion", Med Devices (Auckl), May 1, 2019, 12, pp. 151-164.
International Search Report and Written Opinion for International Application No. PCT/CA2022/050214 dated May 16, 2022, 18 pages.
King J, et al. "Electrical vestibular stimulation to improve static balance in older adults:a randomized control trial," Journal of NeuroEngineering and Rehabilitation, 2015, 29pages.

(56) References Cited

OTHER PUBLICATIONS

Mariani B. et al "3D gait assessment in young and elderly subjects using foot-worninertial sensors," Journal of Biomechanics, 2010, 43:2999-3006.
Martinez-Mendez, R., Sekine, M., & Tamura, T. (2011). Detection of anticipatory postural adjustments prior to gait initiation using inertial wearable sensors. Journal of NeuroEngineering and Rehabilitation, 8(1), 17. https://doi.org/10.1186/1743-0003-8-17 (Year: 2011).
Nazarahari M. et al. "A novel instrumented shoulder functional test using wearablesensors in patients with brachia! plexus injury," J. Shoulder Elbow Surg., 2021, 30, e493-e502.
Nazarahari M. et al. "Detection of daily postures and walking modalities using asingle chest-mounted tri-axial accelerometer," Medical Engineering and Physics, 2018,57:75-81.
Palermo E. et al "Experimental evaluation of accuracy and repeatability of a novelbody-to-sensor calibration procedure for inertial sensor-based gait analysis," Measurement, 2014, 52:145-155.
Paraschiv-Ionescu A. et al. "Barcoding human physical activity to assess chronicpain conditions," PLoS One, 2012, 7:e32239, 12 pages.
Paraschiv-Ionescu et al. "Ambulatory system for the quantitative and qualitativeanalysis of gait and posture in chronic pain patients treated with spinal cordstimulation," Gait and Posture, 2004, 20:113-125.
Rahmani M.H. et al. "Chest-Worn Inertial Sensors: A Survey of Applications andMethods," Sensors, 2021, 21 :2875, 30 pages.
Ralston and Stanley, "Neursantys and Caring Hands Caregivers Partner to PilotBioelectronic Balance Restoration for Senior Living Communities," Mar. 12, 2025, retrieved from the internet at https:// www .medtechdive.com/press-release/20250312-neursantys-and-caring-hands-caregivers-partner-to-pilot-bioelectronic-balan/, 6 pages.
Ralston JD et al. "Phybrata Digital Biomarkers of Age-Related BalanceImpairments, Sensory Reweighting and Intrinsic Fall Risk." Medical Devices: Evidenceand Research. Jun. 11, 2025, 18:319-336.
Ralston, J.D., et al., "Physiological Vibration Acceleration (Phybrata) SensorAssessment of Multi-System Physiological Impairments and Sensory ReweightingFollowing Concussion", Med Devices (Auckl), Dec. 8, 2020, vol. 13, pp. 411-438.
Rast, F.M., et al., "Systematic review on the application of wearable inertial sensorsto quantify everyday life motor activity in people with mobility impairments", Journal ofNeuro Engineering and Rehabilitation, Nov. 4, 2020, No. 17, vol. 148, pp. 1-19.
Rivera, L.F., et al. "Towards continuous monitoring in personalized healthcarethrough digital twins", GASCON '19: Proceedings of the 29th Annual InternationalConference on Computer Science and Software Engineering, Nov. 2019, pp. 329-335.
Rueden, L.V., et al., "Combining Machine Learning and Simulation to a HybridModelling Approach: Current and Future Directions", Berthold, M., Feelders, A., Krempl, G. ( eds) Advances in Intelligent Data Analysis XVIII, IDA Lecture Notes inComputer Science, 2020, vol. 12080. Springer, pp. 548-560.
Shumway-Cook A et al. "Predicting the Probability for Falls in Community-DwellingOlder Adults Using the Timed Up & Go Test," Physical Therapy, 2000, 80:896-903.
Sung P. and Rowland P. "Impact of sensory reweighting strategies on posturalcontrol using the sensory organization test in older adults with and without fall risks," Physiother Res. Int. Apr. 2014, 29(2):e2075, 10 pages.
Vestibular, retrieved from the internet athttps://sparxwellness.ca/services/vestibular/ on Jul. 29, 2025, 5 pages.
Wang J, Li Y, Yang GY, Jin K. Age-Related Dysfunction in Balance: A Comprehensive Review of Causes, Consequences, and Interventions. Aging Dis. Jan. 24, 2024; 16(2): 714-737. doi: 10.14336/AD.2024.0124-1. (Wang_2024-01-24.pdf).
Wang X, Cao J, Zhao Q, Chen M, Luo J, Wang H, Yu L, Tsui KL, Zhao Y. "Identifying sensors-based parameters associated with fall risk in community-dwelling older adults: an investigation and interpretation of discriminatory parameters." BMC Geriatr. Feb. 1, 2024; 24(1): 125. (Wang_2024-02-01.pdf).
White O, Babic J, Trenado C, Johannsen L, Goswami N. The promise of stochastic resonance in falls prevention. Front Physiol. 2019; 10: 427431. doi:10.3389/FPHYS.2018.01865 (White_2019-01-28.pdf).
Wiesmeier IK, Dalin D, Maurer C. "Elderly Use Proprioception Rather than Visual and Vestibular Cues for Postural Motor Control." Front Aging Neurosci. Jun. 23, 2015; 7: 97. (Wiesmeier_2015-06-23.pdf).
Williams HG, McClenaghan BA, Dickerson J. Spectral characteristics of postural control in elderly individuals. Arch Phys Med Rehabil. 1997; 78(7): 737-744. (Williams_1997-07.pdf).
Wuehr M, Decker J, Schniepp R. Noisy galvanic vestibular stimulation: an emerging treatment option for bilateral vestibulopathy. J Neurol. Oct. 2017; 264(Suppl 1): 81-86. doi: 10.1007/s00415-017-8481-4. (Wuehr_2017-10.pdf).
Y. Inukai et al., Effect of noisy galvanic vestibular stimulation in community-dwelling elderly people: a randomised controlled trial, J. NeuroEngineering Rehabil., vol. 15, No. 1, p. 63, Dec. 2018, doi: 10.1186/s12984-018-0407-6. (Inukai_2018-12.pdf).
Zatsiorsky VM, Duarte M. "Rambling and trembling in quiet standing." Motor Control. 2000; 4/2(2): 185-200. (Zatsiorsky_2000-05.pdf).
Zhang S, Xu W, Zhu Y, Tian E, Kong W. "Impaired Multisensory Integration Predisposes the Elderly People to Fall: A Systematic Review." Front. Neurosci. 2020: 14: 411. (Zhang_2020-04-28.pdf).
Zobeiri OA, Ostrander B, Roat J, Agrawal Y, Cullen KE. "Loss of peripheral vestibular input alters the statistics of head movement experienced during natural self-motion." J Physiol. Apr. 2021; 599(8): 2239-2254. (Zobeiri_2021-04-01.pdf).
Zoberiri O, et al., "Head movement kinematics are altered during balance stability exercises in individuals with vestibular schwannoma," Journal of NeuroEngineering and Rehabilitation (2022) 19:120 (Zoberiri_2022.pdf).

* cited by examiner

700

| | 710 | | | 720 | | | 730 | | |
|---|---|---|---|---|---|---|---|---|---|
| | 712 | 714 | 716 | 722 | 724 | 726 | 732 | 734 | 736 |
| # | 385 | 239 | 146 | 249 | 169 | 80 | 136 | 70 | 66 |
| MEAN | 76.2 | 74.7 | 78.6 | 75.9 | 74.5 | 78.8 | 76.7 | 75.1 | 78.3 |
| σ | 7.5 | 7.3 | 7.2 | 7.3 | 6.7 | 7.2 | 7.9 | 8.6 | 6.7 |
| MIN | 51 | 51 | 54 | 51 | 51 | 54 | 51 | 51 | 54 |
| MAX | 98 | 95 | 98 | 98 | 95 | 98 | 94 | 94 | 91 |

DETECTING AND TREATING NEUROPHYSIOLOGICAL IMPAIRMENT

CROSS-REFERENCE TO RELATED APPLICATIONS

This application claims the benefit of U.S. Provisional Patent Application No. 63/711,630 filed Oct. 24, 2024 and entitled "Systems and Methods for Cumulative and Persistent Enhancement, Preservation, or Restoration of Balance and Gait Stability," U.S. Provisional Patent Application No. 63/711,642 filed Oct. 24, 2024 and entitled "Systems and Methods for Reconfigurable and Programmable Bioelectronic Treatment Discovery and Delivery," U.S. Provisional Patent Application No. 63/718,970 filed Nov. 11, 2024 and entitled "Devices, Systems, and Methods for Bioelectronic Balance Therapeutics with Electrical or Electrohydrodynamic Stimulation of the Vestibular System," U.S. Provisional Patent Application No. 63/719,613 filed Nov. 12, 2024 and entitled "Devices, Systems, and Methods for Bioelectronic Balance Therapeutics via Peripheral and Central Sensory Neurogenesis," U.S. Provisional Patent Application No. 63/741,968 filed Jan. 5, 2025 and entitled "Digital Biomarkers of Age-Related Balance Impairments, Sensory Reweighting, and Intrinsic Fall Risk," and U.S. Provisional Patent Application No. 63/882,262 filed Sep. 15, 2025 and entitled "Devices, Systems, and Methods for Cumulative and Persistent Bioelectronic Restoration of Balance, Stabilization of Gait, and Reduction of Fall Risk. " This application is also a Continuation-In-Part of U.S. Patent Application No. 17/671,176, filed on Feb. 14, 2022 and entitled "Systems and methods for detecting and treating neurophysiological impairment." All of the aforementioned applications are hereby incorporated by reference in their entirety herein for any and all purposes.

TECHNICAL FIELD

The present subject matter relates to systems and methods that provide neurophysiological sensing and/or neurophysiological stimulation to quantify and treat neurophysiological impairments. More specifically, use of a physiological vibration acceleration (PHYBRATA) sensor to diagnose, and vestibular stimulation therapy (VST) to treat balance impairment as well as other neurophysiological impairments is disclosed.

BACKGROUND

The human balance system develops through complex neuroplastic learning processes that continue well into our teenage years and then start to decline again after the age of 40. Visual signals from our eyes tell us how objects in the world around us are moving, motion signals from the vestibular balance organs in our inner ear tell us how our own bodies are moving, and proprioceptive signals from our muscles and joints tell us how the orientation of our bodies changes as we move. Declining balance and mobility, clinically known as presbystasis, is one of the most visible and debilitating signs of aging. Age-related degeneration affects both the hearing organs 110 and the vestibular balance organs 120 in the inner ear, as illustrated in FIG. 1A. Dysfunction of the vestibular balance organs affects 35% of U.S. adults aged 40 years and older, and is the primary cause of balance decline in more than 55% of adults over age 50, which is more than 70 million Americans. The onset of vestibular impairments can also be accelerated by head trauma (such as concussions and stroke), diseases (such as Parkinson's disease and multiple sclerosis), and prolonged exposure to microgravity, which presents a fundamental medical challenge for all human activities in space. Current diagnostic solutions for vestibular balance impairments require clinical expertise and specialized equipment that most patients simply can't access. Even when vestibular balance impairments are diagnosed, current therapeutic options to restore disrupted vestibular function are limited to high-risk surgical vestibular implants. As a result, the only practical next step for many older adults is a mechanical walker, which can actually degrade balance even further. The economic burden of age-related balance impairments in the U.S. is significant, with almost $300 billion in costs at stake to justify developing better solutions to manage balance disruptions.

FIG. 1B shows more detail of the vestibular balance organs 120 in a human. The view of the vestibular balance organs 120 in FIG. 1B is a straight lateral view as shown 101. The vestibular balance organs 120 include two otolith organs, a utricle 123 and a saccule 125, that sense linear motion and three semicircular canals (including the posterior semicircular canal 121) that sense rotational motion. Each of the three semicircular canals is a narrow membranous ring, filled with fluid (endolymph), that encompasses about two thirds of a circle. The semicircular canals originate from the sac containing the utricle 123, and each terminates at an enlarged area (ampulla) that contains the crista/cupula complex embedded with bundles of motion sensing hair cells (kinocilia and stereocilia). During linear head movements along the axis of each otolith and rotations in the plane of each canal, the relative inertia of endolymph causes it to move freely with respect to the skull, bowing the hair cells within the otoliths and the semicircular canals. This deflection of the stereocilia and kinocilia in turn generates nerve signals proportional to the corresponding linear and rotational motions that get transmitted along the vestibular nerve to the vestibular nucleus in the brainstem, and from there they are distributed widely throughout the central nervous system (CNS). The CNS integrates vestibular, visual, and proprioceptive inputs to produce motor control outputs that allow us to stand upright, walk steadily, keep objects in visual focus during head movements, and perform complex actions without losing balance. The vestibular system also provides critical information about spatial orientation required for development and proper functioning of many other physiological and cognitive processes from infancy through adulthood.

The utricle 123 and the saccule 125 are oriented and specialized to respond to horizontal and vertical motion, respectively. Each organ has a sheet of hair cells, the macula, with both supporting cells and motion sensing hair cells (stereocilia) embedded in endolymph fluid, similar to the semicircular canals. Unlike the semicircular canals, however, the otoliths also contain small crystals of calcium carbonate called otoconia 130, embedded in a gelatinous mass. The weight and inertia of these small particles increase the deflection of the hair cells when the head moves. Degeneration of the otoconia with age contributes to age related balance decline. Benign Paroxysmal Positional Vertigo (BPPV), a common vertigo condition, is caused by otoconia migrating and becoming lodged in the semicircular canals, such as a displaced otoconia 135. Free-floating otoconia 130 move the endolymph fluid in the narrow semicircular canal as they are displaced by gravity and other motions, which is turn displace the cupula and create erroneous sensations of rotational motion. Vestibular therapists can use specialized movements of the head to detect the presence and location of lodged otoconia 135, and to remove the particles from the semicircular canals. Devices have also been developed that deliver electromechanical vibrations to the vestibular system to mask the erroneous sensations of rotational motion.

Meniere's disease, caused by fluid buildup in the various compartments of the vestibular labyrinth, may be caused by viral infections, allergies, autoimmune response, genetics, or other factors that lead to pressure buildup and swelling in the inner ear.

As people age, they lose the vestibular hair cells, and as a result, the sensory signals generated by the vestibular organs get weaker. This triggers a cascade of additional atrophy effects in the other components of the vestibular system, including decrease in the gain of the synapses between the motion sensing cells and the vestibular nerve and decreased conductivity along the vestibular nerve, both of which further weaken the signals received by the brain, which can lead to atrophy in many parts of the brain itself that integrate and process all of the related sensory input and motor control output signals.

The vestibulo-ocular, vestibulocollic, and vestibulospinal reflexes are three motion reflexes that are triggered by signals from the vestibular balance organs 120 and work together to maintain balance, clear vision, and stable posture. The vestibulo-ocular reflex (VOR) moves the eyes in the opposite direction of the head to maintain a stable image on the retina. The vestibulocollic reflex (VCR) stabilizes the head on the neck to keep the visual and auditory systems aligned. The vestibulospinal reflex (VSR) stabilizes the body through compensatory movements to prevent falls. The CNS processes this information together with visual and proprioceptive inputs to generate signals that control eye, neck, and body movements to maintain balance and clear vision. A disruption in any of these reflexes can lead to symptoms like blurry vision during head movement, dizziness, or unsteadiness.

A key element of CNS processing is sensory reweighting (SR), the process by which the brain continuously evaluates the reliability and recalibrates the relative importance, or weighting, that it assigns to visual, vestibular, and proprioceptive sensory inputs. SR allows the brain to amplify or attenuate signals from different sensory systems based on their perceived reliability. SR can occur dynamically, in response to changing environmental factors such as poor lighting or uneven surfaces, or it can occur slowly over time, in response to changing physiological factors, such as loss of vestibular hair cells, decline in vision, or peripheral neuropathies that degrade proprioceptive signals. Age-related reductions in the response time or accuracy of the SR process significantly increase fall risks in older people.

Traditional methods of reliably diagnosing balance and mobility decline, vestibular-specific impairments, changes in SR, and related fall risks require specialized laboratory equipment, such as computerized dynamic posturography (CDP) systems. These systems are costly and require dedicated facilities and trained staff, and they are typically available only in balance and gait research labs or specialized neuromotor clinics that are not widely accessible to most older patients with declining balance and postural control. As a result, most clinicians assessing balance in their older patients day-to-day are limited to visually scored tests or self-reported scales for balance, dizziness, ambulatory performance, and fall risks. While low-cost and easy to perform, their reliability and utility are limited and more than half of elderly patients with balance disorders report vague, inconsistent, or contradictory descriptions of their symptoms. Earlier detection and more effective management of vestibular dysfunction in older adults hinges on the development of more objective and readily available diagnostic methods.

The present invention discloses a novel wearable physiological vibration acceleration (PHYBRATA) sensor and digital biomarkers that provide such a method for diagnosing balance and mobility decline, vestibular-specific impairments, changes in SR, and related fall risks.

The current standard treatment for older adults diagnosed with vestibular decline is vestibular rehabilitation therapy (VRT). VRT is an exercise-based regimen delivered by physical and occupational therapists with specialized vestibular training. However, due to a severe shortage of trained vestibular specialists, only a small fraction of the more than 70 million vestibular-impaired older adults over the age of 50 in the U.S. receive VRT. For those who do, the primary aim of VRT is to help patients compensate for their vestibular loss by making greater use of vision and proprioception, rather than restoring degraded vestibular function or preventing further deterioration.

Prescription medications, known as vestibular suppressants, are available to alleviate acute symptoms such as dizziness, nausea, and vertigo. However, these drugs come with significant side effects and are prescribed for only a few days to manage acute symptoms. Since they have no prophylactic or therapeutic role, they are unsuitable for long-term treatment for older adults without acute symptoms or as preventative interventions.

Vestibular implants represent the only current option to restore vestibular function, but these experimental devices require a high-risk invasive surgical procedure and are limited to patients with severe damage or loss of their vestibular organs. Consequently, they are not expected to become a widely available or economically viable solution for normal age-related balance decline. When fall risks become critical, the most common solution offered to older adults is some combination of mobility assistive devices (canes, walkers, etc.). However, these interventions may be counterproductive, since they can potentially exacerbate vestibular dysfunction and further degrade quality of life.

BRIEF DESCRIPTION OF THE DRAWINGS

The accompanying drawings, which are incorporated in and constitute part of the specification, illustrate various embodiments. Together with the general description, the drawings serve to explain various principles. In the drawings.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well-known methods, procedures and components have been described at a relatively high level, without detail, in order to avoid unnecessarily obscuring aspects of the present concepts. A number of descriptive terms and phrases are used in describing the various embodiments of this disclosure. These descriptive terms and phrases are used to convey a generally agreed upon meaning to those skilled in the art unless a different definition is given in this specification.

Some descriptive terms and phrases are presented in the following paragraphs for clarity.

PHYBRATA, as used herein, refers to physiological vibration acceleration of a user's head, which is most typically measured with a set of accelerometers (a PHYBRATA sensor), mounted behind a user's ear using a disposable adhesive. Thus, a PHYBRATA sensor may include one or more accelerometers.

Patient, subject, user, and participant are used interchangeable herein to refer to a human that is being assessed and/or treated for a balance disorder.

Reference now is made in detail to the examples illustrated in the accompanying drawings and discussed below.

Figure 1A:
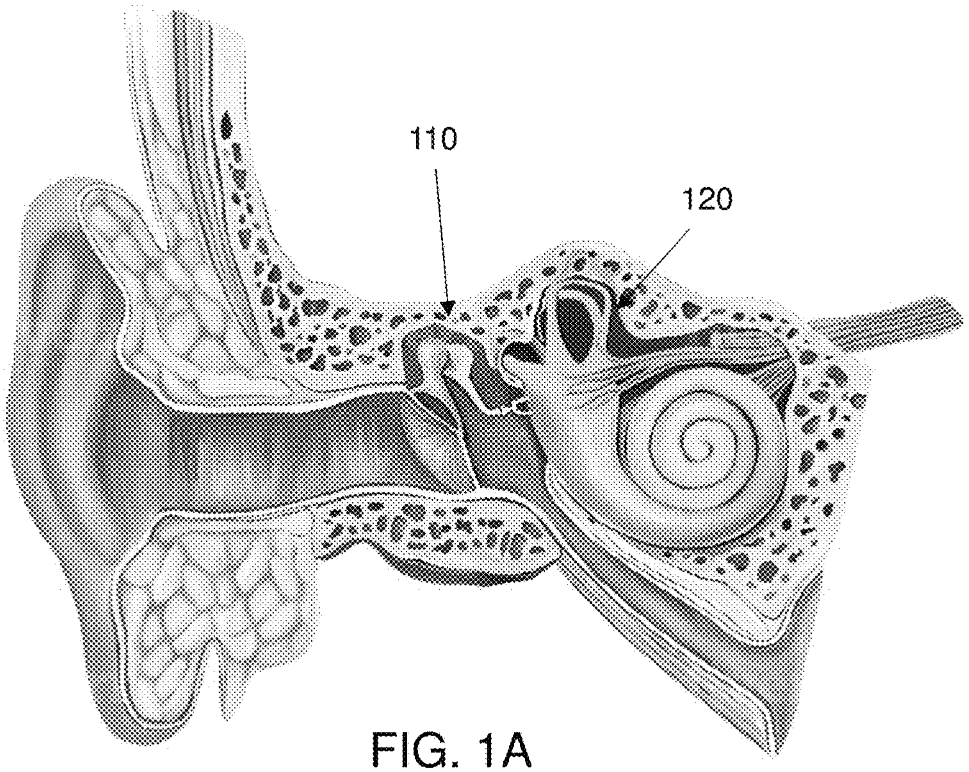
FIG. 1A PRIOR ART
FIG. 1A illustrates hearing organs and balance organs in a human.
Figure 1B:
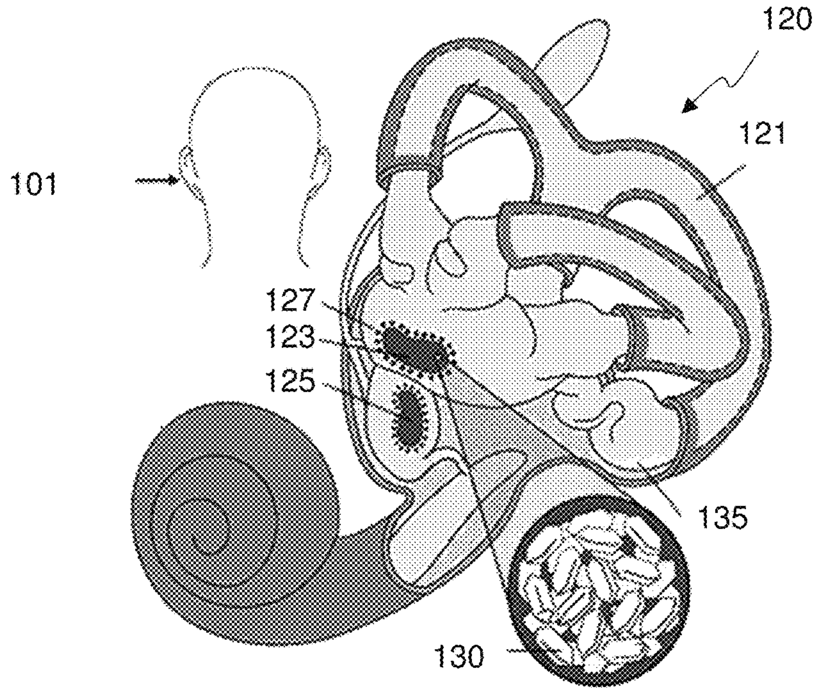
FIG. 1B PRIOR ART
FIG. 1B shows more detail of the balance organs in a human.
Figure 2:
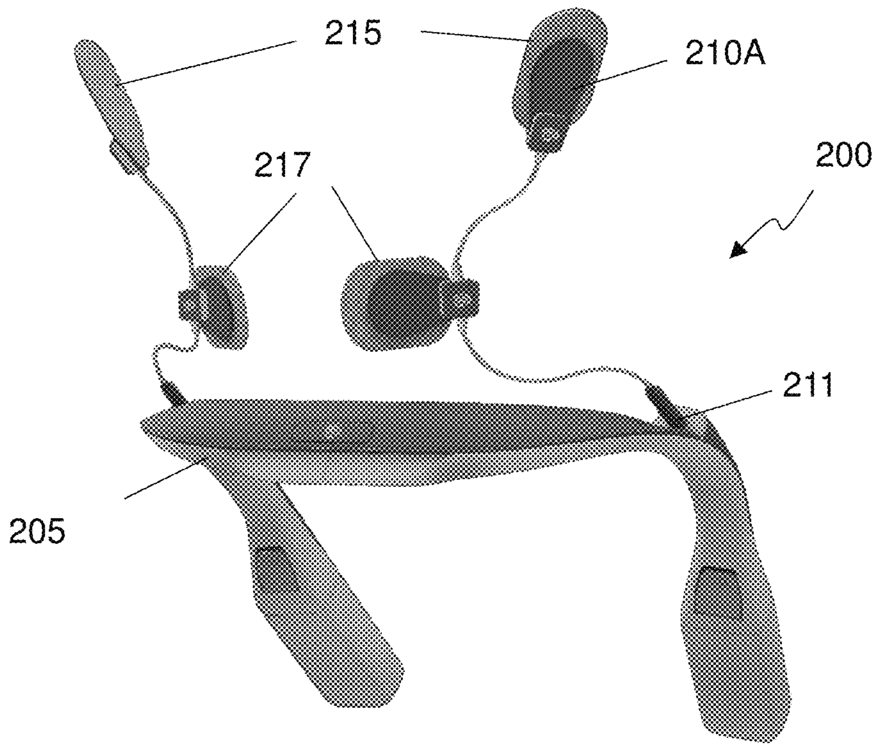
FIG. 2 shows an example wearable medical device, or NEURVESTA device, for assessing and treating balance disorders.
Figure 3:
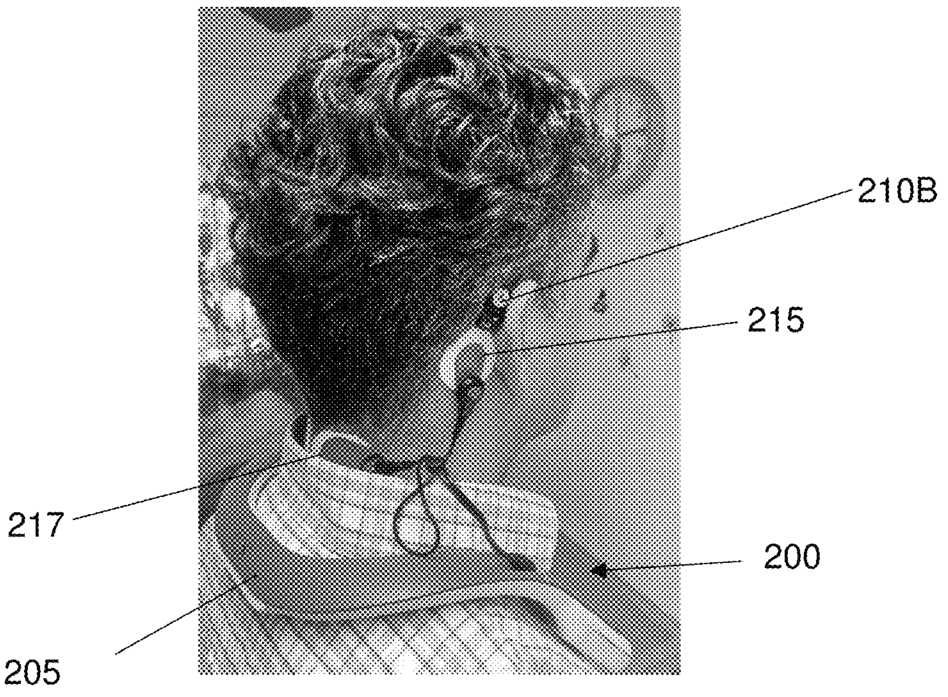
FIG. 3 shows a human subject wearing the NEURVESTA device shown in FIG. 2.

FIG. 2 shows an example wearable medical device for treating balance disorders, which is referred to herein as a NEURVESTA device 200. The NEURVESTA device 200 is a wearable medical device that delivers a unique form of electrical stimulation to the vestibular balance system to help restore disrupted vestibular balance functions. It has a collar 205 which is designed to fit over a patient's neck, as shown in FIG. 3, and two pairs of electrodes 215 that are attached to the collar 205 by wires. The wires connecting the electrodes 215 to the collar may be permanently attached at both ends or may have a connector 211 at one end to allow the wires to be easily detached from the collar 205 and replaced if they are damaged, and/or a connector at the other end to allow the electrodes 215 to be easily detached from the wires in the case where the electrodes 215 are disposable and designed for a single use. FIG. 3 also shows a PHYBRATA diagnostic sensor 210B attached behind a patient's ear. The NEURVESTA electrodes 215 are typically disposable pre-gelled single-use adhesive electrodes attached behind the ears of a patient, to the right and left mastoid. In some implementations, the PHYBRATA sensor 210B may be separate from the electrodes 215. In other implementations, the PHYBRATA sensor 210A may be integrated with one of the NEURVESTA electrodes 215. The NEURVESTA device 200 may include a second set of electrodes 217 configured to be attached to the back of a patient's neck. The neck electrodes 217 may be attached to the collar 205 by wires, or they may be integrated into the collar 205. The therapeutic function of the NEURVESTA device 200 is delivered using miniaturized neurostimulation electronics embedded in the collar 205.

Figure 4:
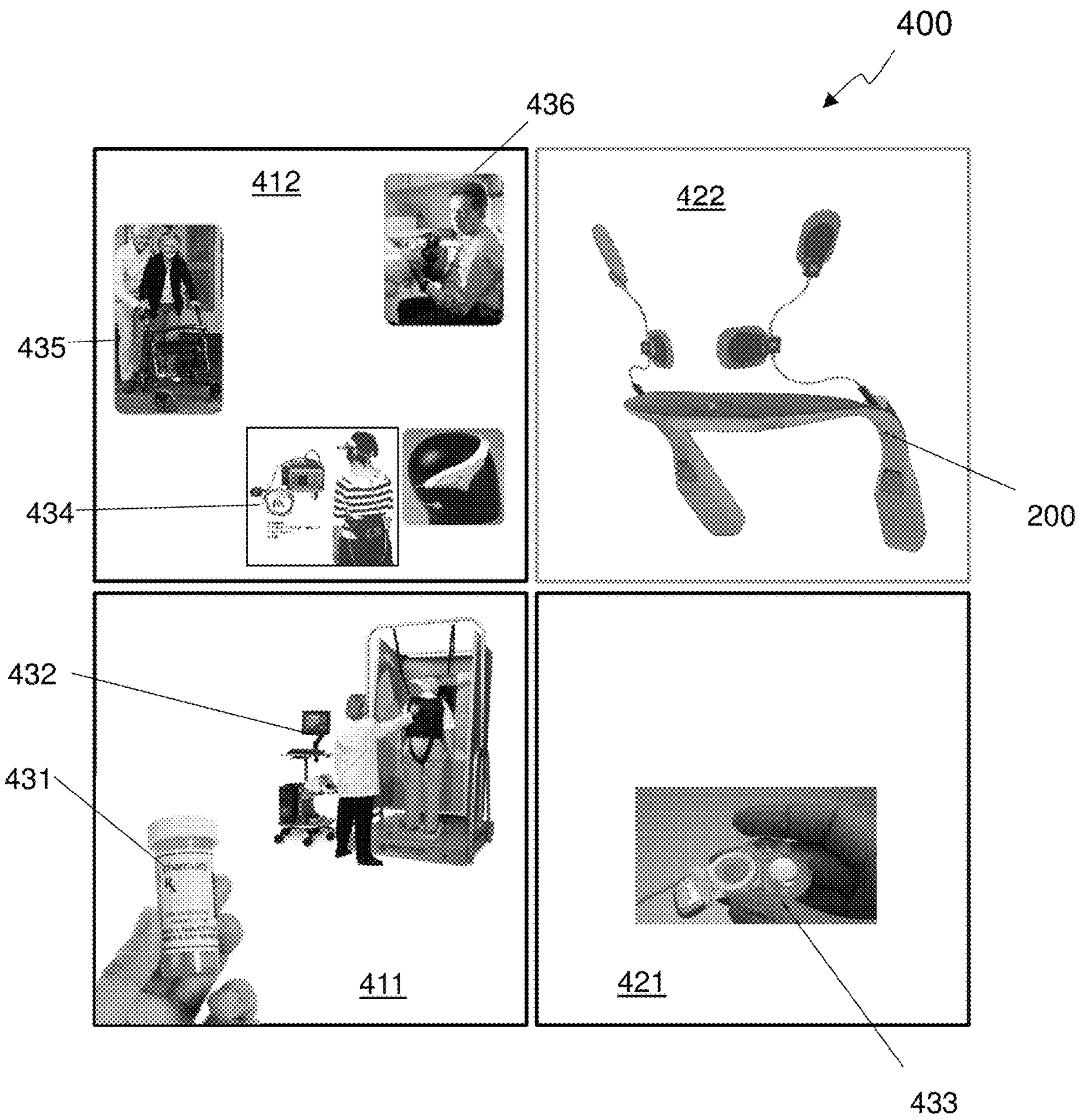
FIG. 4 summarizes benefits of the NEURVESTA device in comparison to available alternatives.

FIG. 4 summarizes benefits of the NEURVESTA device in comparison to available alternatives. The chart 400 shows a grid where cost and risk are low at the top and high at the bottom, and efficacy is low at the left and high at the right. This creates four quadrants of potential solutions. The lower left quadrant 411 is low efficacy and high cost/risk. Examples of solutions in this quadrant 411 include vestibular suppressants 431 which do not restore vestibular functions, and laboratory solutions 432 which may be difficult to scale to large numbers of patients. The lower right quadrant 421 is high efficacy but high cost/risk. An example of a solution in this quadrant 421 is vestibular implants 433 which are experimental, high risk, and invasive. The upper left quadrant 412 is low cost/risk but also low efficacy. Examples of solutions in this quadrant 412 include portable stimulation devices 434 which have no effective balance restoration protocols, assisted walking devices 435 which accelerate balance decline, and balance/vestibular rehab therapies 436 which only compensate for vestibular function and don't actually improve it.

The upper right quadrant 422 is high efficacy, low cost, and low risk. The only device in this quadrant is the NEURVESTA device 200.

Figure 5:
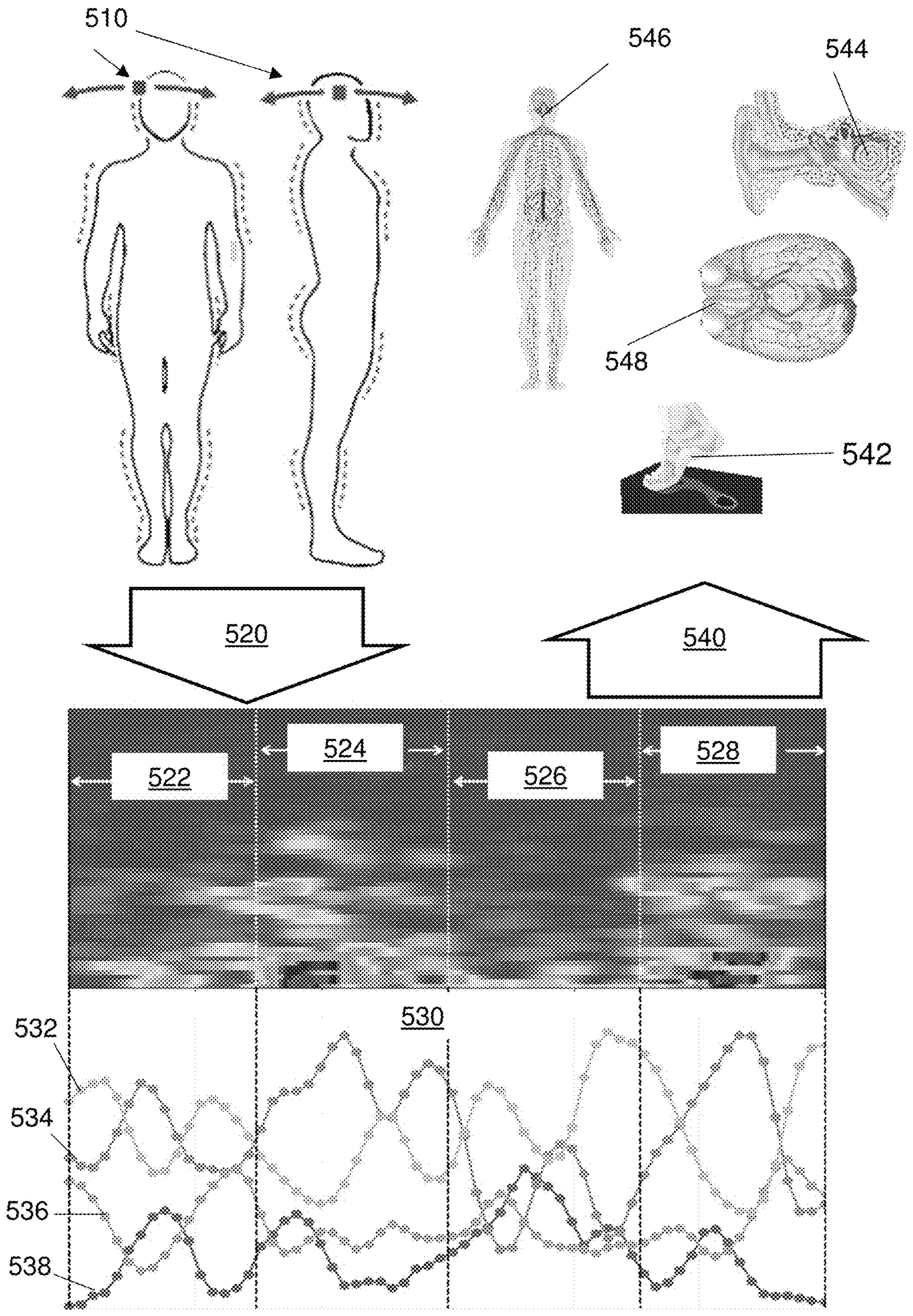
FIG. 5 shows an illustration of an example diagnostic function of the PHYBRATA sensor.

FIG. 5 illustrates the diagnostic function of the PHYBRATA sensor 210A/210B attached behind the ear of the patient using a disposable adhesive. The PHYBRATA sensor 210A/210B functions as an extremely sensitive seismometer for the human body, detecting subtle involuntary movements during standing balance and walking gait tests. The head-mounted design and tiny mass of the device enable the separation of postural control contributions from visual, vestibular, and proprioceptive inputs along with CNS processing by mapping them to specific vibrational frequency bands in the PHYBRATA data.

Balance impairment screening using the PHYBRATA sensor 210A/210B has been conducted on over 3,000 individuals ranging in age from 8 to 98 years, allowing for derivation of robust PHYBRATA-based biomarkers that effectively quantify changes in postural stability and sensory reweighting due to aging, head trauma such as concussions, diseases like multiple sclerosis, and spinal cord injuries. The diagnostic performance of the PHYBRATA sensor 210A/210B has been shown to match that of other methods, including computerized dynamic posturography (CDP), full-body video motion capture, and various inertial motion units mounted on other parts of the body, in assessing standard balance and gait parameters, as well as postural transitions during activities of daily living. The combination of PHYBRATA sensor data and machine learning (ML) has been shown to outperform the diagnostic performance of alternatives such as neurocognitive tests, clinical scales, symptoms checklists, balance and gait testing, magnetic resonance imaging (MRI), electroencephalography (EEG), eye tracking, and blood biomarkers.

As illustrated in FIG. 5, the PHYBRATA sensor detects 510 microscopic involuntary motions of the patient's head and body during simple balance and gait tests, both normal motions that we expect to observe in healthy individuals, and pathological motions caused by any impairments that disrupt balance and gait. Measuring these motions at the head enables the derivation of PHYBRATA biomarkers that independently identify and quantify impairments to multiple physiological systems in the body based on the unique contributions that they make to biomechanical stabilization of the head and eyes as the reference platform used by the body to enable balance and movement. If a patient has a vestibular balance impairment, the PHYBRATA sensors will identify it and quantify it.

The PHYBRATA sensor collects 520 data about the movements of the patient's head. In some implementations, data may be collected during multiple consecutive test periods, such as a first period 522 where the patient's eyes are open, a second period 524 where the patient's eyes are closed, a third period 526 where the patient's eyes are open, and a fourth period 528 where the patient's eyes are closed again. The data collected may be analyzed in different ways, depending on the implementation. The upper part of the graph 530 shows data from an example patient data transformed into the frequency domain with the bottom of the colored area being 0 Hertz (Hz) and the top of the colored area being 30 Hz. Different colors represent different amplitudes of the various frequency bands over time which increases to the right.

Different frequency bands correlate with different functional elements of the human balance system. The bottom part of the graph in FIG. 5 shows the relative contribution of the various functional elements to balance over the duration of the test periods 522-528, with the yellow data 532 indicative of proprioceptive balance control, the orange data 534 indicative of vestibular balance control, the grey data 536 indicative of central nervous system activation during balance control, and the blue data 538 indicative of visual balance control. Thus, the various contributions to balance control and any related impairments can be classified 540 into impairments of proprioceptive balance control 542, vestibular balance control 544, the central nervous system (CNS) 546, and/or visual balance control 548.

Figures 6, 7:
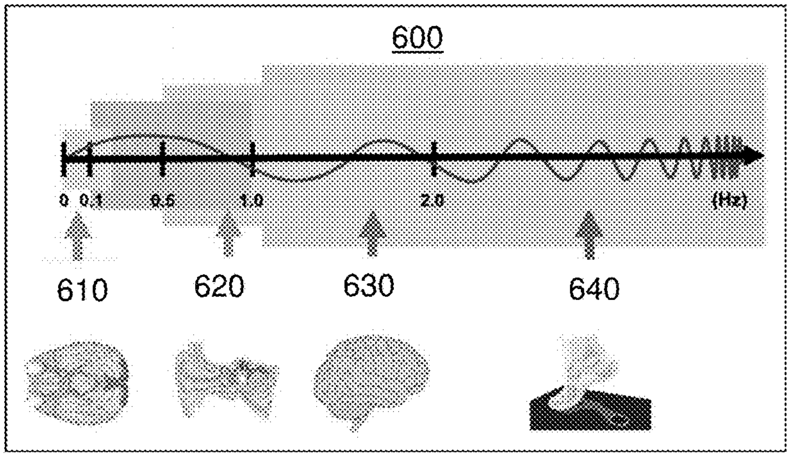
FIG. 6 shows how different frequency bands of PHYBRATA data map to different sensory inputs and CNS control during a standing balance test.
FIG. 7 is a table showing data from a survey of reported fall histories.

FIG. 6 shows a mapping 600 of specific vibrational frequency bands in the PHYBRATA data (i.e., data collected using a PHYBRATA sensor 210B) to their corresponding human body system contributing to balance. Vision-based balance control manifests in very low frequencies 610, such as about 0.0-0.2 Hz which may be truncated to 0.0-0.1 Hz for analysis to avoid overlap with other bands. Vestibular-based balance control manifests in a frequency range 620 of about 0.1-1.0 Hz which may be truncated to 0.1-0.5 Hz for analysis to avoid overlap with other bands. CNS processing of balance information shows up in a frequency range 630 of about 0.5-2.0 Hz which may be truncated to 0.5-1.0 Hz for analysis to avoid overlap with other bands, and proprioception and muscular activity is indicated in a frequency range 640 of 1.0-10 Hz. In some systems the vestibulocollic reflex (VCR) in a frequency range of 10-25 Hz is also evaluated.

This mapping is based on previous studies of neuromotor control and the effects of impairments in both humans and humanoid robots. By distinguishing between normal and pathological patterns, a single head-mounted PHYBRATA sensor 210A/210B can quantify balance and gait instabilities, vestibular-specific impairments, sensory reweighting, and fall risks, while also tracking patient responses to clinical interventions.

PHYBRATA data can quantify the progressive decline in postural stability that accompanies aging. In one study, PHYBRATA data were collected and analyzed from 385 participants aged 76.2±7.5 yrs (min 51 yrs, max 98 yrs, 136 male, 249 female) in 3 residential senior living centers. Participants first completed a questionnaire that included their fall history in the past 6 months and a list of risk factors that may contribute to balance impairment and fall risks. Risk factors included

- Lower joint pain
- Back pain
- Weakness in limbs
- Edema
- Osteoarthritis
- Knee/hip replacement
- Poor vision
- Dizziness/vertigo
- Sleep apnea
- Low blood pressure
- High blood pressure
- Obesity
- High cholesterol
- Diabetes
- Neuropathy
- Hypothyroidism
- Heart disease
- Deep vein thrombosis
- Lung disease
- Alzheimer's
- Parkinson's
- Multiple sclerosis
- Stroke FIG. 7 is a table 700 showing data from a survey of reported fall histories for the 385 participants. The first row shows a number or participants each column of data, the second row shows the mean ages of the participants for that column, the third row shows the standard deviation of that column's ages, the fourth row the minimum age for that column, and the fifth row shows the maximum age for that column. The second through fifth rows provide their data in years. The set of columns 710 show data from all participants, with column 712 reporting data for all participants, column 714 showing all participants that did not report any falls, and column 716 showing all participants that reported falling. 146 participants reported falling one or more times in the previous 6 months. The set of columns 720 show data from female participants, with column 722 reporting data for all female participants, column 724 showing female participants that did not report any falls, and column 726 showing female participants that reported falling. 80 female participants reported falling one or more times in the previous 6 months. The set of columns 730 show data from male participants, with column 732 reporting data for all male participants, column 734 showing male participants that did not report any falls, and column 736 showing male participants that reported falling. 66 male participants reported falling one or more times in the previous 6 months.

Standing balance tests were then carried out for all participants, who lived in residential senior living centers, using a PHYBRATA sensor. Data from this study is shown in various forms in FIG. 8A through FIG. 14. PHYBRATA time series data and spatial scatter plots, eyes open (Eo) and eyes closed (Ec) PHYBRATA powers, average power (Eo+Ec)/2, Ec/Eo PHYBRATA power ratio, time-resolved PHYBRATA power spectral density (PSD) distributions, and receiver operating characteristic (ROC) curves are compared for participants with no reported fall history and those reporting one or more falls in the past 6 months. Differences are also analyzed for individuals listing no risk factors, those listing one or two risk factors, and those listing three or more risk factors. 730 participants at one testing site also completed timed-up-and-go (TUG) tests.

The PHYBRATA data in the sequence of figures from FIG. 8A to FIG. 14 correlate with the progressive decline in postural stability, impairments across multiple sensory systems, corresponding sensory reweighting, and the degradation of vestibular function and CNS processing. These factors contribute to age-related balance degradation and increased intrinsic fall risk. PHYBRATA biomarkers serve as a standard measure of both absolute and relative balance performance, vestibular impairments, and fall risk, significantly outperforming traditional clinical examinations and many laboratory balance and gait analysis systems.

Figure 8A:
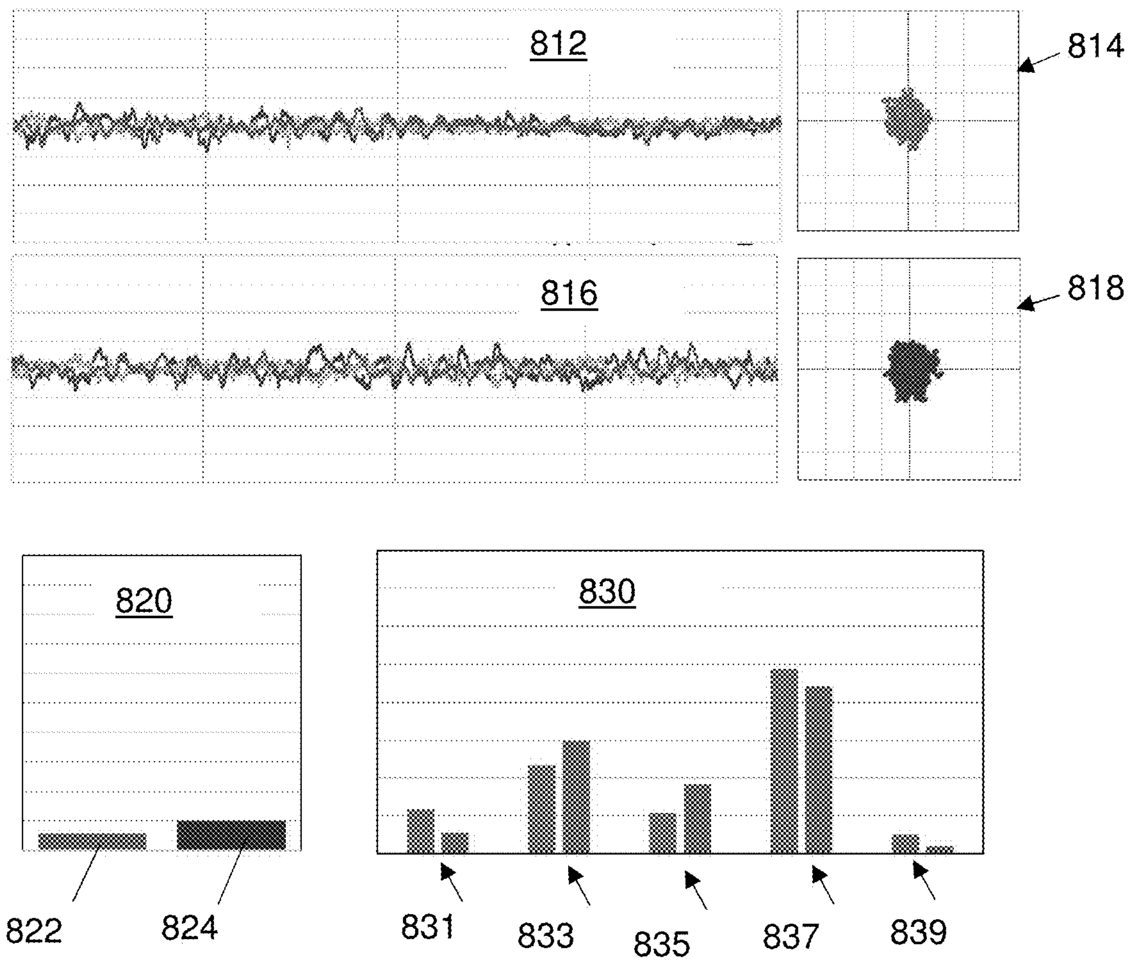
FIG. 8A, FIG. 8B, and FIG. 8C show sample PHYBRATA data from standing balance tests on three participants in the survey.

FIG. 8A shows the data from a 51-year-old female participant who did not report falling. Graph 812 shows the PHYBRATA time series data for a test with the participant's eyes open. The red line shows acceleration along the x-axis, the green line shows acceleration along the y-axis, and the blue line shows acceleration along the z-axis. Scatter plot 814 shows anteroposterior (AP) acceleration (y-axis) vs mediolateral (ML) acceleration (x-axis) based on the data from graph 812. Graph 816 shows the PHYBRATA time series data for a test with the participant's eyes closed. The red line shows acceleration along the x-axis, the green line shows acceleration along the y-axis, and the blue line shows acceleration along the z-axis. Scatter plot 818 shows AP/ML acceleration based on the data from graph 818. Note that the AP/ML data in both scatter plots 814, 818 is tightly bunched for this participant who reported no falls, which was representative of participants who did not report falling.

Graph 820 shows the PHYBRATA power for the two tests. The blue bar 822 on the left shows the power for the eyes open (Eo) test and the red bar 824 on the right shows the power for the eyes closed (Ec) test. The low values of Eo and Ec PHYBRATA powers (Eo<0.5 watts, Ec<0.6 watts) indicate normal healthy balance and low fall risk. The ratio Ec/Eo <2 indicates normal healthy vestibular function, which was representative of the group that did not report falling.

Graph 830 shows the results of analyzing the PHYBRATA frequency data to identify contributions to balance from various body systems as shown in FIG. 6. The blue bars (left bar of each set of bars) show data for eyes open, and the red bars (right bar of each set of bars) show data for eyes closed. Bars 831 show the balance contribution from the visual system, bars 833 show the balance contribution from the vestibular system, bars 835 show the balance contribution from the central nervous system, bars 837 show the balance contribution from proprioceptive systems, and bars 839 show the contribution from VCR.

Figure 8B:
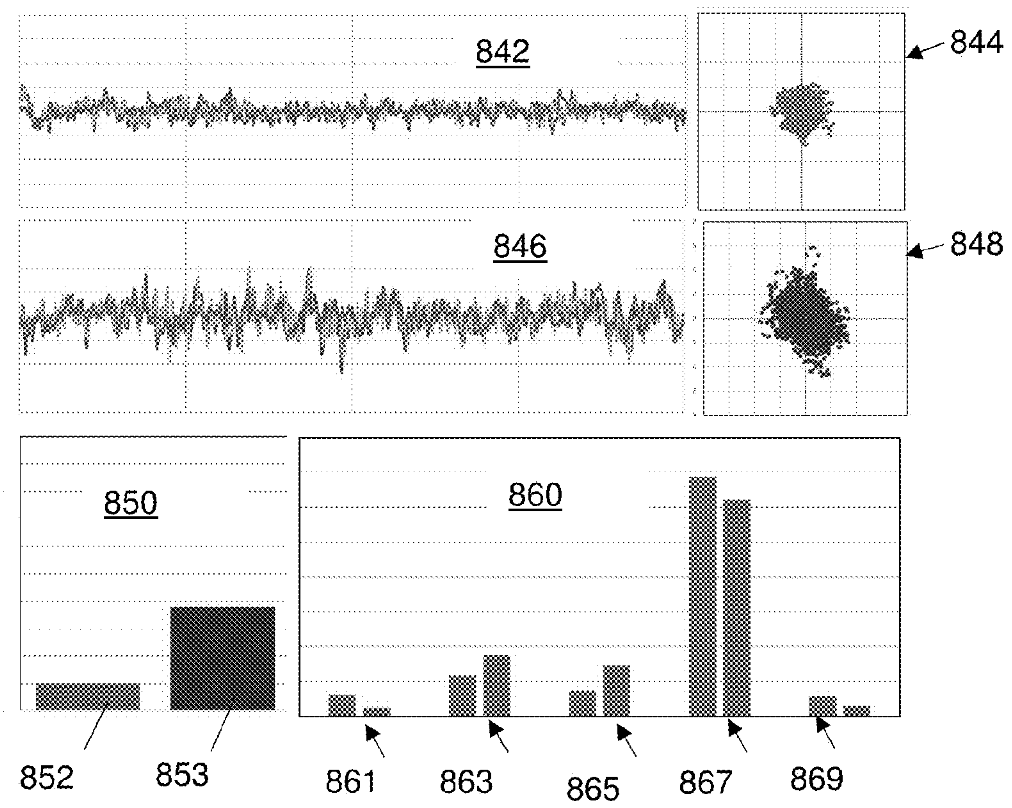

FIG. 8B shows the data from an 81-year-old female participant who reported falling once in the previous 6 months. Graph 842 shows the PHYBRATA time series data for a test with the participant's eyes open. The red line shows acceleration along the x-axis, the green line shows acceleration along the y-axis, and the blue line shows acceleration along the x-axis. Scatter plot 844 shows anteroposterior (AP) acceleration (y-axis) vs mediolateral (ML) acceleration (x-axis) based on the data from graph 842. Graph 846 shows the PHYBRATA time series data for a test with the participant's eyes closed. The red line shows acceleration along the x-axis, the green line shows acceleration along the y-axis, and the blue line shows acceleration along the x-axis. Scatter plot 848 shows AP/ML acceleration based on the data from graph 848. Note that the AP/ML data in both scatter plots 844, 848 is not as tightly bunched for this participant as it was for the 51-year-old participant who reported no falls, especially the scatter plot 848 for the data with eyes closed.

Graph 850 shows the PHYBRATA power for the two tests. The blue bar 852 (left) shows the power for the eyes open test and the red bar 853 (right) shows the power for the eyes closed test. The significantly higher value of Ec PHYBRATA power (Ec>0.6 watts) indicates impaired balance and elevated fall risk. The elevated ratio Ec/Eo>2 indicates impaired vestibular function. Both behaviors were representative of the group that reported a single fall in the previous 6 months.

Graph 860 shows the results of analyzing the PHYBRATA frequency data to identify contributions to balance from various body systems. The blue bars (left) show data for eyes open, and the red bars (right) show data for eyes closed. Bars 861 show the balance contribution from the visual system, bars 863 show the balance contribution from the vestibular system, bars 865 show the balance contribution from the central nervous system, bars 867 show the balance contribution from proprioceptive systems, and bars 869 show the contribution from VCR.

Figure 8C:
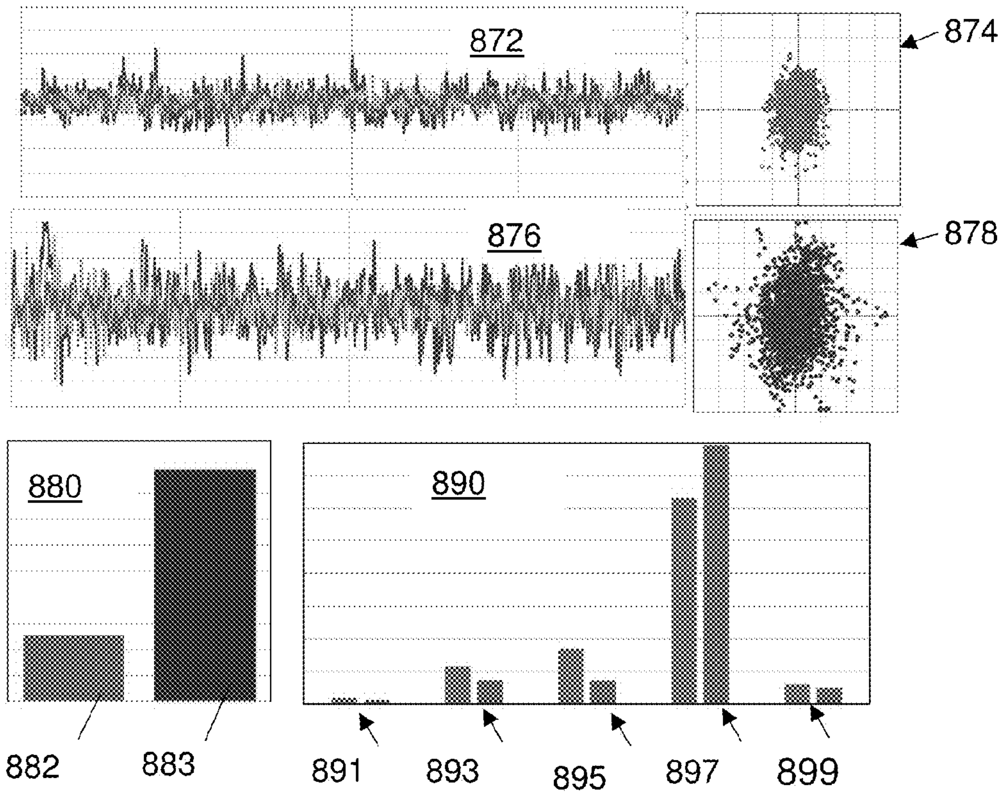

FIG. 8C shows the data from a 79-year-old male participant reported falling multiple times in the previous 6 months. Graph 872 shows the PHYBRATA time series data for a test with the participant's eyes open. The red line shows acceleration along the x-axis, the green line shows acceleration along the y-axis, and the blue line shows acceleration along the x-axis. Scatter plot 874 shows anteroposterior (AP) acceleration (y-axis) vs mediolateral (ML) acceleration (x-axis) based on the data from graph 872. Graph 876 shows the PHYBRATA time series data for a test with the participant's eyes closed. The red line shows acceleration along the x-axis, the green line shows acceleration along the y-axis, and the blue line shows acceleration along the x-axis. Scatter plot 878 shows AP/ML acceleration based on the data from graph 878. Note that the AP/ML data in both scatter plots 874, 878 is much more scattered for this participant than it was for the 51-year-old participant who reported no falls.

Graph 880 shows the PHYBRATA power for the two tests. The blue bar 882 (left) shows the power for the eyes open test and the red bar 883 (right) shows the power for the eyes closed test. The much higher value of Ec PHYBRATA power (Ec>0.89 watts) indicates impaired balance and high fall risk. The elevated ratio Ec/Eo>2 indicates impaired vestibular function. Both behaviors were representative of the group that reported multiple falls in the previous 6 months.

Graph 890 shows the results of analyzing the PHYBRATA frequency data to identify contributions to balance from various body systems. The blue bars (left) show data for eyes open, and the red bars (right) show data for eyes closed. Bars 891 show the balance contribution from the visual system, bars 893 show the balance contribution from the vestibular system, bars 895 show the balance contribution from the central nervous system, bars 897 show the balance contribution from proprioceptive systems, and bars 899 show the contribution from the VCR system.

Figure 9:
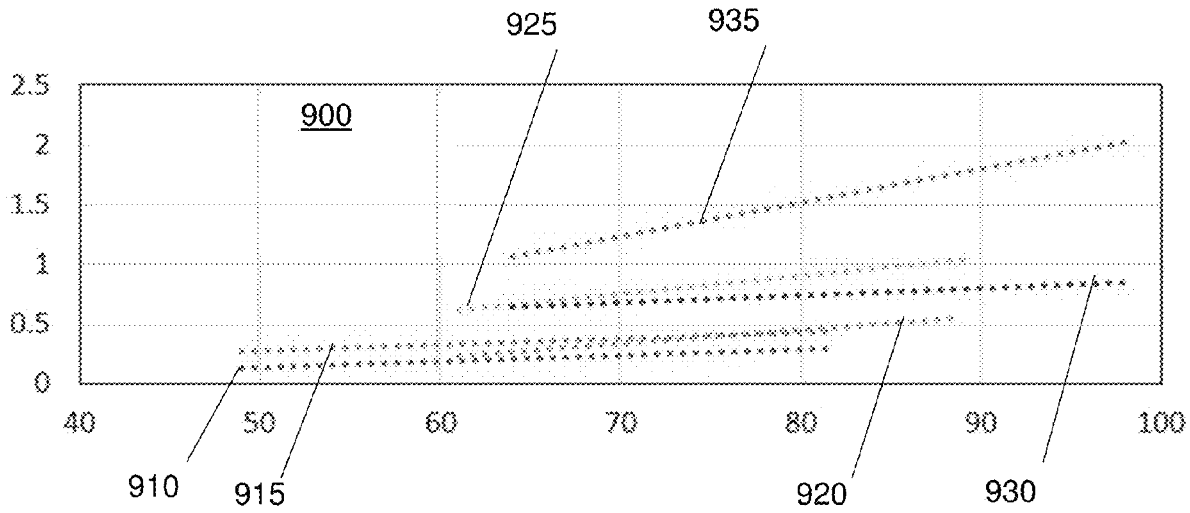
FIG. 9 is a graph showing how PHYBRATA data demonstrates progressive degradation of postural stability with age and increasing number of risk factors.

FIG. 9 is a graph 900 showing how PHYBRATA data demonstrates progressive degradation of postural stability with age and increasing number of risk factors. The x-axis is age, and the y-axis is sway power (i.e. PHYBRATA power). Lines 910 and 915 plot the sway data with eyes open and eyes closed, respectively, from those participants that had no risk factors. Lines 920 and 925 plot the sway data with eyes open and eyes closed, respectively, from those participants that had a single risk factor, and lines 930 and 935 plot the sway data with eyes open and eyes closed, respectively, from those participants that had two or more risk factors. While postural stability increases with age in all cases, it can easily be seen that risk factors have an even greater impact than age.

Figure 10:
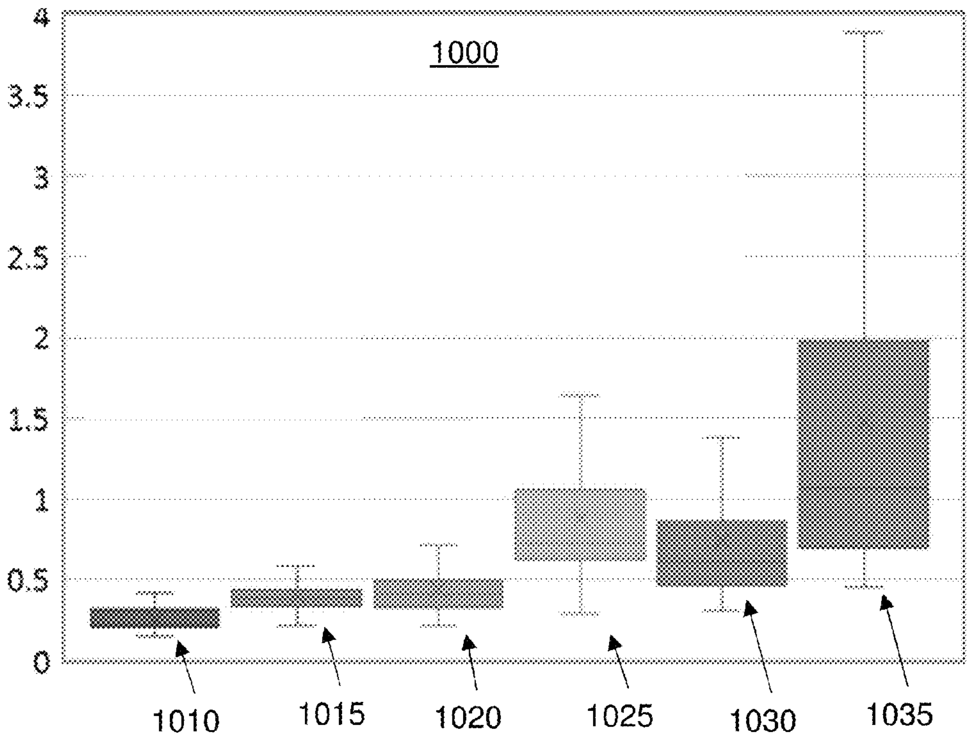
FIG. 10 is a graph showing how risk factors impact PHYBRATA data.

FIG. 10 is a graph 1000 showing how risk factors impact PHYBRATA data. Again, the y-axis is sway power, and the various candlesticks show the distribution of sway power data. The box charts 1010 and 1015 respectively show the eyes open and eyes closed distribution of sway power for participants with no risk factors, and the box charts 1020 and 1025 respectively show the eyes open and eyes closed distribution of sway power for participants with a single risk factor. The box charts 1030 and 1035 respectively show the eyes open and eyes closed distribution of sway power for participants with multiple risk factors.

Figure 11:
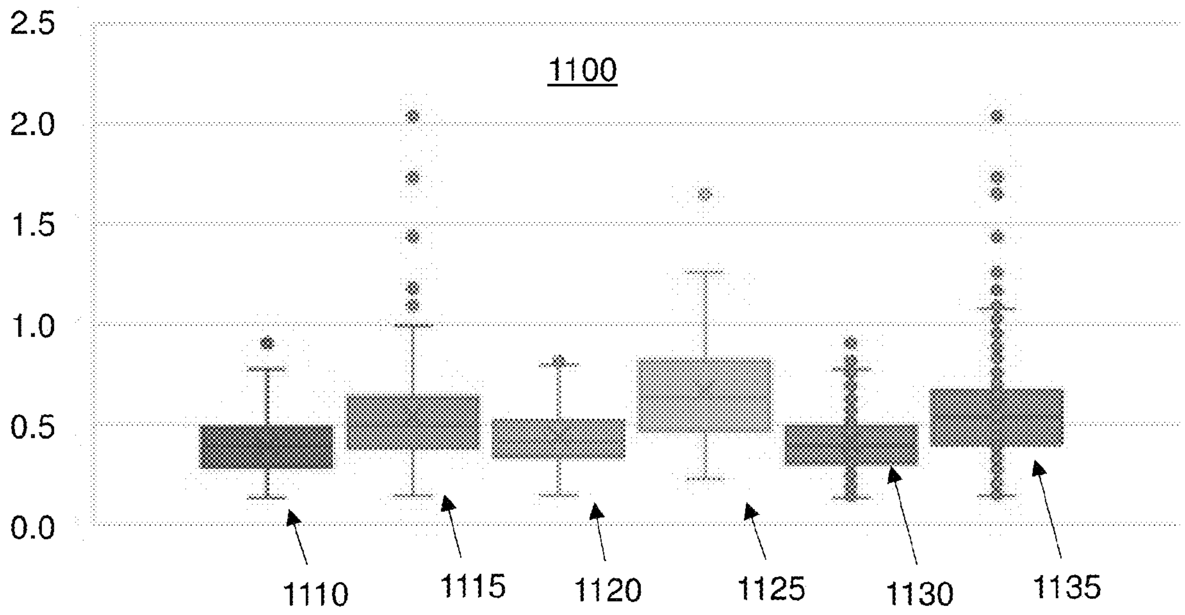
FIG. 11 shows box plots summarizing PHYBRATA performance for female vs. male participants and for those with falls and no falls.
Figure 11:
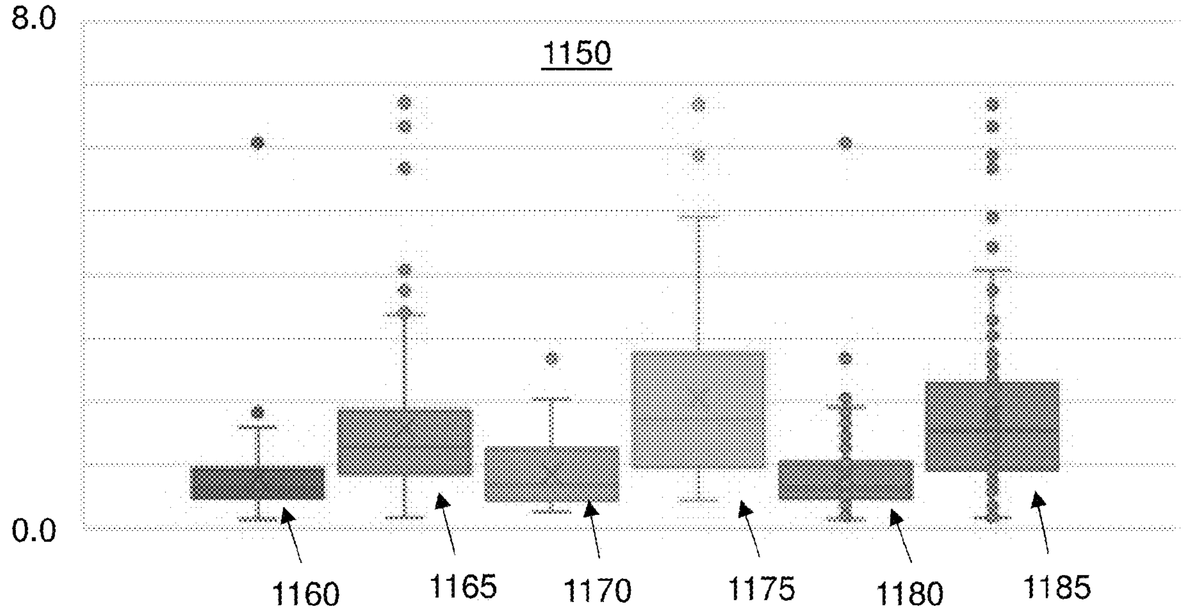

FIG. 11 includes a graph 1100 summarizing PHYBRATA performance for female vs. male participants for those with no falls and a graph 1150 summarizing PHYBRATA performance for female vs. male participants for those with falls. PHYBRATA power (i.e., sway power) is the y-axis in both graphs 1100, 1150.

Box plot 1110 shows eyes open data for females with no falls and box plot 1115 shows eyes closed data for the same group. Box plot 1120 shows eyes open data for males with no falls and box plot 1125 shows eyes closed data for the same group. Box plot 1130 shows eyes open data for all 239 participants with no falls and box plot 1135 shows eyes closed data for all participants with no falls.

Box plot 1160 shows eyes open data for females with at least one fall and box plot 1165 shows eyes closed data for the same group. Box plot 1170 shows eyes open data for males that had fallen and box plot 1175 shows eyes closed data for the same group. Box plot 1180 shows eyes open data for all 146 participants that reported at least one fall and box plot 1185 shows eyes closed data for all participants that had fallen.

PHYBRATA power demonstrates a strong statistical correlation with both different balance impairment thresholds for female vs. male participants: $F(1,237)=14.73$, $p=0.0002$; and retrospective incidence of falls within previous six months: $F(1,383)=307.99$, $p<0.00001$.

Figure 12:
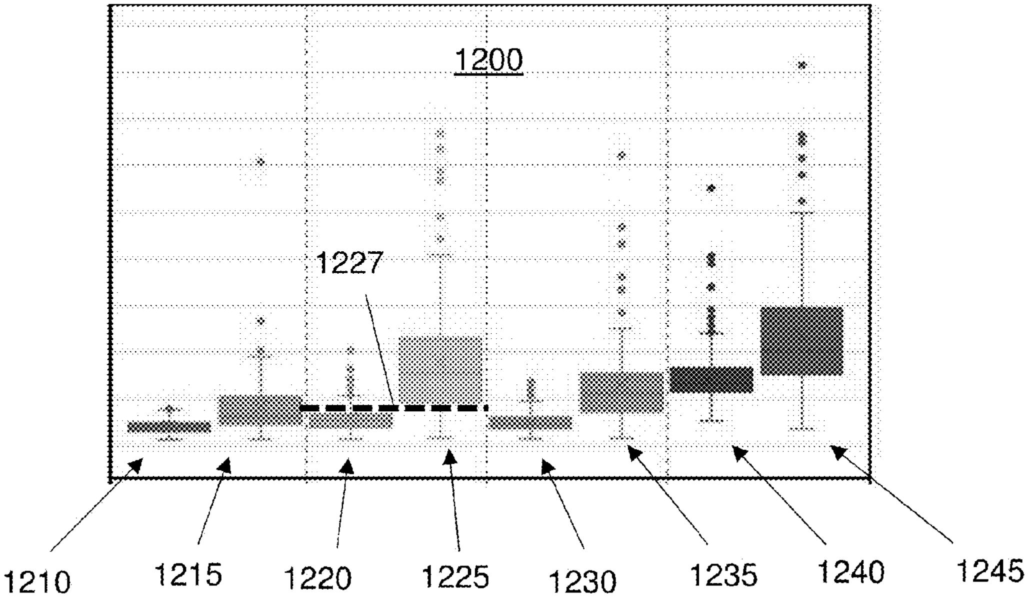
FIG. 12 shows box plots of 4 candidate PHYBRATA fall risk biomarkers.

FIG. 12 is a graph 1200 showing box plots of 4 candidate PHYBRATA fall risk biomarkers for 239 participants with no reported falls (NF) and 126 participants with one or more reported falls (RF). and a simple ratio for the rightmost half of the box charts.

The first two box plots show eyes open PHYBRATA data 1210 for the participants that reported no falls and PHYBRATA data 1215 for the participants that reported having fallen. The next two box plots show eyes closed PHYBRATA data 1220 for the participants that reported no falls and PHYBRATA data 1225 for the participants that reported having fallen. Note that line 1227 can provide a basic cutoff between fallers and non-fallers for the eyes closed PHYBRATA data at a PHYBRATA power of about 0.89 Watts (W). Box plots show the average of eyes open and eyes closed PHYBRATA data 1230 for the participants that reported no falls and the average of eyes open and eyes closed PHYBRATA data 1235 for the participants that reported having fallen. The y-axis is PHYBRATA power for these box charts.

The rightmost two box plots show a ratio of eyes closed PHYBRATA data to eyes open PHYBRATA data (Ec/Eo). Box chart 1240 shows the ratios for the participants that reported no falls and box chart 1245 shows the ratios for the participants that reported having fallen. The y-axis is simply the numerical ratio for these box plots.

Figure 13:
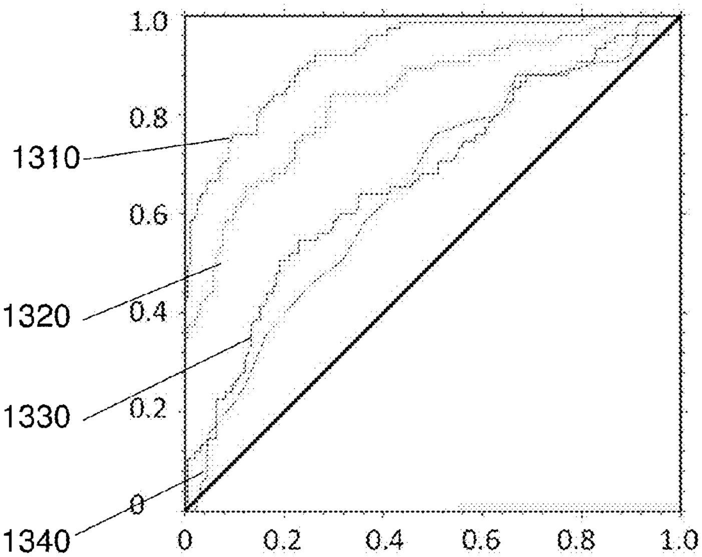
FIG. 13 shows receiver operating characteristic (ROC) curves comparing the performance of PHYBRATA biomarkers, TUG testing, and age for the diagnosis of fall risks.

FIG. 13 shows receiver operating characteristic (ROC) curves comparing the performance of PHYBRATA biomarkers for eyes closed data 1310, PHYBRATA biomarkers for eyes open testing 1320, timed up and go (TUG) testing 1330, and age for the diagnosis of fall risks 1340. The eyes closed curve has an area under curve (AUC) of 0.92, a sensitivity of 0.82 and specificity of 0.92, showing that it is an effective classifier for fall risk. The ROC curves indicate that the eyes-closed PHYBRATA power (Ec) significantly out-performed TUG testing in identifying participants who reported one or more falls in the previous six months and may be utilized as a biomarker to support clinical diagnosis of fall risk.

Figure 14:
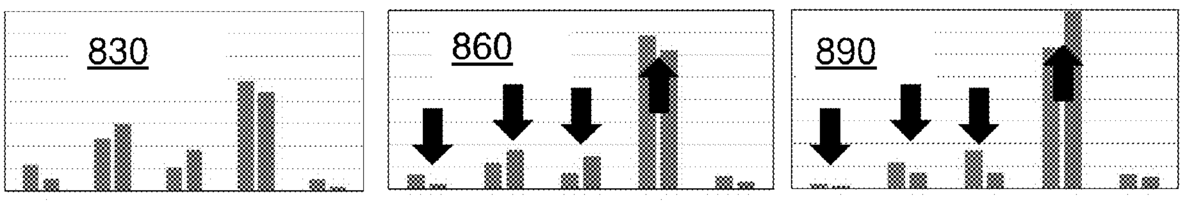
FIG. 14 shows PHYBRATA spectral analyses of sensory reweighting across multiple physiological systems that accompany age-related balance degradation and increasing fall risks.

FIG. 14 shows PHYBRATA spectral analyses of sensory reweighting across multiple physiological systems that accompany age-related balance degradation and increasing fall risks. The sensory reweighting data 830 from FIG. 8A from a 51-year-old woman who did not report any falls, sensory reweighting data 860 from an 89-year-old woman who reported falling once, and sensory reweighting data 890 from a 79-year-old man who reported falling multiple times is copied into FIG. 14. Comparing the data from the non-faller 830 to the fallers 860, 890, it can be seen visual contribution, the vestibular contribution and the central nervous system contribution all are progressively lower as the incidence of falls increases and the contribution from the proprioceptive system is progressively higher. PHYBRATA spectral analyses demonstrates utility for quantifying sensory reweighting and impairments across multiple physiological systems that accompany age-related balance degradation and increasing fall risks, as well as for subsequent monitoring of improvements throughout treatment and rehabilitation.

The results described above and illustrated in the figures demonstrate that PHYBRATA testing enables objective assessment of fall risks in older populations and provides an important adjunct to standard balance and gait testing to assess underlying physiological contributions to balance impairments and to support targeted rehabilitation strategies.

FIG. 15 through FIG. 21 present results of another study that was performed using 131 participants who were able to successfully complete balance testing in a PHYBRATA fall risk study carried out in a senior living residence. Of the 131 participants, 85 were female and 46 were male. Based on previous correlations of balance performance and fall risk using the Ec PHYBRATA biomarker, 78 participants qualified as low fall risk, while 53 qualified as high fall risk. 8 participants reported 0 hours/week of exercise, 55 reported 1-4 hours/week, and 68 reported five or more hours/week.

Figure 15:
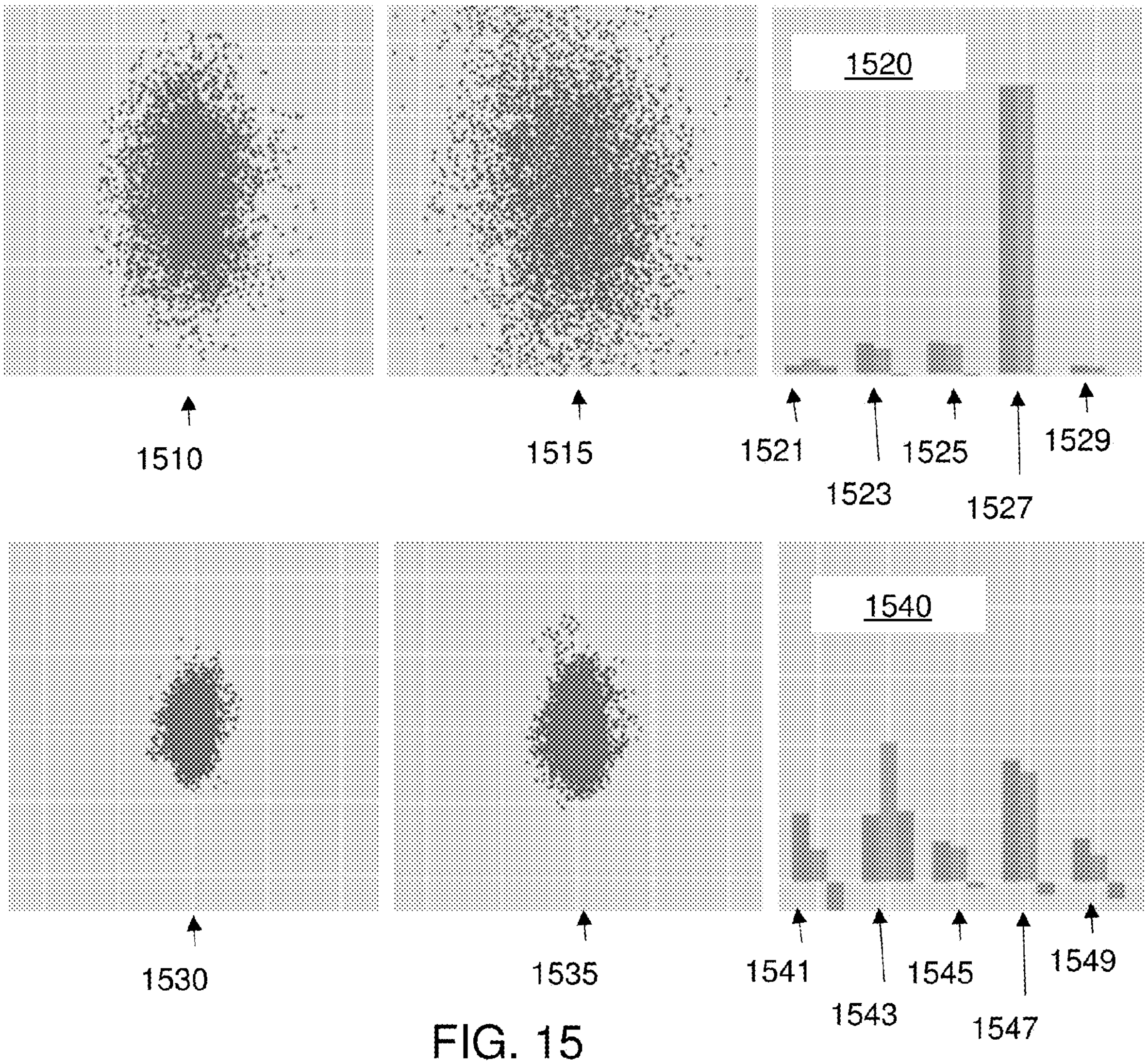
FIG. 15 presents typical results from the balance testing of participants in a study.

FIG. 15 presents typical results from the balance testing of the 131 participants described above. The top row presents data from a member of the high fall risk group, and the bottom row presents data from a member of the low fall risk group. The scatter plots demonstrate that participants are less stable with their eyes closed (Ec) 1515, 1535 as compared to eyes open (Eo) 1510, 1530, as expected. They also reveal that high fall risk participants (the first row) are significantly less stable than low fall risk participants (the second row). The sensory reweighting bar charts, upper bar chart 1520 for the high fall risk participant and lower bar chart 1540 for the low fall risk participant, show eyes open data in blue (on left in each group of bars), eyes closed data in green (middle), and Ec-Eo in red (right). Each bar chart 1520, 1540 includes visual contribution 1521, 1541, vestibular contribution 1523, 1543, CNS contribution 1525, 1545, proprioceptive contribution 1527, 1547, and VCR contribution 1529, 1549. The charts 1520, 1540 reveal that the vestibular contribution 1523 to balance control is much lower for both Eo and Ec for high fall risk participants compared to the vestibular contribution 1543 for low fall risk participants. High fall risk participants compensate for this loss of vestibular function by relying more heavily on proprioceptive balance control 1527, which contributes to declining postural stability as we age, since the reliability of proprioceptive inputs can also degrade with age due to loss of muscle mass and lower limb strength, peripheral neuropathies, or reduced proprioceptive acuity in the feet and ankles. As this degraded proprioception becomes the "dominant" system, balance recovery strategies (e.g., quick stepping or ankle adjustments) lose effectiveness. Reduced vestibular input and overreliance on proprioception can trigger a spiral of decline in balance and mobility, which also impacts cognitive function and psychological well-being, as follows:

Reduced vestibular function can lead to increased reliance on proprioception which can lead to poorer balance and gait, especially in challenging environments. This can lead to reduced mobility and physical activity leading to deconditioning of gait and postural muscles which can further increase fall risk. Fear of falling further reduces balance and mobility confidence which can increase cognitive load to support balance and decreased cognitive reservoir for other functions. This can lead to reduced social activity and a decline in cognitive performance and psychological well-being.

Figure 16:
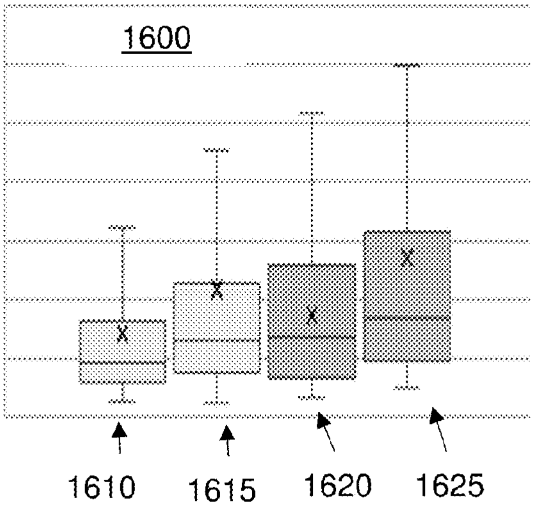
FIG. 16 summarizes the balance results for participants in the study, divided into groups of those who had fallen within the last 6 months and those who had not.

FIG. 16 summarizes the balance results for all 131 participants of the study, divided into groups of those who were classified as high fall risk vs. low fall risk based on their Ec PHYBRATA powers, with the y-axis being balance instability. Box chart 1610 represents the eyes open (Eo) data for the 78 low fall risk participants and box chart 1615 represents the eyes closed (Ec) data for those participants. Box chart 1620 represents the Eo data for the 53 high fall risk participants and box chart 1625 represents the Ec data for those participants. This data again reveals that the participants are less stable with their eyes closed (Ec) as compared to eyes open (Eo), and that participants who reported falls were markedly less stable than the no-fallers, both with Eo and with Ec.

Figure 17:
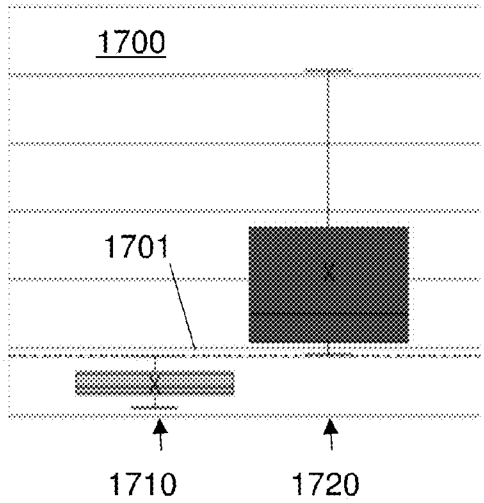
FIG. 17 show eyes closed data for the participants of the study, divided into low fall risk and high fall risk groups.

FIG. 17 shows eyes closed data for the participants of the study, divided into low fall risk and high fall risk groups, with the y-axis being balance instability. Box chart 1710 shows Ec data for the 78 low fall risk participants and box chart 1720 shows Ec data for the 53 high fall risk participants. The 0.89 biomarker 1701 is shown as a red broken line. The chart 1700 highlights how much more stable and tightly clustered the Ec balance performance is for the 78 low fall risk participants vs. the 53 high fall risk participants.

Figure 18:
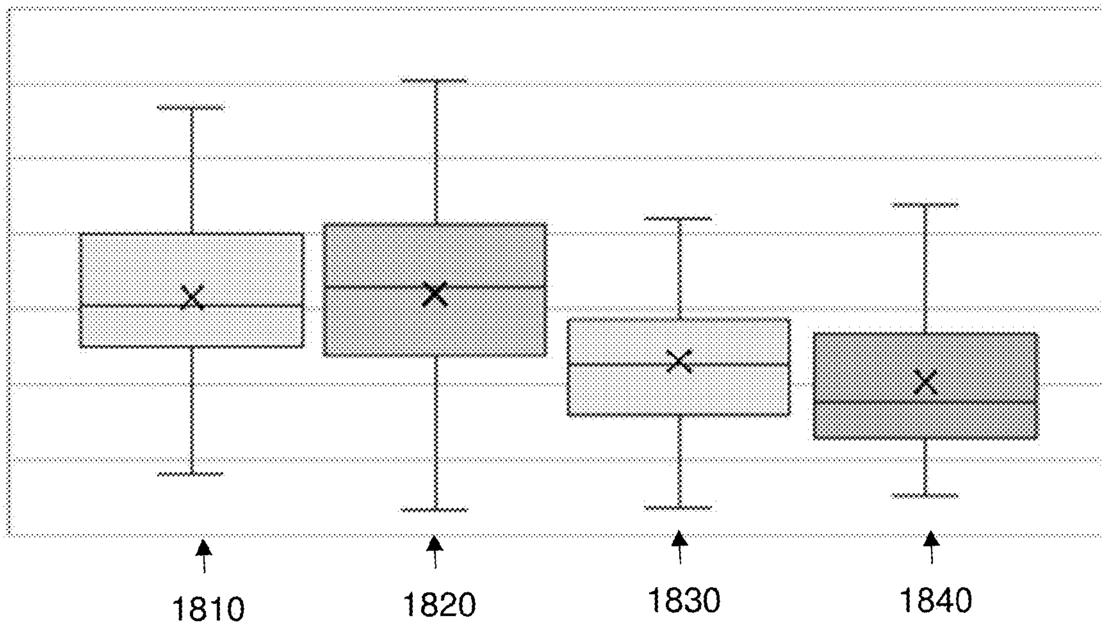
FIG. 18 presents the vestibular contribution to balance control for the participants of the study, divided into low fall risk and high fall risk groups.

FIG. 18 presents the vestibular contribution to balance control for the participants of the study, with the y-axis being the percentage of vestibular balance control contribution, with a range of 0% to 70% shown. The vestibular balance contribution was calculated by extracting the 0.1-0.5 Hz data from the frequency domain data. Box chart 1810 shows Eo data and box chart 1820 shows the Ec data for the low fall risk group. Box chart 1830 shows Eo data and box chart 1840 shows the Ec data for the high fall risk group. Thus, vestibular balance contribution for both Eo and Ec with the 78 low fall risk participants is greater than for the 53 high fall risk participants. There is also a trend for vestibular control to increase when low fall risk participants close their eyes, but for vestibular control to decrease when high fall risk participants close their eyes.

Figure 19:
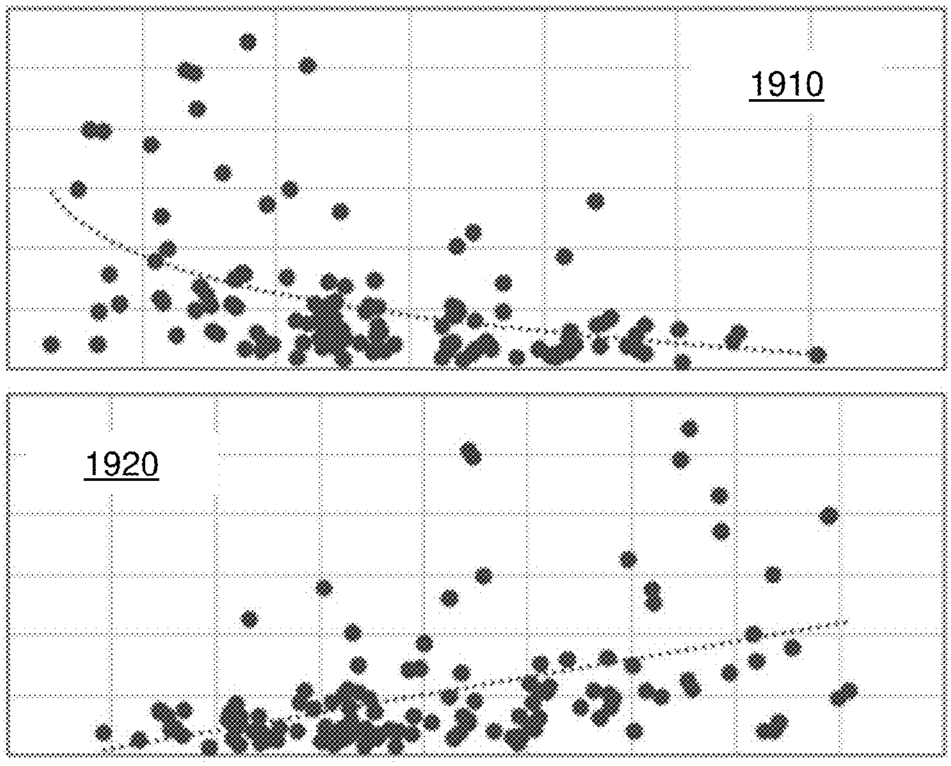
FIG. 19 illustrates that greater balance instability is accompanied by lower levels of vestibular control and a greater reliance on proprioceptive control.

FIG. 19 illustrates that greater balance instability is accompanied by lower levels of vestibular control and a greater reliance on proprioceptive control. Graph 1910 shows overall Ec balance instability (y-axis) as a function of normalized Ec vestibular contribution (x-axis) for each of the 131 participants in the study. It clearly shows an inverse relationship between the two, so that as Ec vestibular contribution increases, the participant has better balance.

Conversely, graph 1920 shows that overall Ec balance instability (y-axis) increases as normalized Ec proprioceptive contribution (x-axis) increases.

Figure 20:
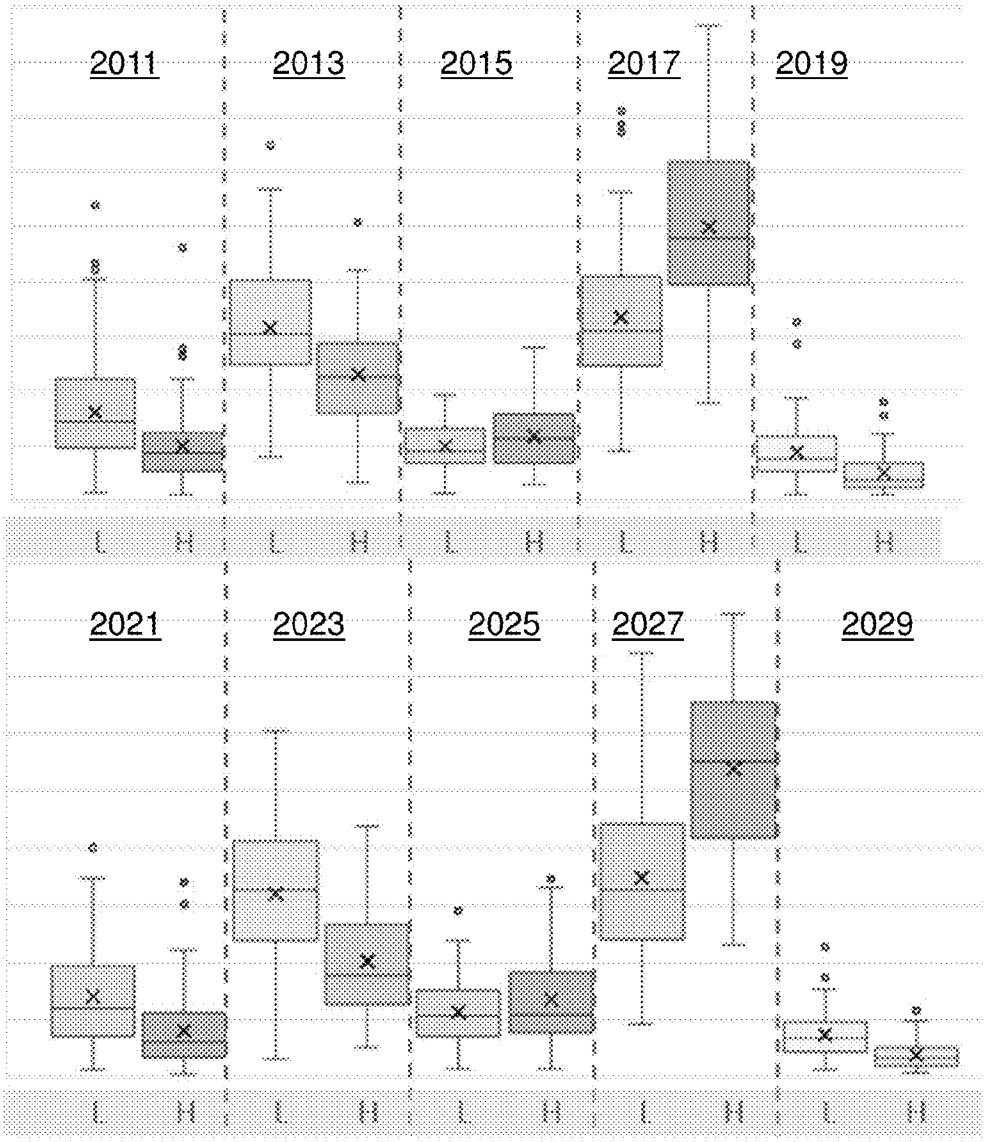
FIG. 20 shows sensory reweighting data for the low and high fall risk participants of the study.

FIG. 20 shows sensory reweighting data for the low and high fall risk participants of the study. The upper graph shows Eo data, and the lower graph shows Ec data with each set of data having one box chart for low fall risk participants on the left, and high fall risk participants on the right. Box charts 2011, 2021 show normalized vision balance contribution, box charts 2013, 2023 show normalized vestibular balance contribution, box charts 2015, 2025 show normalized CNS balance contribution, box charts 2017, 2027 show normalized proprioceptive balance contribution, and box charts 2019, 2029 show normalized VCR balance contribution. The data in FIG. 20 again illustrate that low fall risk participants have a greater vestibular contribution to balance control and less reliance on proprioception, whereas high fall risk participants have reduced vestibular contribution to balance control and greater reliance on proprioception.

Figure 21:
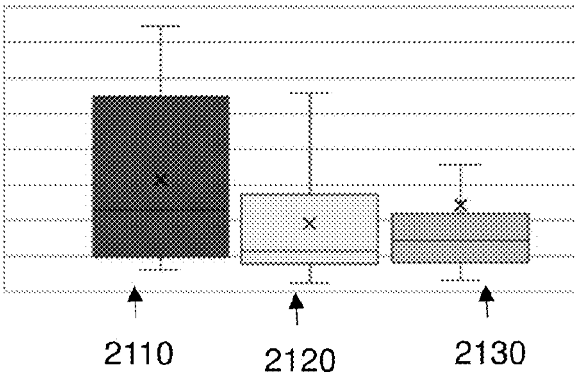
FIG. 21 shows balance instability data for participants with different amounts of regular exercise.

FIG. 21 shows balance instability data (y-axis) for participants with different amounts of regular exercise. Bar chart 2110 shows Ec balance instability data for the participants that reported getting no regular exercise. Box chart 2120 shows Ec balance instability data for the participants that reported getting 1-5 hours of exercise per week, and box chart 2130 shows Ec balance instability data for the participants that reported getting more than hours of exercise per week. This data reveals a dramatic relationship between the amount of exercise reported by the participants and their degree of balance instability as measured using PHYBRATA biomarkers.

The data in FIG. 15 through FIG. 21 demonstrate that PHYBRATA biomarkers quantify each individual's unique neuromotor systems impairment profile and related fall risk, including any impairments to sensory inputs (visual, vestibular, proprioceptive), CNS sensorimotor integration, or motor control such as the vestibulocollic reflex (VCR). PHYBRATA biomarkers can serve as:

- Physiological biomarkers that assess critical neuromotor and cognitive functions related to aging.
- Systems aging biomarkers that identify patterns and pathways in the systemic aging and dysfunctions of the body's integrated neuromotor system.
- Longitudinal and clinical biomarkers of aging provide insights into the progression of neuromotor aging processes by monitoring individuals over extended periods, allowing researchers to predict health outcomes, understand the dynamics of aging, and develop targeted and personalized bioelectronic interventions to promote healthy neuromotor aging.

The most widely accepted method to quantitatively assess an individual's ability to use visual, proprioceptive and vestibular cues to maintain postural stability during standing balance is the sensory organization test (SOT). The SOT uses a sophisticated six-degree-of-freedom CDP motion platform with dual force plates and a wrap-around visual screen to measure changes in a person's balance ability when different combinations of visual, vestibular, and proprioceptive sensory systems are either available or disrupted. Test results include separate scores averaged over three trials of six different SOT conditions, along with an overall equilibrium index score. Multiple studies have used SOT to quantify overall balance decline, underlying sensory system impairments, and fall risk in older population. SOT results from a cohort of 34 older adults comparing those with and without elevated fall risks demonstrate qualitative trends similar to those shown here, with elevated fall risk participants recording lower overall equilibrium index scores, lower sensory analysis scores for vestibular and visual function, and higher sensory analysis score for proprioception. ROC curves using the SOT composite score to predict fall risk had an AUC of 0.65, typical of the values ranging from 0.5-0.7 that have been reported for many other common fall risk assessments, and much lower than the PHYBRATA Ec results disclosed in FIG. 13, with AUC=0.92. Other SOT studies of balance in older populations consistently report lower overall equilibrium index scores and lower sensory analysis scores for vestibular function. The results disclosed here are the first to demonstrate clear progressive trends in declining balance performance and sensory reweighting, with decreased vestibular function offset by greater reliance on proprioception, across a large cross-sectional study cohort spanning a wide range of age and balance performance. Compared with SOT, PHYBRATA testing can be completed with much shorter test times and far less complex and expensive apparatus. The portability and ease of use of the PHYBRATA sensor eliminates the need for participants to come to a dedicated balance testing facility.

The PHYBRATA sensor exploits the fact that the head serves as an egocentric reference for balance, walking, and most other voluntary motor activities and centralizes the integrated sensing of physiological signals. Maintaining the biomechanical stability of the head and eyes is thus a fundamental goal of human balance and postural stability control. During quiet stance, body motion increases in order of lower limbs, pelvis, trunk, and head, exhibiting frequency components up to 30 Hz at the head due to head-neck stabilization via vestibulocollic reflexes. Direct measurement of head acceleration has been shown to provide much more sensitive detection of body motion across this entire frequency range than is possible using center of pressure (COP) measurements with force plates and CDP systems. Acceleration spectral density (ASD) is a widely used engineering tool for analyzing random vibrations in complex industrial systems, including the design of robots that can mimic human bipedal motion. Physiological vibration has been shown to be inherent to human postural and motor control including components described as tremor, rambling and trembling, and head micro-movements. Ensemble-average ASD analyses have been utilized to capture the significant time varying spectral changes that result from intermittent balance control processes that utilize multiple physiological system inputs and outputs, and to identify statistically significant spectral features that can distinguish patients vs. control groups. In clinical medicine, head-mounted accelerometers have been used to compare normal and pathological passive head acceleration spectra for healthy individuals and those with essential tremor, to compare head and eye tremors for the assessment of vestibulo-ocular impairments, to detect changes in intercranial pulsatility associated with diffuse brain tissue atrophy and white matter degeneration following stroke, and to measure the mechanocardiographic motion of the body resulting from cardiovascular blood flow. Analysis of head micro-movements in MRI image data has been used to classify different neurodevelopmental disorder phenotypes. Acceleration spectral analysis of body center of mass data has also been utilized to study differences in the complex multi-system postural control process between young children and adults.

Changes in the spectral characteristics of postural control have been observed for many different postural challenges and medical conditions. Age-related changes in specific frequency bands have been observed, and analysis of these spectral characteristics during quiet stance may be a clinically useful tool in identifying biomarkers associated with age-related loss of functional balance capacity and increasing fall risk. Spectral analysis of postural sway, sensory impairments, and sensory reweighting due to a wide range of postural challenges and medical conditions reveals that specific frequency bands correspond to distinct postural regulation strategies. The present disclosure validates the clinical utility of digital biomarkers derived from PHYBRATA ASD analyses to enable rapid objective assessment of progressive age-related balance impairments, sensory reweighting, and the underlying physiological contributions.

PHYBRATA testing can also quantify changes in postural stability and sensory reweighting due to various postural stability challenges. Case study data is presented herein in FIG. 22 through FIG. 25 for a 63-year-old male with no diagnosed sensory or motor impairments. Standing balance tests were carried out using a head-mounted PHYBRATA sensor. PHYBRATA time series data and spatial scatter plots, eyes open (Eo) and eyes closed (Ec) PHYBRATA powers, Ec/Eo PHYBRATA power ratio, and time-resolved PHYBRATA power spectral density (PSD) distributions are compared for three different postural stability challenges: eyes open vs. eyes closed; feet apart vs. feet together; standing on hard floor vs. foam pad.

Figure 22:
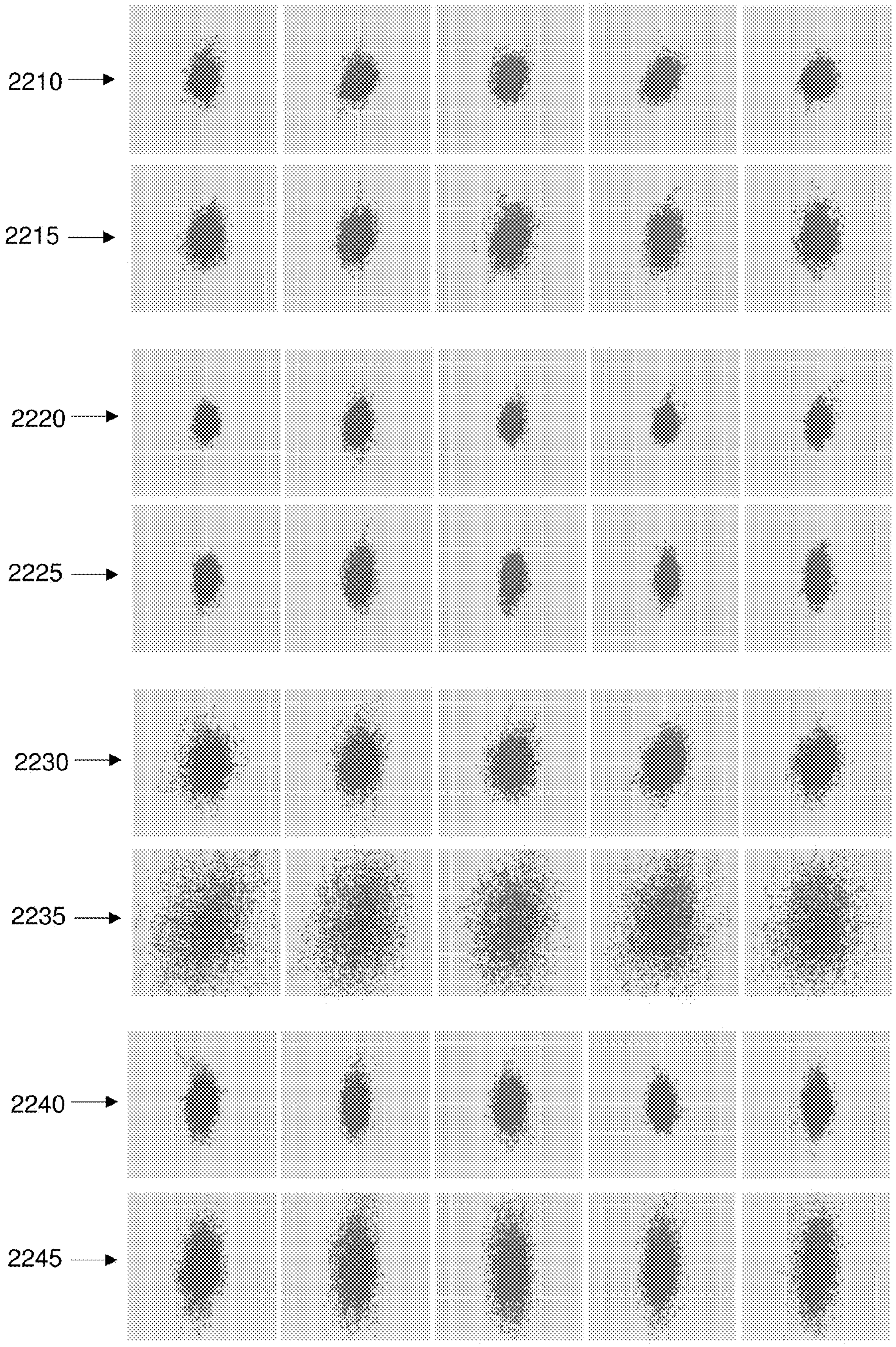
FIG. 22 shows anterior-posterior (AP) vs mediolateral (ML) PHYBRATA acceleration scatter plots a variety of 60 second trials.

FIG. 22 shows anterior-posterior (AP) vs mediolateral (ML) PHYBRATA acceleration scatter plots a variety of 60 second trials. This is essentially a view down on the top of the head showing all of the microscopic front-to-back and side-to-side motion of the body that happens while the test subject tries to stand still. The anterior-posterior (AP) vs. mediolateral (ML) PHYBRATA acceleration scatter plots for five 60 sec Eo, 60 sec Ec trials with feet together on hard floor are shown in the first two rows. The plots in row 2210 were taken with the person's feet together standing on a hard floor with their eyes open and those in 2215 were taken under the same conditions with the person's eyes closed. The trials alternated eyes open and then eyes closed for 60 seconds each. The plots in row 2220 and row 2225 were taken with feet apart on a hard floor and respectively show AP vs. ML PHYBRATA acceleration scatter plots for five 60 sec Eo trials (row 2220), and five 60 sec Ec trials (row 2225). Row 2230 and row 2235 respectively show AP vs. ML PHYBRATA acceleration scatter plots for five 60 sec Eo, 60 sec Ec trials with feet together on a balance pad (e.g., a squishy foam pad). Row 2240 and row 2245 respectively show AP vs. ML PHYBRATA acceleration scatter plots for five 60 sec Eo, 60 sec Ec trials with feet apart on a balance pad. The test subject's balance is far less stable on the balance pad than on a hard floor, for both Eo and Ec, and the difference between eyes open and eyes closed is even more pronounced. With eyes closed on the balance pad the brain has been deprived of reliable inputs from both the visual and proprioceptive sensory systems, which reveals how well the postural control process functions when relying predominantly on the vestibular system alone.

Figure 23:
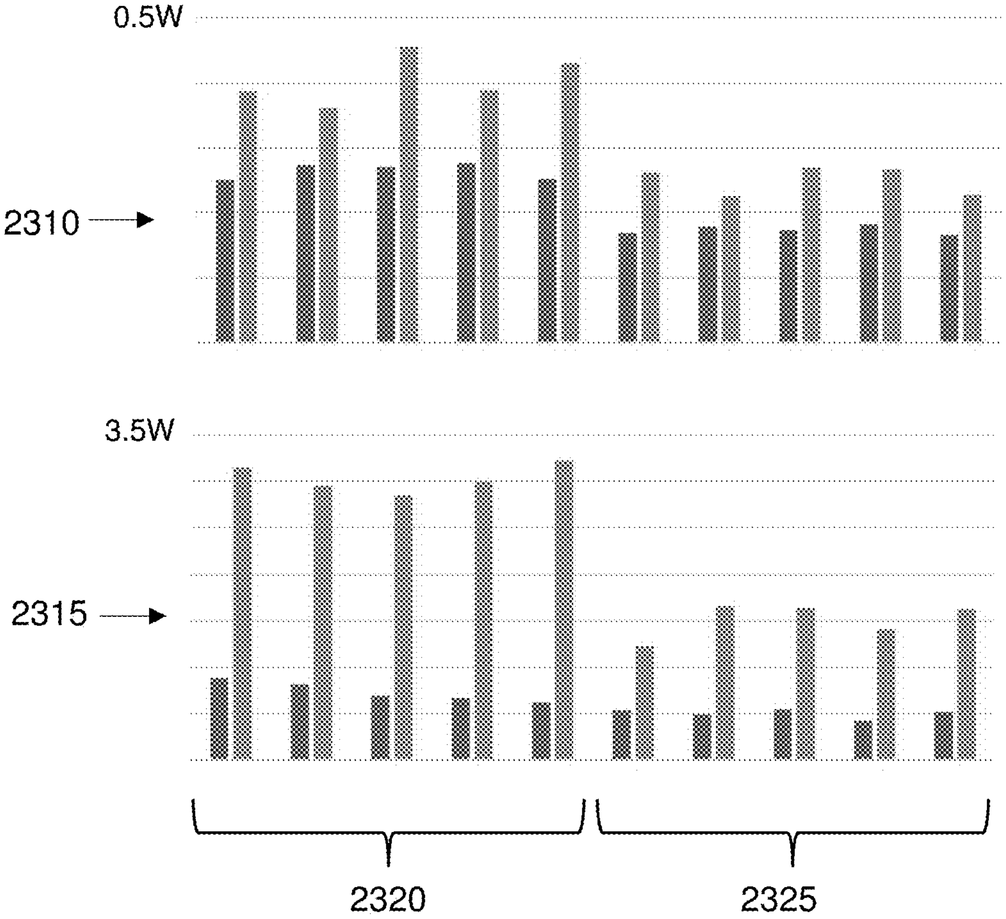
FIG. 23 shows PHYBRATA power vs. postural stability challenges.

FIG. 23 presents PHYBRATA power for the four series of tests shown in FIG. 22, demonstrating degraded postural stability for all three postural stability challenges: Ec vs. Eo, feet together vs. feet apart, and foam pad vs. hard floor. The blue bars represent trials with eyes open, and the orange bars represent trials with eyes closed. The upper bar graph 2310 shows the tests performed on a hard floor and the lower bar graph 2315 shows the tests performed on a balance pad. Note that the maximum power level in graph 2315 is 7 times as much as the maximum power level of graph 2310. The first 5 sets of bars 2320 for each graph 2310, 2315 represent trials with feet together, and the second 5 sets of bars 2325 for each graph 2310, 2315 represent trials with feet apart.

It is easily seen that the test subject's balance is far less stable on the foam pad (as shown in bar charts 2315) than on a hard floor (as shown in bar charts 2310), for both eyes open and eyes closed, and the difference between eyes open and eyes closed is even more pronounced when on the foam pad. With eyes closed on the foam pad the brain has been deprived of reliable inputs from both the visual and proprioceptive sensory systems, which reveals how well the postural control process functions when relying predominantly on the vestibular system alone.

Figure 24:
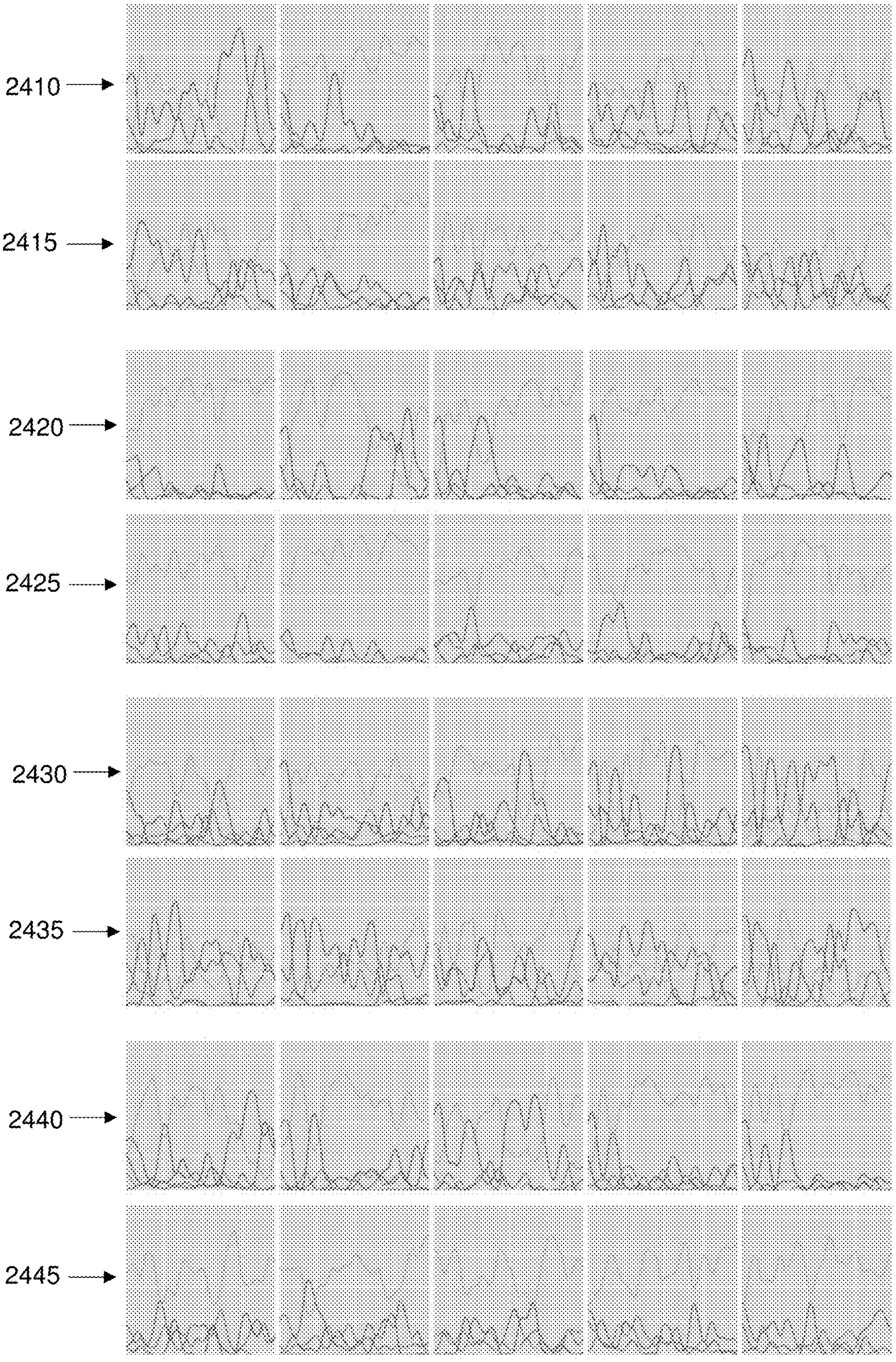
FIG. 24 shows anterior-posterior (AP) vs mediolateral (ML) PHYBRATA sensory reweighting profiles as a function of time for the trials of FIG. 22.

PHYBRATA spectral analyses demonstrates utility for quantifying the unique sensory reweighting profiles across multiple physiological systems that contribute to degraded postural stability for each of the three different postural stability challenges. FIG. 24 shows time-resolved PHYBRATA sensory reweighting profiles based on the data shown in FIG. 22. The graphs in FIG. 24 show visual system data in blue, proprioceptive data in yellow, vestibular data in red, central nervous control data in green, and VCR data in blue with the x-axis representing a percentage contribution and the y-axis being time through each 60 second trial.

Row 2410 shows the sensory reweighting profiles for the trials conducted with eyes open and feet together on a hard floor and row 2415 shows the sensory reweighting profiles for the trials conducted with eyes closed and feet together on a hard floor. Row 2420 shows the sensory reweighting profiles for the trials conducted with eyes open and feet apart on a hard floor and row 2425 shows the sensory reweighting profiles for the trials conducted with eyes closed and feet apart on a hard floor. Row 2430 shows the sensory reweighting profiles for the trials conducted with eyes open and feet together on a balance pad and row 2435 shows the sensory reweighting profiles for the trials conducted with eyes closed and feet together on a balance pad. Row 2440 shows the sensory reweighting profiles for the trials conducted with eyes open and feet apart on a balance pad and row 2445 shows the sensory reweighting profiles for the trials conducted with eyes closed and feet apart on a balance pad.

Closing the eyes while standing on the hard floor leads to a reduction in the use of the visual input for balance control and an increase in the use of vestibular and proprioceptive inputs. For this healthy individual, standing on the foam pad is accompanied by increased utilization of proprioceptive input for balance control and decreases in the use of vestibular and visual inputs.

Figure 25:
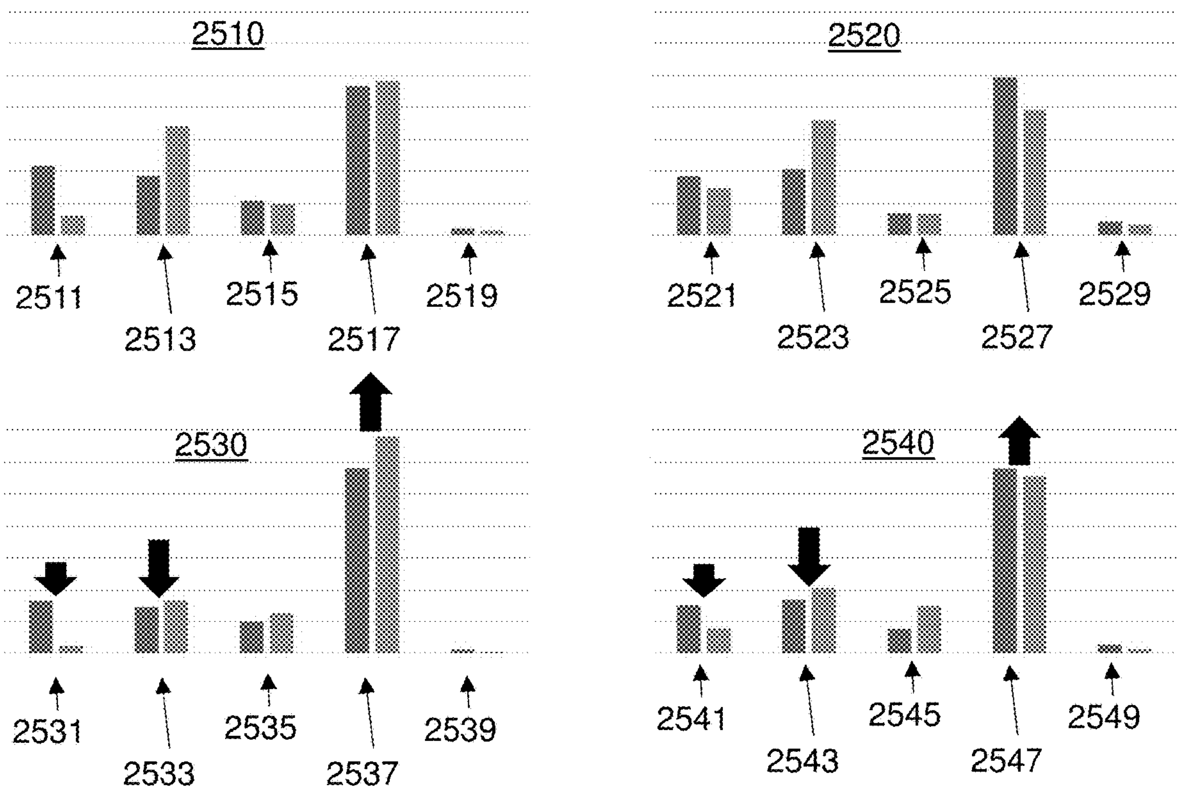
FIG. 25 shows sensory reweighting results from FIG. 24 averaged across all five trials.

FIG. 25 presents the sensory reweighting results from FIG. 24 averaged across all five trials, demonstrating that PHYBRATA sensor testing enables quantitative assessments of sensory reweighting due to postural stability challenges. Graph 2510 shows the averages of the trials with feet together on a hard floor (row 2410 and row 2415). The blue bars (on left for each set of bars) represent eyes open trials and the orange bars (on right for each set of bars) represent eyes closed trials. Bars 2511, 2521, 2531, 2541 show visual system contribution, bars 2513, 2523, 2533, 2543 show vestibular system contribution, bars 2515, 2525, 2535, 2545 show central nervous system contribution, bars 2517, 2527, 2537, 2547 show proprioceptive contribution, and bars 2519, 2529, 2539, 2549 show VCR contribution. Similarly, graph 2520 shows the averages of the trials with feet apart on a hard floor (row 2430 and row 2435), graph 2530 shows the averages of the trials with feet together on a foam pad (row 2420 and row 2425), and graph 2540 shows the averages of the trials with feet apart on a foam pad (row 2440 and row 2445). Note that when this healthy subject is standing on a foam balance pad, both with their feet together and with their feet apart, their reliance on proprioception increases and they rely less on visual and vestibular systems as compared to when they are standing on a hard floor. PHYBRATA spectral analyses demonstrates utility for quantifying the unique sensory reweighting profiles across multiple physiological systems that contribute to degraded postural stability for different postural stability challenges.

Involuntary head micro-movements such as those detected using the PHYBRATA sensor have recently been shown to reflect both age-dependent development and age-dependent decline in human motor stability across a very wide age range. These head micro-movements may serve as an important biomarker in diagnosing and treating older adults with balance impairments and children with developmental disorders. This phenomenon may enable the combination of PHYBRATA and NEURVESTA innovations to address such disorders.

Aging causes loss of the motion sensing cells in the vestibular organs 120, both the otolith organs that detect linear motion and the semicircular canals that detect rotational motion. Electrical Vestibular Stimulation, commonly referred to as "EVS", is a specialized form of transcranial electrical stimulation that can counteract the corresponding decreases in the signals generated by the vestibular organs, by restoring function within the peripheral vestibular organs, increasing the ability of the vestibular nerve to conduct the signals to the brain, and the ability of the corresponding neurosensory and neuromotor structures in the brain itself to process these signals and stabilize balance and movement. Many potential therapeutic applications of EVS have been demonstrated, including enhancement of vestibular rehab and reduction of balance and movement disruptions caused by aging, concussions, stroke, Parkinson's disease, central neuro-degenerative disorders, cerebral palsy in children, cybersickness during virtual reality (VR) exposure, and microgravity exposure during spaceflight. However, the effectiveness of EVS has also been shown to be variable, and not all choices of stimulation parameter are effective for improving postural control. The persistence of any therapeutic effects has also not been assessed.

Despite the many potential diagnostic and therapeutic applications that have been studied for EVS, it has not yet been widely commercialized because of the difficulties in assessing individual patient responses to the wide range of potential EVS stimulation parameters. The NEURVESTA system disclosed herein solves this problem by integrating several key innovations, including: wearable PHYBRATA sensing of neurophysiological impairments that disrupt balance; non-invasive, therapeutic neurostimulation to correct vestibular balance impairments; miniaturized neurostimulation electronics; machine learning models that allow therapeutic treatments to be individually tailored to each patient's unique impairment profile; and use of an accelerated aging model to study the development and correction of balance disruptions.

A unique capability of the NEURVESTA system is its ability to use the PHYBRATA sensor to quantify changes in postural stability and sensory reweighting during and following the application of EVS. This capability has been used to monitor how test subjects respond to a wide range of potential EVS waveforms and dosing regimens, which led to the discovery of the subthreshold wideband stochastic EVS (swsEVS) stimulation waveform and multi-session swsEVS treatment protocol disclosed in this patent that together activate long-lasting neuroplastic restoration of vestibular balance function and which are collectively referred to as vestibular stimulation therapy (VST).

Figure 26:
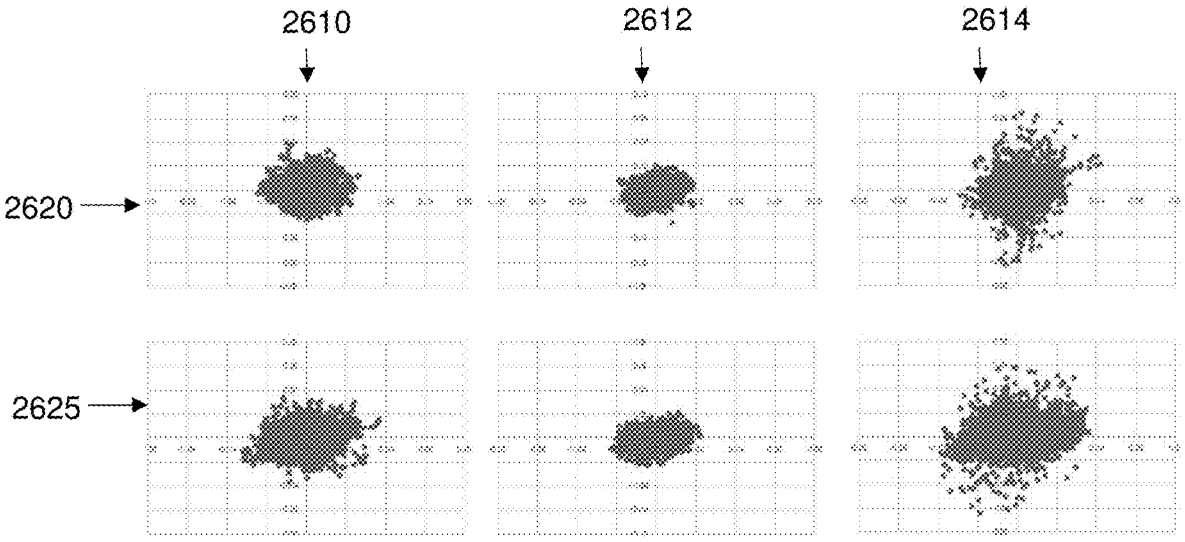
FIG. 26 shows scatter plots captured as a part of an example therapeutic screening.

FIG. 26 through FIG. 30 show examples of exploratory studies used to monitor how test subjects respond to a wide range of potential EVS waveforms, FIG. 26 shows PHYBRATA scatter plots for a test subject before applying EVS and during the application of EVS at two different current levels. The top row of scatter plots 2620 show data captured with the patient's eyes open, while the second row of scatter plots 2625 show data captured with the patient's eyes closed. The first column of scatter plots 2610 show baseline data with no EVS being administered. The middle column of scatter plots 2612 show data captured while an EVS waveform having a spectral content ranging from 0-25 Hz is administered at a level of 750 μA. It shows that the patient is responding well to the therapy with much less sway than compared to the baseline data 2610. The right column of scatter plots 2614 show data captured while an EVS waveform having a spectral content ranging from 0-25 Hz is administered at a level of 3000 μA. Note that the patient's balance is even worse than the baseline 2610 for this case.

Figure 27:
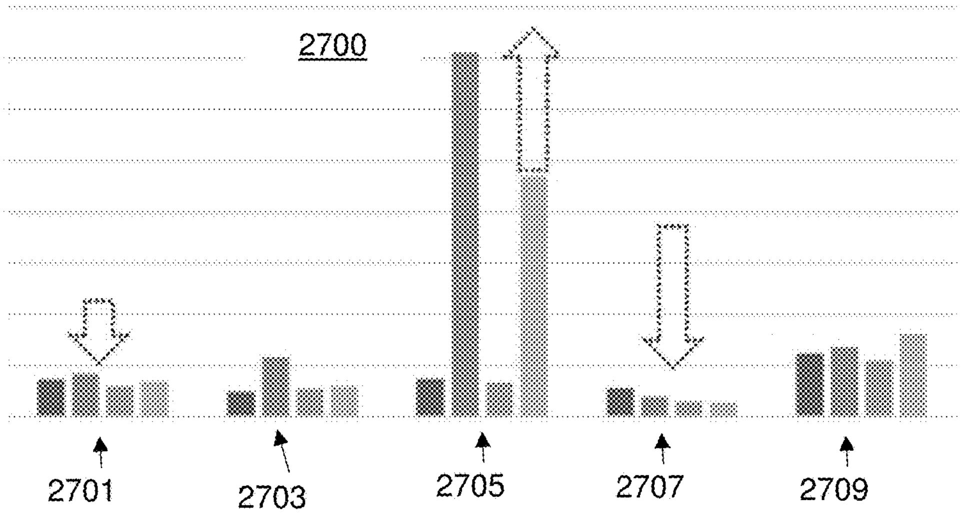
FIG. 27 shows a graph for PHYBRATA power for 30 second trials conducted under various conditions.

FIG. 27 shows a graph 2700 with PHYBRATA power as the y-axis. Four 30 second trials are administered to the patient 5 times, first with no EVS and then 4 more times with different EVS waveforms. A first trial (0 s-30 s) for each set has the patient keep their eyes open (Eo1) and is shown with the blue bars (leftmost bars in each set). A second trial for each set (30 s-60 s) has the patient keep their eyes closed (Ec1) and is shown with the orange bars (second from left). A third trial for each set (60 s-90 s) has the patient keep their eyes open (Eo2) and is shown with the grey bars (second from right), and a fourth trial for each set (90 s-120 s) has the patient keep their eyes closed (Ec2) and is shown with the yellow bars (rightmost bars in each set).

The first set of bars 2701 shows the baseline data for the patient with no EVS and represents their normal vestibular control. The second set of bars 2703 shows PHYBRATA data captured while an EVS waveform having spectral content of 0-2 Hz is administered at a current level of 750 μA. While the data for Ec0 is somewhat lower, and the data for Ec1 is elevated, that waveform does not seem to have significant impact, positive or negative on the balance of the patient.

The third set of bars 2705 shows PHYBRATA data captured while an EVS waveform having spectral content of 0-2 Hz is administered at a current level of 3000 μA. The data for Ec1 and Ec2 show that the vestibular control is significantly impaired or suppressed by this waveform. The fourth set of bars 2707 shows PHYBRATA data captured while an EVS waveform having spectral content of 0-25 Hz is administered at a current level of 750 μA. The data for each successive trial is lower showing enhanced vestibular control by this waveform. The fifth set of bars 2709 shows PHYBRATA data captured while an EVS waveform having spectral content of 0-25 Hz is administered at a current level of 3000 μA. The data for each trial is higher than the baseline showing somewhat impaired or suppressed vestibular control.

The data shown in FIG. 27 indicates that an EVS waveform with a wider range of spectral content administered at a lower current level may be an appropriate strategy for enhancing vestibular control. While the 0-25 Hz waveform at 750 μA provided the best results here, further refinement of the signal waveform, bandwidth, and current level may be performed to further optimize EVS stimulation parameters for an individual patient or a specific patient population, as a part of a pre-treatment therapeutic screening of patients, or in a real-time feedback loop during the treatment sessions to deliver adaptive and personalized treatments.

Figure 28:
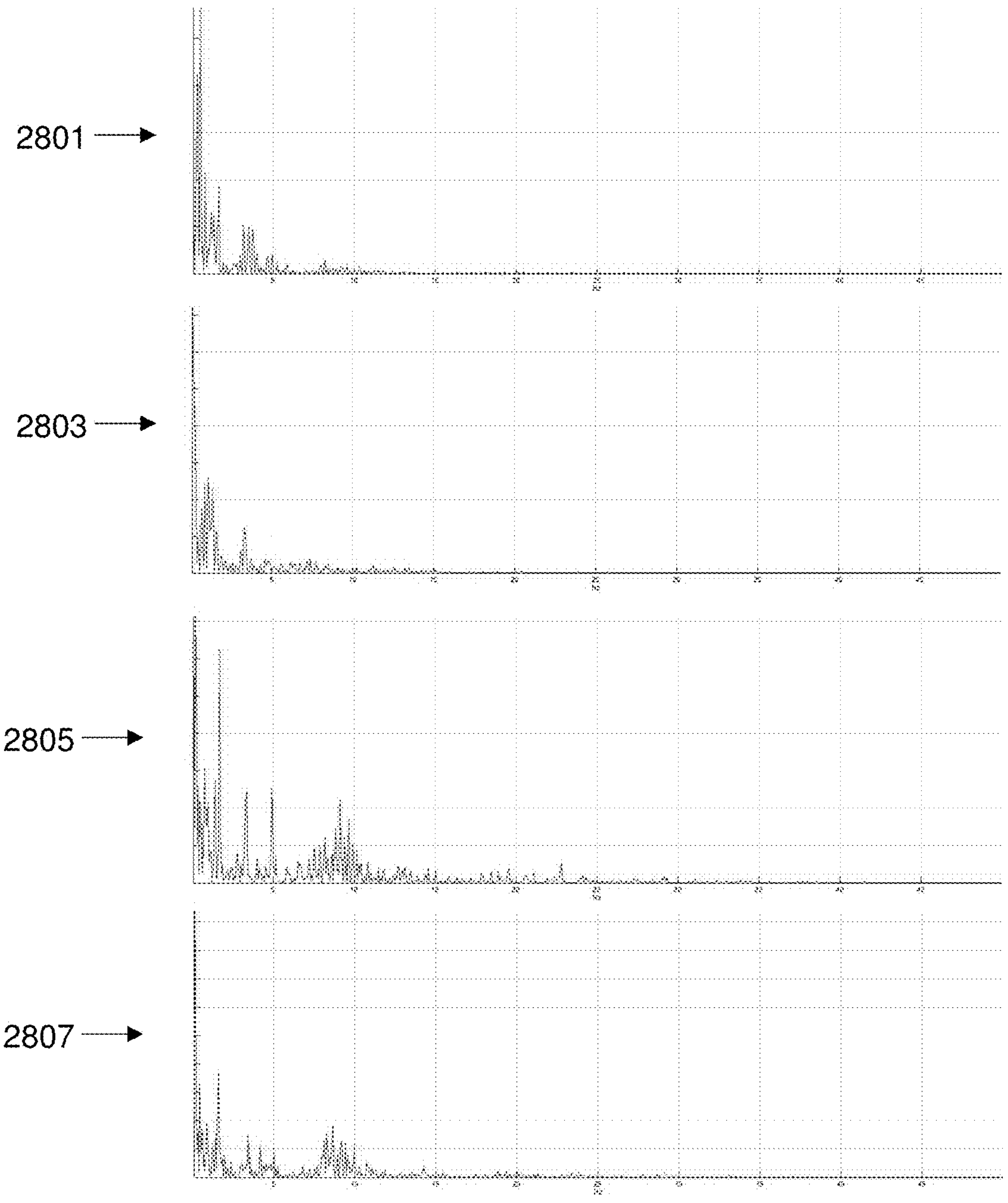
FIG. 28 shows frequency domain PHYBRATA power data for four trials.

FIG. 28 shows frequency domain PHYBRATA power data for four trials. In each graph, the x-axis runs from 0 Hz to 50 Hz, and the y-axis shows power spectral density amplitude. The first frequency domain data 2801 is for an eyes open trial with no EVS applied. The second frequency domain data 2803 is for an eyes closed trial with no EVS applied. The third frequency domain data 2805 is for an eyes open trial with an EVS signal having a frequency range of 0-25 Hz is applied at 750 μA, and the fourth frequency domain data 2807 is for an eyes closed trial with the same EVS signal. The data shown in FIG. 28 indicate that PHYBRATA sensor frequency domain data can be used to identify frequency ranges in sensory reweighting performance, and thus different components of balance control, that show significant change, such as enhanced vestibular balance control, in response to the application of EVS waveforms. Varying EVS waveforms, bandwidths, and intensities allows the identification of specific EVS stimulation parameters that optimize the therapeutic response of an individual patient or a specific patient population, for example enhancing vestibular balance control and reducing over-reliance on proprioceptive.

Figure 29:
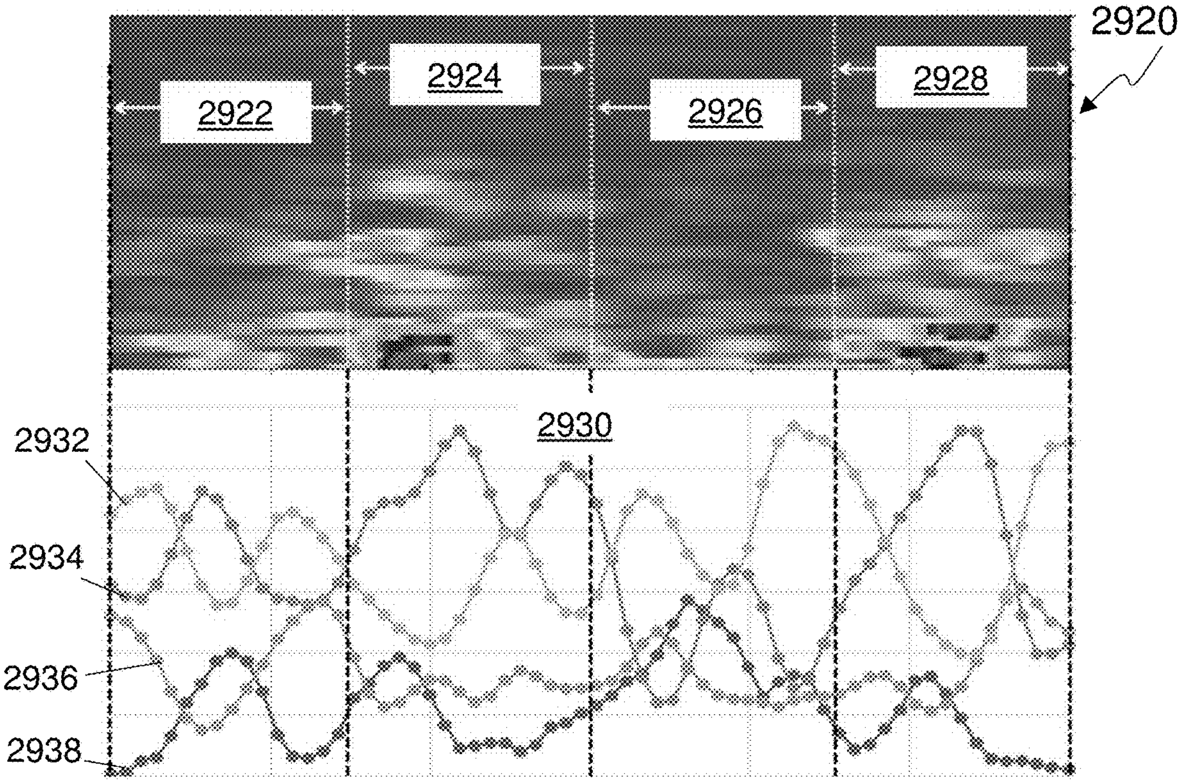
FIG. 29 shows time-resolved PHYBRATA acceleration and power data generated from data captured during four 30 second periods and a relative contribution of the various systems to balance over the time of the test periods.

FIG. 29 shows time-resolved PHYBRATA acceleration and power data 2920 generated from data captured during four 30 second periods while EVS is being applied at 750 μA over a frequency range of 0-25 Hz. During the first period 2922 the patient's eyes are open; during the second period 2924 the patient's eyes are closed; during the third period 2926 the patient's eyes are open; and during the fourth period 2928 the patient's eyes are closed again. The upper section 2920 shows data from an example patient data transformed into the frequency domain with the bottom of the colored area being 0 Hertz (Hz) and the top of the colored area being 30 Hz. Different colors represent different amplitudes of the various frequency bands over time which increases to the right.

Different frequency bands correlate with different aspects of the human balance system. The graph 2930 shows the relative contribution of the various systems to balance over the time of the test periods 2922-2928. The yellow data 2932 being indicative of proprioceptive balance control, the orange data 2934 indicative of vestibular balance control, the grey data 2936 indicative of central nervous system balance contribution, and the blue data 2938 indicative of visual balance control. The data shown in FIG. 29 indicate that time-resolved PHYBRATA sensor frequency domain data can be used to identify frequency ranges in sensory reweighting performance, and thus different components of balance control, that show significant change, such as enhanced vestibular balance control, in response to the application of EVS waveforms. These data also reveal changes in the relative contributions of different sensory inputs and CNS control to postural stabilization as a function of time. Varying EVS waveforms, bandwidths, and intensities allows the identification of specific EVS stimulation parameters that optimize the therapeutic response of an individual patient or a specific patient population, for example enhancing vestibular balance control and reducing over-reliance on proprioceptive.

Figure 30:
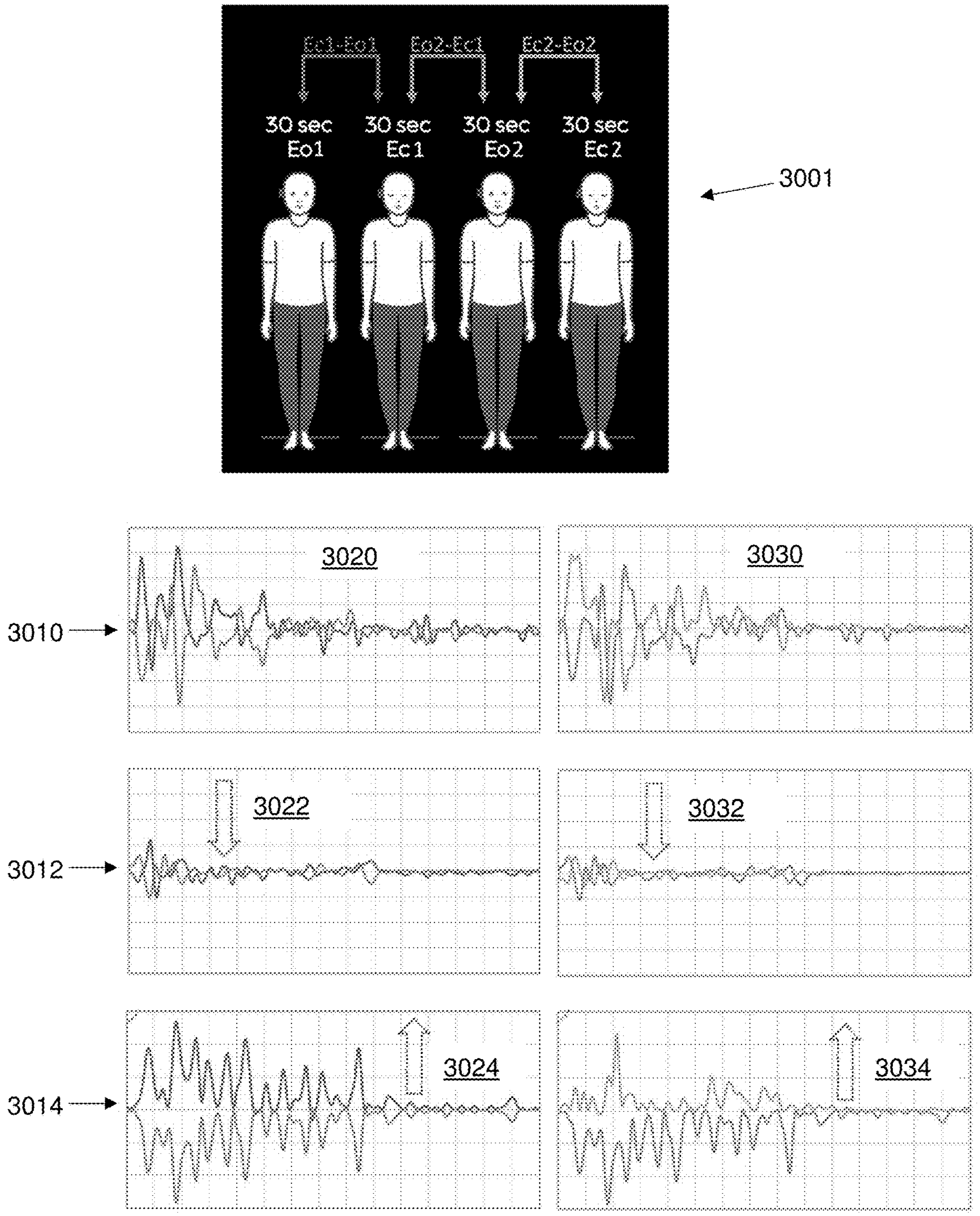
FIG. 30 shows changes in frequency domain data from a set of four 30 second trials.

FIG. 30 shows changes in frequency domain data from a set of four 30 second trials as illustrated 3001. Each set consisted of a first trial with eyes open (Eo1), and second trial with eyes closed (Ec1), a third trial with eyes open (Eo2) and a fourth trial with eyes closed (Ec2). The first set of data 3010 shown in the left graph 3020 and the right graph 3030 was generated from PHYBRATA data collected from a set of trials with no EVS being administered. Both graphs 3020, 3030 show changes in the power spectral density in the frequency domain over a range from 0-3 Hz. The blue line in graph 3020 shows the increase from the first trial to the second trial (Ec1-Eo1), the orange line in both graphs 3020, 3030 shows the increase from the second trial to the third trial (Eo2-Ec1), and the green line in graph 3020 shows the increase from the third trial to the fourth trial (Ec2-Eo2).

The second set of data 3012 shown in the left graph 3022 and the right graph 3032 was generated from PHYBRATA data collected from a set of trials with an EVS signal having a spectral content of 0-25 Hz administered at 750 μA. Both graphs 3022, 3032 show changes in the power spectral density in the frequency domain over a range from 0-3 Hz. The blue line in graph 3022 shows the increase from the first trial to the second trial (Ec1-Eo1), the orange line in both graphs 3022, 3032 shows the increase from the second trial to the third trial (Eo2-Ec1), and the green line in graph 3032 shows the increase from the third trial to the fourth trial (Ec2-Eo2). Comparing graph 3022 to graph 3020 and comparing graph 3032 to graph 3030, one can see that the changes are reduced, showing that the vestibular response is enhanced.

The third set of data 3014 shown in the left graph 3024 and the right graph 3034 was generated from PHYBRATA data collected from a set of trials with an EVS signal having a spectral content of 0-2 Hz administered at 3000 μA. Both graphs 3022, 3032 show changes in the power spectral density in the frequency domain over a range from 0-3 Hz. The blue line in graph 3022 shows the increase from the first trial to the second trial (Ec1-Eo1), the orange line in both graphs 3022, 3032 shows the increase from the second trial to the third trial (Eo2-Ec1), and the green line in graph 3032 shows the increase from the third trial to the fourth trial (Ec2-Eo2). Note that the maximum y-axis value of the graphs 3024, 3034 is 3× larger than the maximum y-axis value of the other graphs 3020, 3030, 3022, 3032. Comparing graph 3024 to graph 3020 and comparing graph 3034 to graph 3030, one can see that the changes are much greater, showing that the vestibular response is impaired or suppressed.

Figure 31:
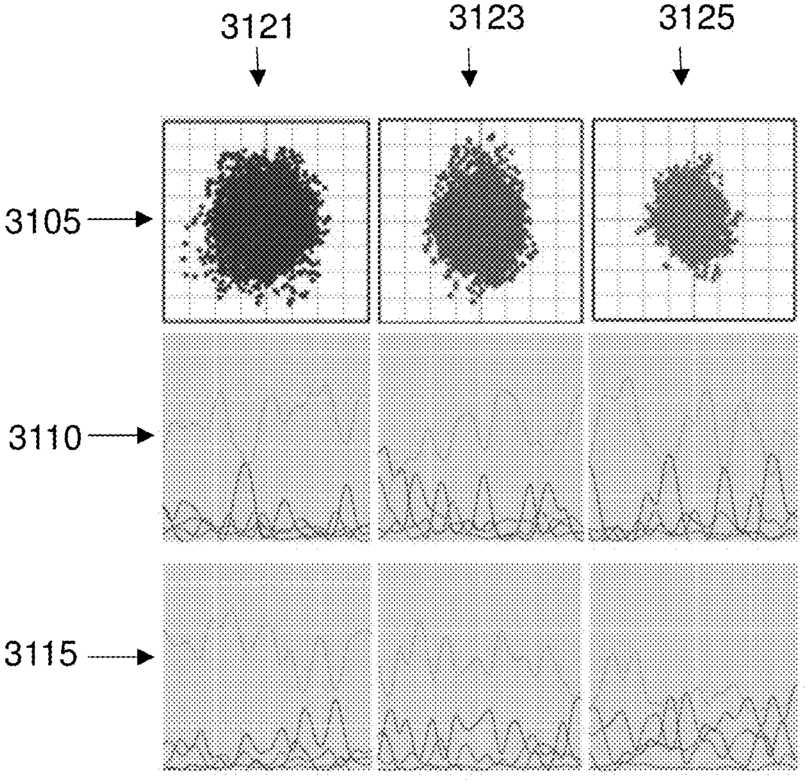
FIG. 31 shows AP vs. ML PHYBRATA acceleration scatter plots and sensory reweighting profiles measured before, during, and after application of a single 15-minute NEURVESTA EVS session.

FIG. 31 shows AP vs. ML PHYBRATA acceleration scatter plots 3105 and sensory reweighting profiles 3110, 3115 measured before 3121, during 3123, and after 3125 application of a single 15-minute EVS session provided to the same 63-year-old male patient used for FIG. 22-FIG. 25. The sensory reweighting profiles 3110, 3115 show visual system data in blue, proprioceptive data in yellow, vestibular data in red, central nervous control data in green, and VCR data in blue with the x-axis representing a percentage contribution and the y-axis being time through each 60 second trial.

Figure 32:
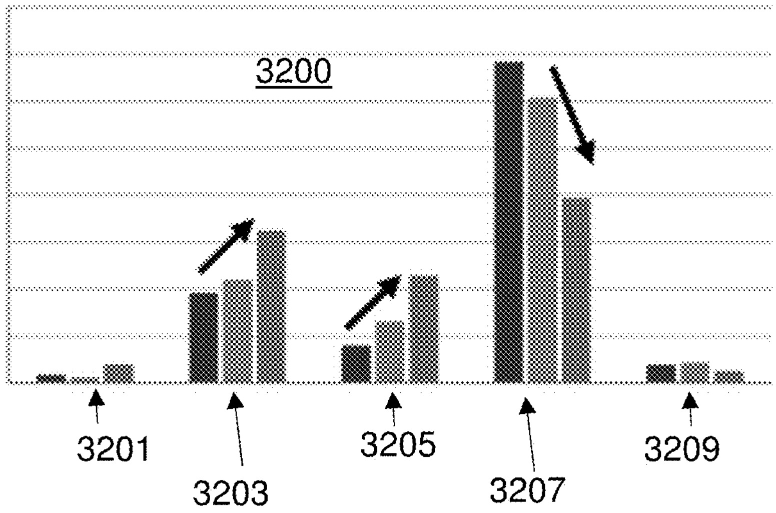
FIG. 32 shows the effect of an EVS session on sensory reweighting.

The EVS session consisted of a single 15-minute session of sub-threshold stochastic EVS, at a current level of 0.35 mA and frequency range of 0-640 Hz. This single EVS session leads to significant reductions in the postural stability degradations caused by all three balance challenges. PHYBRATA sensory reweighting analyses shown in graph 3200 of FIG. 32 reveal EVS-induced enhancements in CNS integration of sensory inputs, and up-regulation of vestibular balance control that is accompanied by down-regulation of proprioceptive balance control. Bars 3201 show visual system contribution, bars 3203 show vestibular system contribution, bars 3205 show central nervous system contribution, bars 3207 show proprioceptive contribution, and bars 3209 show VCR contribution. The red bars represent the pre-EVS data, the blue bars represent data captured during application of EVS, and the green bars represent post-EVS data. The results demonstrate that PHYBRATA sensor testing enables quantitative assessments of sensory reweighting due to postural stability challenges and EVS, providing an important adjunct to standard balance and gait testing that can also be integrated with EVS to support new balance treatment and rehabilitation strategies.

Figure 33:
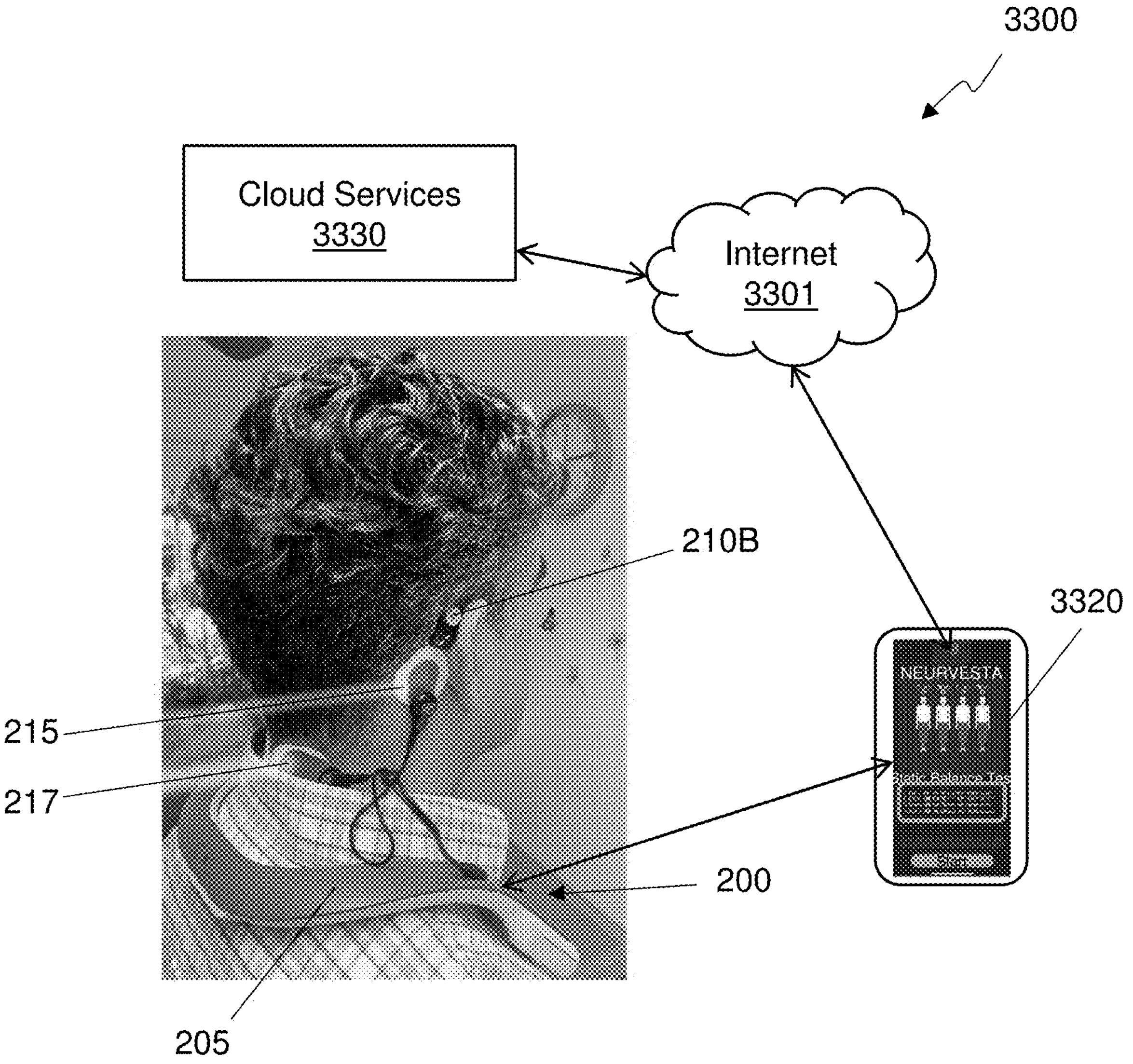
FIG. 33 shows an illustration of an example system using the NEURVESTA therapeutic device together with the PHYBRATA sensor.

As illustrated in FIG. 33, an example NEURVESTA system 3300 includes a PHYBRATA sensor 210B, the wearable NEURVESTA device 200, an app 3320, which may run on a smartphone, tablet, or another electronic device, to communicate with the PHYBRATA sensor and NEURVESTA device 200 using Bluetooth or any other appropriate communication protocol to configure and run diagnostic tests and therapeutic treatments, and a set of cloud data services 3330 accessible from the app 3320 through the internet 3301 or other computer network to support clinicians and patients. The NEURVESTA system 3300 can be utilized by clinical users caring for patients with balance impairments. It can also be made available via pharmacy distributors, enabling prescription at-home therapy for balance-impaired individuals.

The NEURVESTA device is designed to be comfortable and easy to use in both a clinical and home environment. The collar 205 includes one or more printed circuit boards (PCBs) and rechargeable batteries to allow it to be used untethered from a power supply. The miniaturized neurostimulation electronics module integrated within the NEURVESTA device 200 can replace a rack of instruments typically used in laboratory EVS apparatus. The NEURVESTA device may include wireless networking to allow it to communicate with cloud-based servers 3330 over the internet 3301 and/or local computers such as a local server, laptop, desktop, tablet, or smartphone. Networking capability may include cellular networking, Wi-Fi®, Bluetooth®, and/or other wireless or wired networks.

Figure 34:
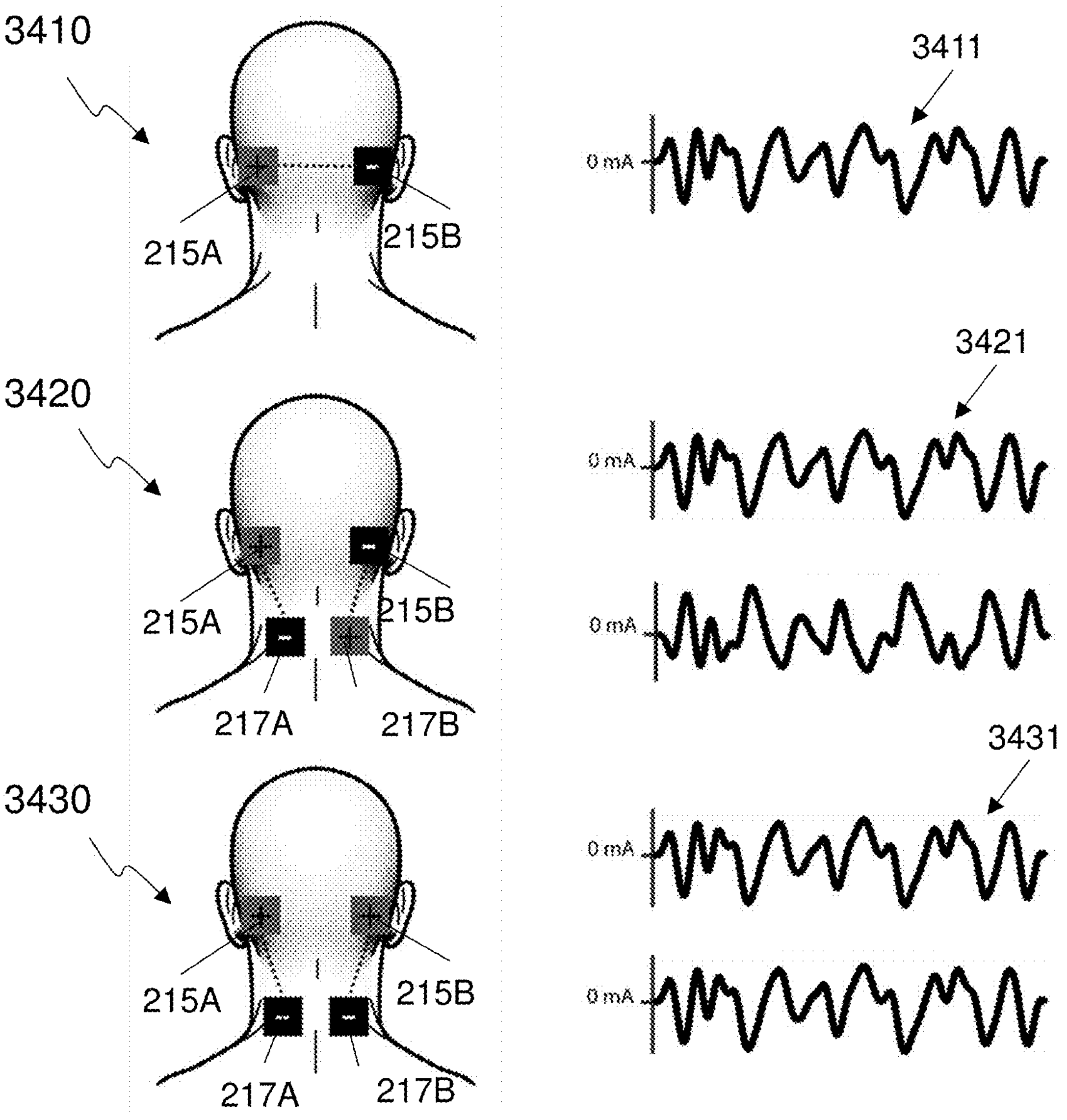
FIG. 34 shows different EVS electrode pair configurations.

FIG. 34 shows different EVS electrode pair configurations. A first configuration 3410 uses a single pair of electrodes 215A/215B affixed on or near the mastoids of the patient behind the ears. In the first configuration 3410, the EVS signal is a bipolar binaural waveform 3411 with one electrode 215A being the anode and a second electrode 215B being the cathode.

A second configuration 3420 uses two pairs of electrodes 215A/217A, 217B/215B. The first pair of electrodes 215A/217A is affixed on one side of the patient's head with the anode electrode 215A affixed on or near the mastoids of the patient behind the ear and the cathode electrode 217A affixed on the patient's neck. The second pair of electrodes 217B/215B is affixed on the other side of the patient's head with the cathode electrode 215B affixed on or near the mastoids of the patient behind the ear and the anode electrode 217B affixed on the patient's neck. In the second configuration 3420, the EVS signal is a bipolar binaural waveform 3421 which is applied across both pairs of electrodes 215A/217A, 217B/215A, but since the positions of the anode/cathode is reversed the patient's two vestibular organs receive inverted signals one from another.

A third configuration 3430 uses two pairs of electrodes 215A/217A, 215B/217B. The first pair of electrodes 215A/217A is affixed on one side of the patient's head with the anode electrode 215A affixed on or near the mastoids of the patient behind the ear and the cathode electrode 217A affixed on the patient's neck. The second pair of electrodes 214B/217B is affixed on the other side of the patient's head with the anode electrode 215B affixed on or near the mastoids of the patient behind the ear and the cathode electrode 217B affixed on the patient's neck. In the third configuration 3430, the EVS signal is a bipolar monopolar waveform 3431 which is applied across both pairs of electrodes 215A/217A, 215B/217A, and the patient's two vestibular organs receive the same signal.

In other configurations, two pairs of electrodes may be used in the same configuration as either the second configuration 3420 or the third configuration 3430, but different EVS waveforms may be provided to the two pairs of electrodes, so that the patient's two vestibular organs receive the different signals.

A VST treatment session may include affixing the first electrode on or near a right mastoid of the user, affixing a second electrode on or near a left mastoid of the user, affixing a third electrode and a fourth electrode onto the user, applying a first stochastic wideband subthreshold EVS (swsEVS) waveform to the user through the first electrode and third electrode, and applying a second swsEVS waveform to the user through the second electrode and fourth electrode. Depending on the treatment plan, the first swsEVS waveform may be identical to or different from the second swsEVS waveform. In some cases, the two waveforms may be the same, but the polarity of the first swsEVS waveform at the first electrode is inverted from a polarity of the second swsEVS waveform at the second electrode.

In some VST treatment protocols, the EVS stimulation is delivered using a 4-electrode binaural bipolar electrode configuration at current levels above the vestibulospinal recruitment threshold (on the order of 0.05 mA or less) and below the tactile perceptual threshold (typically 0.5 mA or greater). In other VST treatment protocols, the EVS stimulation is delivered using a 4-electrode binaural bipolar electrode configuration at current levels above the vestibulo-cervical recruitment threshold (on the order of 0.05 mA or less) and below the tactile perceptual threshold (typically 0.5 mA or greater). The vestibulospinal recruitment threshold of each patient is determined by measuring the onset of motion of the body detected with the patient standing on a force plate, while the vestibulo-cervical recruitment threshold of each patient is determined by measuring the onset of motion of the head detected using a head-mounted PHYBRATA sensor.

The VST treatment delivers long-lasting neuroplastic restoration of balance, accompanied by significant improvements in mobility and gait, and reductions in fall risk. In some VST treatment protocols, the swsEVS stimulation is delivered during 18 twenty-minute treatment sessions delivered over a 4-6-week period. Significant improvements in balance are typically measured and reported within the initial two treatment sessions. These improvements continue to increase progressively, plateau after 12-18 sessions, and then persist for at least six months, at which point a shorter maintenance treatment can be delivered. No adverse events were reported during these studies. Furthermore, testing with the PHYBRATA wearable sensor and digital biomarkers can screen out non-responders (<5% of study participants to date) during the first two treatment sessions, which limit costs and unproductive time for payers, providers, and patients alike. These results confirm that VST treatments are safe, well-tolerated, and have no adverse side effects.

Looking back to FIG. 33, the NEURVESTA system 3300 may include a mobile app 3320 to provide a control interface with which a user can configure, run, and report the results of PHYBRATA balance and gait tests administered in conjunction with swsEVS treatment sessions. The mobile app 3320 interface can enable a user to run PHYBRATA balance and gait tests and display the results before and after each swsEVS treatment session in a multi-session VST treatment protocol, and to display the cumulative changes in PHYBRATA balance and gait performance across multiple swsEVS treatment sessions. The mobile app 3320 interface may be configured to enable a user to connect to PHYBRATA and NEURVESTA devices, to create new patient records, and to select patients for PHYBRATA tests and NEURVESTA treatments. It also me be configured to enable a user to create a treatment plan and prepare a patient for PHYBRATA tests and NEURVESTA treatments, to initiate and monitor a treatment session workflow, and to complete a treatment plan and review the results of individual and multiple PHYBRATA tests. It also may be able to display multiple balance performance and sensory reweighting reports, and to display reports in multiple formats that summarize changes in PHYBRATA sensory reweighting over time.

The mobile app 3320 interface can enable a user to configure, run, and report the results of multiple PHYBRATA-sensor balance and gait tests, including:

Sequences of consecutive eyes-open (Eo) and eyes closed (Ec) balance tests.

Timed up and go (TUG) tests.

Fixed distance walking tests.

The NEURVESTA system 3300 also includes a wearable PHYBRATA sensor 210A which may be integrated into the NEURVESTA device 200 or may be a separate wearable device 210B as shown, having its own power source (e.g., a battery) or may have a wire to the collar 205 of the NEURVESTA device 200 or some other source of power. The PHYBRATA sensor 210A/210B measures head accelerations in one or more linear and/or rotational directions and may communicate with the app 3320 through the NEURVESTA device 200 (e.g., if the PHYBRATA sensor 210A/210B is integrated with or wired to NEURVESTA device 200), or directly through a wired or wireless connection such as Bluetooth. The PHYBRATA sensor 210A/210B, for example, may measure any combination of anterior-posterior (AP) acceleration (x-axis), mediolateral (ML) acceleration (y-axis), and/or vertical acceleration (z-axis). In some implementations the PHYBRATA sensor 210A/210B may include gyroscopes or other types of sensors for measurements of yaw acceleration, pitch acceleration, and/or roll acceleration.

The NEURVESTA system 3300 enables discovery and delivery of non-invasive bioelectronic treatments that can achieve large and persistent restoration of central vestibular balance via neurogenesis in the vestibular nuclei. It includes a novel non-invasive bioelectronic device (NEURVESTA 200) with a PHYBRATA sensor 210A/210B and vestibular stimulation treatment (VST) protocol to enable discovery and delivery of non-invasive bioelectronic treatments that can achieve large and persistent restoration of balance and gait using electrical or electrohydrodynamic stimulation to induce neurogenesis in the peripheral and central vestibular systems.

The NEURVESTA system 3300 enables discovery and delivery of non-invasive bioelectronic treatments that can achieve large and persistent restoration of peripheral and central vestibular balance functions using electrical or electrohydrodynamic stimulation of developmental pathways to enhance hair cell regeneration in the peripheral vestibular system and neurogenesis in the peripheral and central vestibular systems.

The NEURVESTA system 3300 enables discovery and delivery of non-invasive bioelectronic treatments that can achieve large and persistent restoration of peripheral and central vestibular balance functions using electrohydrodynamic stimulation of the peripheral vestibular balance organs to remove otoconia from the semicircular canals.

The NEURVESTA system 3300 enables discovery and delivery of non-invasive bioelectronic treatments that can achieve large and persistent neuroplastic restoration of peripheral and central vestibular balance functions that have been degraded by normal or accelerated aging conditions using electrical or electrohydrodynamic stimulation to induce neurogenesis in the peripheral and central vestibular systems.

FIG. 35 through FIG. 39 present several graphs to illustrate the effects of a single NEURVESTA device swsEVS session on sensory reweighting in older adults and the corresponding EVS-induced reduction of age-related balance impairments. Data are presented from 13 adult participants aged 58-89 yrs (4 female, 9 male). Standing balance tests were first carried out using a head-mounted PHYBRATA sensor. PHYBRATA time series data and spatial scatter plots, eyes open (Eo) and eyes closed (Ec) PHYBRATA powers, Ec/Eo PHYBRATA power ratios, and time-resolved PHYBRATA power spectral density (PSD) distributions are compared for two different postural stability challenges: eyes open vs. eyes closed and standing on hard floor vs. foam pad. PHYBRATA testing was then carried out before and after a 15-minute application of swsEVS.

Figure 35:
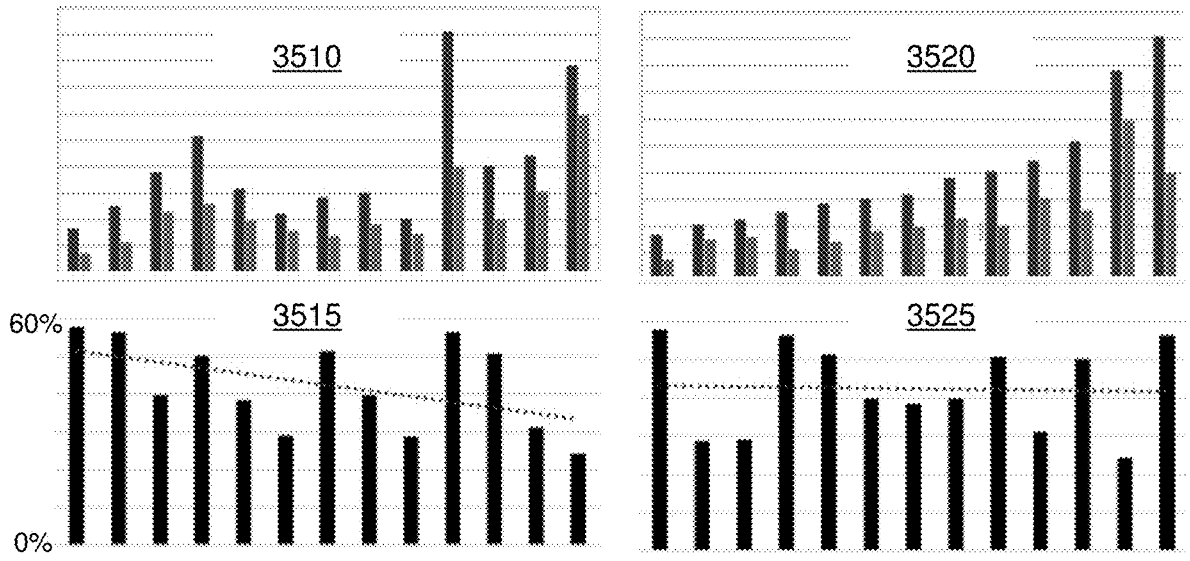
FIG. 35 presents pre-EVS and post-EVS Ec PHYBRATA powers and the corresponding percentage decrease in Ec PHYBRATA power sorted by age by initial balance degradation of the participants.

PHYBRATA time series data, spatial scatter plots, Eo and Ec PHYBRATA powers, and Ec/Eo PHYBRATA power ratios all demonstrate degraded postural stability for Ec vs. Eo and foam pad vs. hard floor. FIG. 35 presents pre-EVS (red bars—left side of pairs) and post-EVS (green bars—right side of pairs) Ec PHYBRATA powers in graph 3510 with and the corresponding percentage decrease in Ec PHYBRATA power in graph 3515 sorted by age of the participants. The same data is presented in graph 3520 and graph 3525 but with the data sorted by the magnitude of the initial balance degradation of the participants. The results presented in FIG. 35 demonstrate that a single 15-minute application of NEURVESTA sub-threshold stochastic EVS led to significant reductions in age-related balance impairments for all 13 participants.

Figure 36:
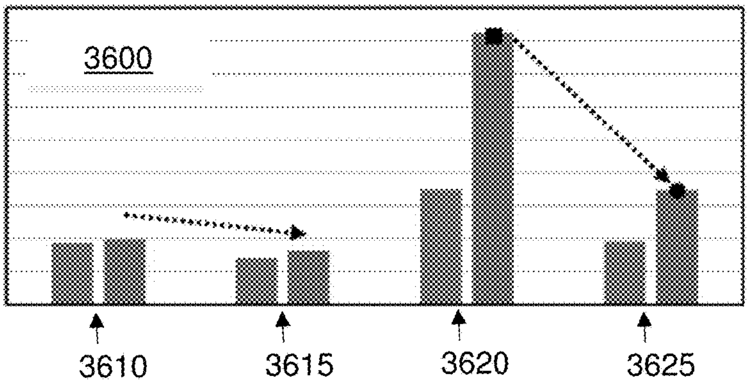
FIG. 36 presents PHYBRATA power measurements demonstrating that EVS enhancements to balance performance are larger when postural stability is challenged (foam pad vs. hard floor).

FIG. 36 presents example PHYBRATA power measurements from a 58-year-old male in graph 3600. The blue bars (left side of each pair) show data from trials with eyes open and red bars (right side of each pair) show data from trials with eyes closed. Bars 3610 show data from trials with the patient standing on a hard floor before EVS therapy was used and bars 3615 show data from trials with the patient standing on a hard floor after EVS therapy was used. Bars 3620 show data from trials with the patient standing on a foam pad before EVS therapy was used and bars 3525 show data from trials with the patient standing on a foam pad after EVS therapy was used. This demonstrates that EVS enhancements to balance performance are larger when postural stability is challenged (foam pad vs. hard floor).

Figure 37:
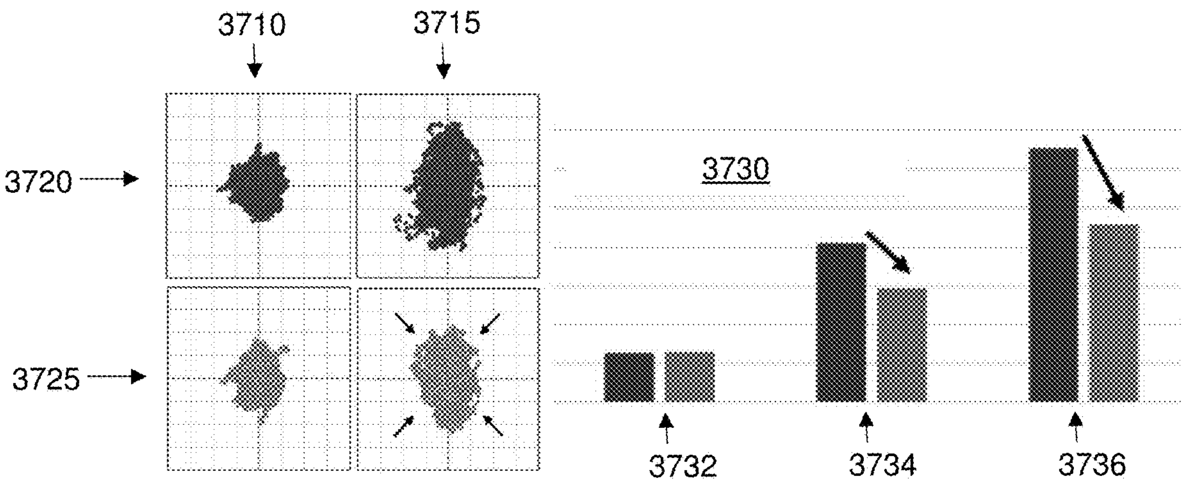
FIG. 37 presents example scatter plots and PHYBRATA power before and after an EVS therapy session.

FIG. 37 presents example scatter plots and PHYBRATA power before and after an EVS therapy session for a 68-year-old woman standing with feet together on a hard floor. The red scatter plots 3720 show data from before the EVS therapy session and the green scatter plots 3725 show data from after the EVS therapy session. The scatter plots on the left 3710 show data from trials with eyes open and the scatter plots on the right 3715 show data from trials with eyes closed. Note the compression of the eyes closed scatter plots 3715 from pre-EVS to post-EVS trials.

Graph 3730 uses PHYBRATA power for the y-axis and shows data from before the EVS therapy session in red (left side of each pair) and data from after the EVS therapy session in green (right side of each pair). Bars 3732 show eyes open data which shows very little change from the EVS therapy. But bars 3734 presenting eyes closed data, and bars 3736 showing Ec/Eo ratios show a large improvement caused by the EVS therapy.

Figure 38:
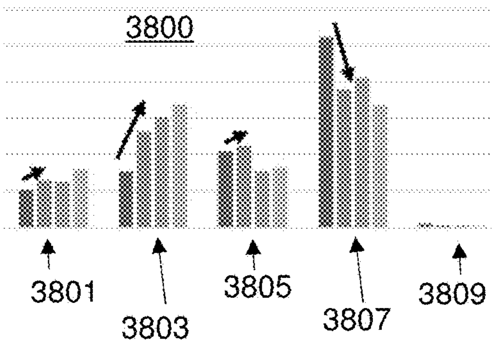
FIG. 38 presents example PHYBRATA sensory reweighting profiles for the EVS induced balance recovery shown in FIG. 25.

FIG. 38 presents example PHYBRATA sensory reweighting profiles for the EVS induced balance recovery shown in FIG. 37. Graph 3800 has five sets of bars, showing normalized PHYBRATA power spectral density (PSD) for visual 3801, vestibular 3803, central nervous system 3805, proprioceptive 3807, and VCR 3809. The blue bars (leftmost bars of each set) show data from pre-EVS eyes open trials, the orange bars (second from left) show data from post-EVS eyes open trials, the grey bars (second from right) show pre-EVS eyes closed trials, and the yellow bars (rightmost bar) show post-EVS eyes closed trials. The example PHYBRATA sensory reweighting profiles demonstrate that EVS induced balance recovery results from enhancements in CNS integration of sensory inputs, together with up-regulation of vestibular and visual balance control that is accompanied by down-regulation of excessive reliance on proprioceptive balance control.

Figure 39:
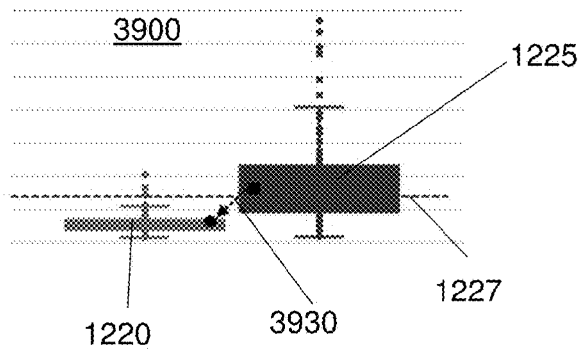
FIG. 39 shows the use of eyes-closed PHYBRATA power (Ec) as a diagnostic biomarker for fall risk.

FIG. 39 shows that using the eyes-closed PHYBRATA power (Ec) as a biomarker for fall risk indicates that single-session EVS-induced balance enhancements may be sufficient to transition a faller to a non-faller. Graph 3900 reproduces the eyes closed biomarker data from FIG. 12 for non-fallers 1220 and fallers 1225 with the biomarker of Ec=0.89 1227. Data from one participant is shown with their pre-EVS Ec data (black square) in the faller category, but they transitioned 3930 to the non-faller category below the biomarker line 1227 after one EVS session (black dot).

In some cases, applying EVS to the subject in a single session increases postural stability or gait stability in a manner that persists for a period longer than 24 hours after completion of the single EVS session, and applying EVS to the subject over multiple consecutive or non-consecutive daily sessions increases postural stability or gait stability in a manner that is cumulative and persists for a period of up to 12 months or more after completion of the multiple EVS sessions.

Figure 40:
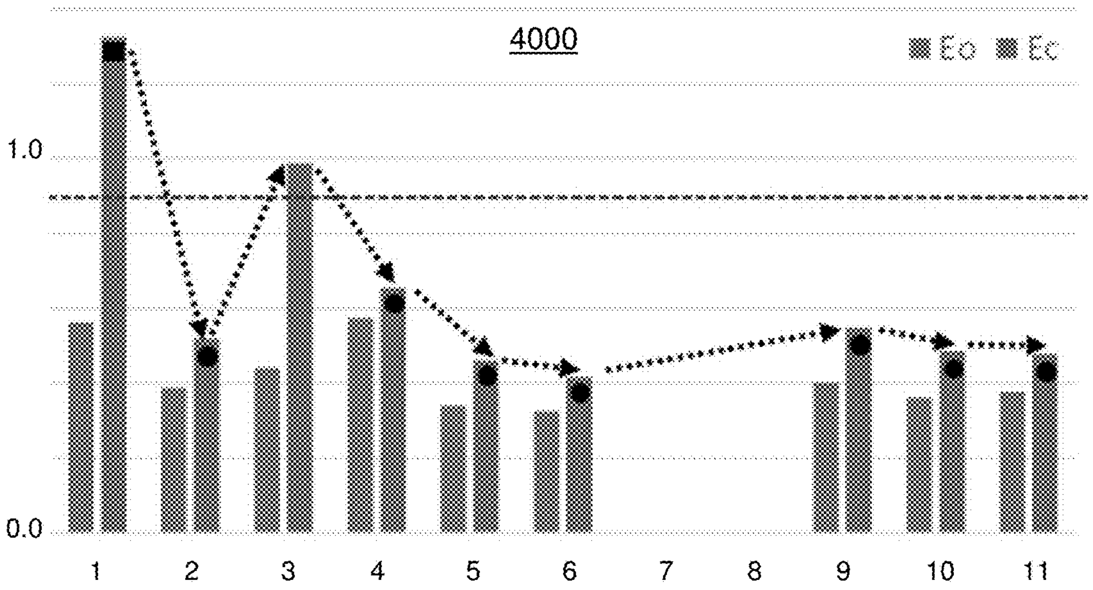
FIG. 40 shows PHYBRATA power measurements demonstrating persistent EVS enhancements to balance performance over 6 days of NEURVESTA EVS sessions.
Figure 41:
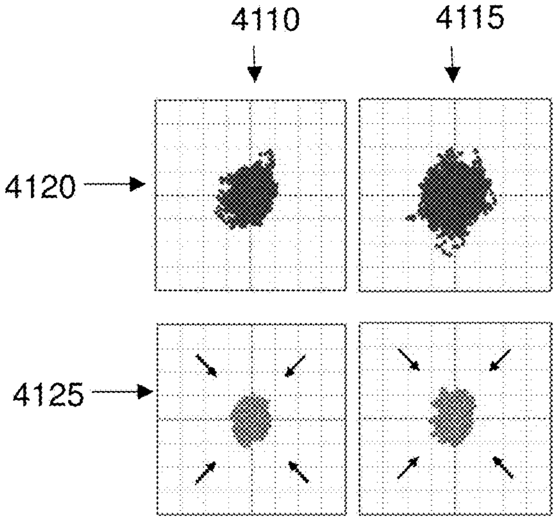
FIG. 41 shows AP vs. ML PHYBRATA acceleration scatter plots measured before and after three consecutive daily NEURVESTA EVS sessions.
Figure 42:
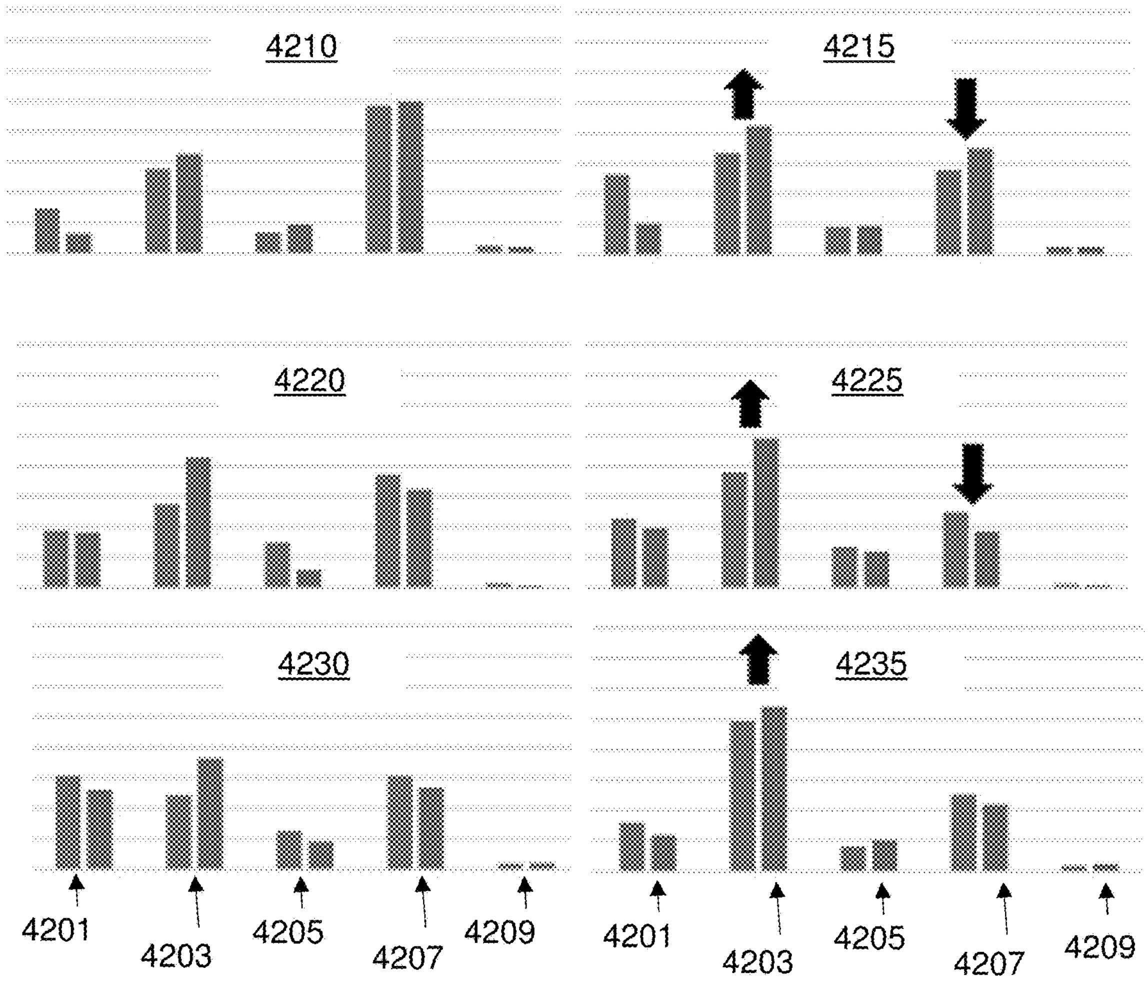
FIG. 42 shows example PHYBRATA sensory reweighting profiles for cumulative and persistent EVS induced balance recovery.

FIG. 40-FIG. 42 present several graphs to illustrate the effects of multiple consecutive daily NEURVESTA device swsEVS sessions on sensory reweighting in older adults and the corresponding EVS-induced reduction of age-related balance impairments. An 88-year-old female patient was treated with daily 20-minute swsEVS having a frequency range of 0-640 Hz and administered with 350 μA of current.

FIG. 40 shows PHYBRATA power measurements demonstrating cumulative and persistent EVS enhancements to balance performance over 6 days of NEURVESTA EVS sessions. The y-axis of graph 4000 is PHYBRATA power and the graph presents measurements from 11 sessions over 6 days. Eyes open data is shown in blue (left bar of each pair of bars) and eyes closed data is shown in red (right bar of each pair of bars). Session 1 is day 1 pre EVS. Session 2 is day 1 post EVS. Session 3 is day 3 pre EVS. Session 4 is day 2 post EVS. Session 5 is day 3 pre EVS. Session 6 is day 3 post EVS. Sessions 7 and 8 correspond to pre EVS and post EVS on day 4, which had no treatments or measurements. Session 9 is day 5 pre EVS. Session 10 is day 5 post EVS. Session 11 is day 6 pre EVS. No EVS was carried out on day 6. After day 3, the observed magnitude of EVS-induced balance enhancement is already sufficient to transition a faller to a non-faller, as represented by the purple line at 0.89 W of PHYBRATA power. The results for day 3 through day 6 indicate that the balance enhancements from the EVS treatment may have reached a plateau and become persistent.

FIG. 41 shows AP vs. ML PHYBRATA acceleration scatter plots measured before and after the initial three consecutive daily NEURVESTA EVS sessions and demonstrating significant EVS-induced balance enhancement. The red scatter plots 4120 show data from before the EVS therapy session on day one and the green scatter plots 4125 show data from after the third daily EVS therapy session. The scatter plots on the left 4110 show data from trials with eyes open and the scatter plots on the right 4115 show data from trials with eyes closed. Note the compression of both the eyes open 4110 and eyes closed scatter plots 4115 from pre-EVS 4120 to day 3 post-EVS 4125 measurements.

FIG. 42 presents exemplary PHYBRATA sensory reweighting profiles from the same data summarized in FIG. 40 and FIG. 41 demonstrating that EVS induced balance recovery results from up-regulation of vestibular and visual balance control that is accompanied by down-regulation of excessive reliance on proprioceptive balance control. 6 different graphs are included with eyes open data in blue (left bar of each pair) and eyes closed data in red (right bar of each pair). Each graph has normalized PHYBRATA PSDs for its y-axis and has 5 sets of bars for visual 4201, vestibular 4203, central nervous system 4205, proprioceptive 4207, and VCR 4209 contributions to balance. Graph 4210 shows day 1 pre-EVS data and graph 4215 shows post-EVS data from day 1. Graph 4220 shows day 2 pre-EVS data and graph 4225 shows post-EVS data from day 2. Graph 4230 shows day 3 pre-EVS data and graph 4235 shows post-EVS data from day 3. Note that for the first two days, vestibular contribution goes up, and proprioceptive contribution goes down in response to that day's EVS treatment. By the third day, vestibular contribution still rises, but the proprioceptive response is less affected, which may indicate that the EVS treatment changes are approaching a plateau and becoming persistent.

FIG. 43 through FIG. 47 present results from a randomized control trial (RCT) using an example standardized VST treatment protocol developed as one implementation. This example standard protocol utilizes a swsEVS stimulation waveform and eighteen 20-minute treatment sessions administered over a 4-6-week period. This standard treatment protocol was administered to a group of 50 participants with ages ranging from 50 to 95 years old. Enrollment criteria were as follows:

- Age 50+
- Able to complete balance assessments such as standing unassisted with feet together/eyes open and feet together/eyes closed, both for at least 1 minute at a time, with no more than 1-minute rest required between tests.
- Able to complete gait assessment tests such as walking up to 200 m on a flat surface without assistance.
- No pacemaker, cochlear implant, or any other implanted electronic device.
- No diagnosed neurological disorder or other significant comorbid neurological or musculoskeletal condition associated with impaired balance and elevated fall risk.

Participants were randomly assigned to a Stimulation group (swsEVS intervention) or Sham group. The swsEVS regimen included low-amplitude wideband stochastic stimulation (±350 μA, 0.001-300 Hz). Balance performance was assessed immediately before and after each 20-minute swsEVS treatment session using a head-mounted PHYBRATA sensor and digital biomarkers to assess postural stability in four conditions: Hard Floor Eyes Open, Hard Floor Eyes Closed, Foam Pad Eyes Open, and Foam Pad Eyes Closed. Follow-up testing was carried out at 3 months and 6 months post-intervention to assess persistence. Postural stability data were analyzed using a linear mixed model analysis with group (Stim or Sham), session (Session 1 to 18), and interaction of group and session as fixed factors. Pairwise comparisons were used to quantify changes in performance between Session 1 and subsequent sessions. An alpha level of 0.05 was used as the statistical significance threshold for all testing.

Figure 43:
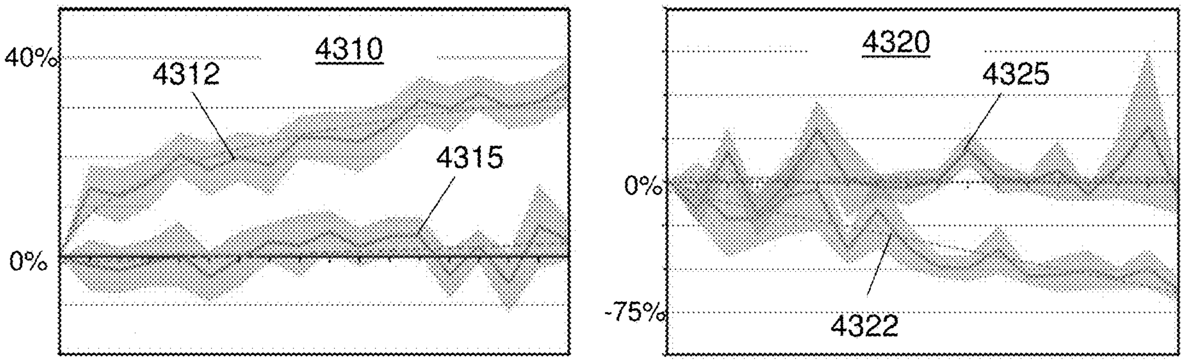
FIG. 43 presents test results for the six-week VST treatment protocol.

FIG. 43 presents Hard Floor Eyes Closed PHYBRATA balance test results 4310 and fall risk assessments 4320 for the Stimulation Group 4312, 4322, shown in green, and the Sham group 4315, 4325, shown in blue. Balance improvements in the treatment group begin in the initial treatment session, increase progressively, plateau after 5-6 weeks, and persist for 6 months or longer, at which point a shorter maintenance treatment can be delivered. As illustrated in FIG. 43, the VST treatment protocol delivered significant balance enhancements and fall risk reductions in Stimulation group participants. Sham group participants did not show significant changes in balance performance, validating the efficacy of the VST treatment protocol.

Figure 44:
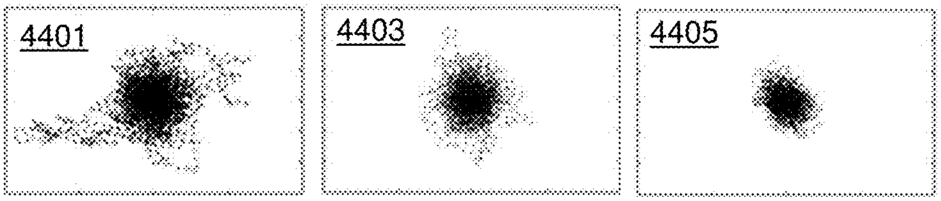
FIG. 44 presents test results for an example standardized EVS treatment protocol.

FIG. 44 presents PHYBRATA scatter plots before and after the VST treatment from a sample Stimulation group participant. Scatter plot 4401 shows AP/ML acceleration before treatment, scatter plot 4403 shows AP/ML acceleration at the end of the 6-week treatment, and scatter plot 4405 shows AP/ML acceleration 3 weeks after the end of the 6-week treatment. It can be seen that the treatment greatly reduced postural instability in the study participants and that their balance performance continues to improve even further following the end of the treatment.

The Stimulation group also exhibited significant and sustained improvements in postural stability in the two Foam Pad testing conditions, suggesting that EVS is most effective under conditions requiring greater reliance on vestibular inputs. Improvements were observed within the first three treatment sessions and persisted through 6 months. The Sham group demonstrated small and inconsistent improvement in postural stability, potentially reflecting a learning effect, and these improvements did not persist. No adverse events were reported during the RCT.

Figure 45:
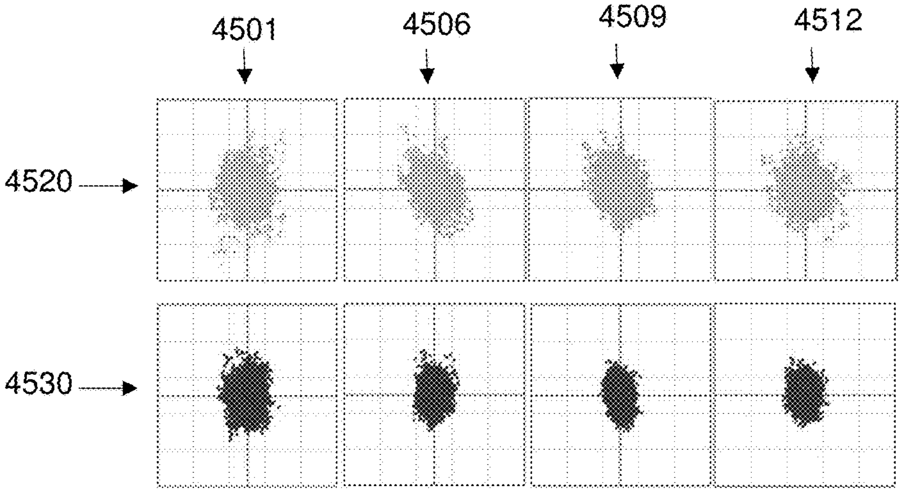
FIG. 45 shows PHYBRATA AP/ML acceleration scatter plots for participants that received sham treatment and for participants that received real treatment.

As illustrated in FIG. 45, PHYBRATA AP/ML acceleration scatter plots reveal significant postural sway reductions in Stimulation group test subjects but not in Sham control group subjects following the standardized VST treatment protocol. The top row of scatter plots in yellow 4520 show sway data during a 25-foot walking test from participants who received sham treatments and the bottom row of scatter plots in red 4530 show sway data from participants who received real EVS treatments. The scatter plots in the first column 4501 show data at the end of the first week of treatments, the scatter plots in the second column 4506 show data at the end of the 6 weeks of treatments, the scatter plots in the third column 4509 show data at the end of the third week after the end of treatments (9 weeks from the start of the study), and the scatter plots in the fourth column 4512 show data at the end of the sixth weeks after the end of treatments (12 weeks from the start of the study). It can easily be seen that the participants that received the sham treatments 4520 did not improve their sway performance, while those that received the real EVS treatments 4530 improved over the 6 weeks of the treatments and maintained that improvement through at least the following 6 weeks.

Figure 46:
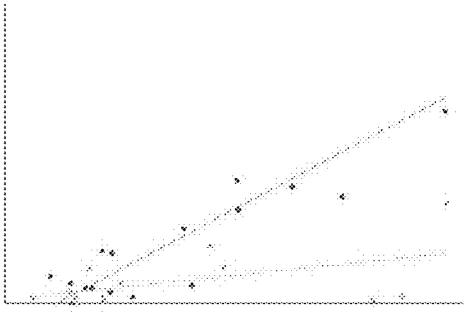
FIG. 46 shows a scatter plot of each patient's initial Ec PHYBRATA power plotted against their cumulative change in Ec PHYBRATA power.

FIG. 46 shows a scatter plot of each patient's initial Ec PHYBRATA power (x-axis) plotted against their cumulative change in Ec PHYBRATA power (y-axis) following each of the 18 subsequent therapeutic sessions. The swsEVS stimulation group has an R2=0.8412, while the control group receiving a sham stimulation has an R2=0.2562, demonstrating a large correlation between the initial level of balance impairment and the level of balance recovery delivered using the standard swsEVS therapeutic treatment protocol.

Figure 47:
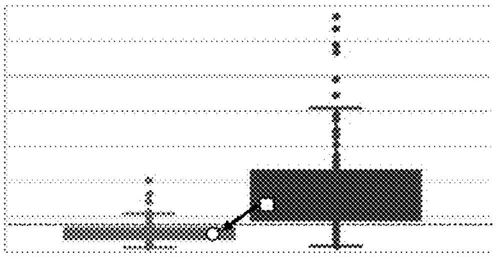
FIG. 47 shows that test subjects changed from being a fall risk to not being a fall risk as a result of swsEVS treatments.

FIG. 47 shows that test subjects whose Ec PHYBRATA power exceeded the fall risk threshold (0.89 W) before receiving the standard 6-week swsEVS treatment protocol achieved Ec PHYBRATA power significantly below the fall risk threshold (0.89 W) after receiving the standard 6-week swsEVS treatment protocol.

These findings establish multi-session swsEVS using the NEURVESTA system to deliver a VST protocol as a promising non-invasive and portable intervention for addressing balance deficits in aging populations. The VST protocol delivers significant balance enhancements in patients from 50 to 95 years old, as measured using PHYBRATA AP/ML acceleration scatter (postural sway) plots and normalized Ec PHYBRATA power. Patients who receive the standard swsEVS therapeutic treatment protocol typically report immediate and significant improvement in balance and ambulatory confidence in their initial treatment sessions. These improvements continue to increase progressively throughout treatment and are projected to persist for 6-12 months or longer following completion of treatment.

FIG. 48 through FIG. 59 present results from a pilot study using the above example standardized VST treatment protocol administered to a group of 32 residents aged 60-98 years from a continuing care retirement community. The 18-session VST treatment protocol was delivered over a 4-6-week period by trained home care providers. Each session included low amplitude (±0.35mA), wideband (0-300 Hz), stochastic EVS for 20 minutes delivered using the NEURVESTA wearable bioelectronic stimulation device. Balance performance was assessed immediately before and after each treatment session using a head-mounted PHYBRATA sensor, with participants standing in socks on a hard floor for one minute with eyes open, followed by one minute with eyes closed. Balance performance and fall risk biomarkers derived from the PHYBRATA time series data included eyes open (Eo) and eyes closed (Ec) PHYBRATA powers. Sensory reweighting biomarkers were derived from PHYBRATA acceleration spectral density (ASD) distributions. Two additional standard balance tests were also administered prior to the first treatment session and following completion of the $18^{th}$ treatment session: standing on 1 leg and standing on a foam pad with feet together and eyes closed. Gait performance was measured prior to the first treatment session and following completion of the $18^{th}$ treatment session using 3 time-synchronized IMUs, 2 of which were attached to the shoes, and one attached to the mastoid. Patients walked 2 distances of 7.6 meters and 20 meters on a hard surface wearing shoes. Multiple gait metrics were calculated from the IMU data.

Figure 48:
FIG. 48 shows a group of VST pilot participants during 20-minute treatment session.

Since VST uses stimulation current levels that are below the perceptual threshold, there is no physical sensation during the treatment sessions, which makes it very comfortable and well-tolerated. Since the treatment does not require any specialized physical activity during the 20-minute treatment session, VST can be administered to groups of participants seated together, as illustrated in FIG. 48, enabling an engaging and social treatment environment that leads to very high levels of adherence.

30 of the 32 participants demonstrated significantly improved balance and gait performance and reduced fall risk following the 18-session EVS treatment protocol. 2 of the 32 participants demonstrated no significant changes. PHYBRATA biomarkers were found to identify the 2 non-responders in the study population within the first 2 treatment sessions.

Figure 49:
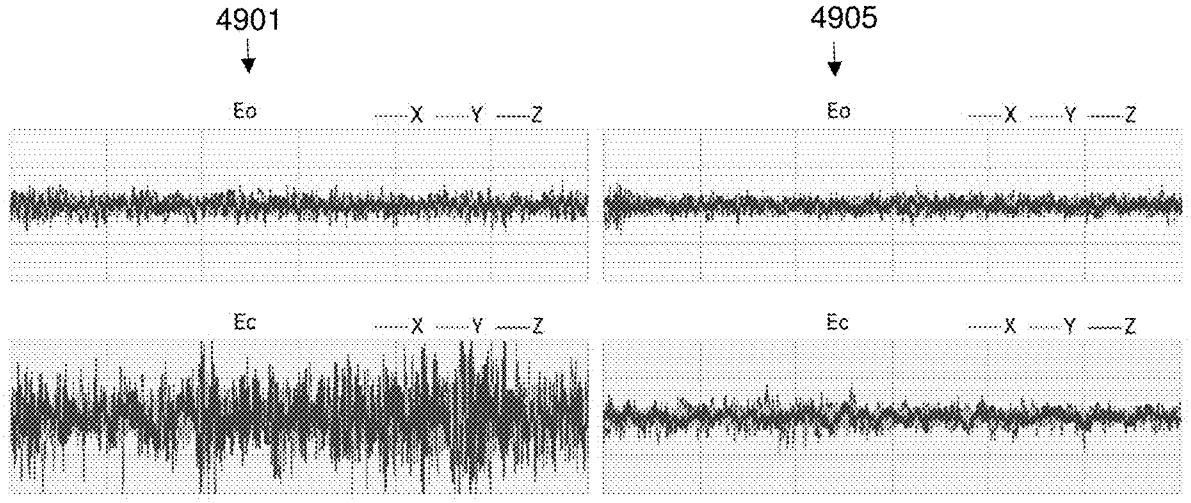
FIG. 49 shows example eyes open (Eo) and eyes closed (Ec) PHYBRATA time series signals for a study participant measured prior to the first VST treatment session and following the $18^{th}$ VST treatment session.

FIG. 49 presents example eyes open (Eo) and eyes closed (Ec) PHYBRATA time series signals that reveal significant improvements in postural stability for a selected study participant measured prior to the first VST treatment session 4901 and following the $18^{th}$ VST treatment session 4905.

Figure 50:
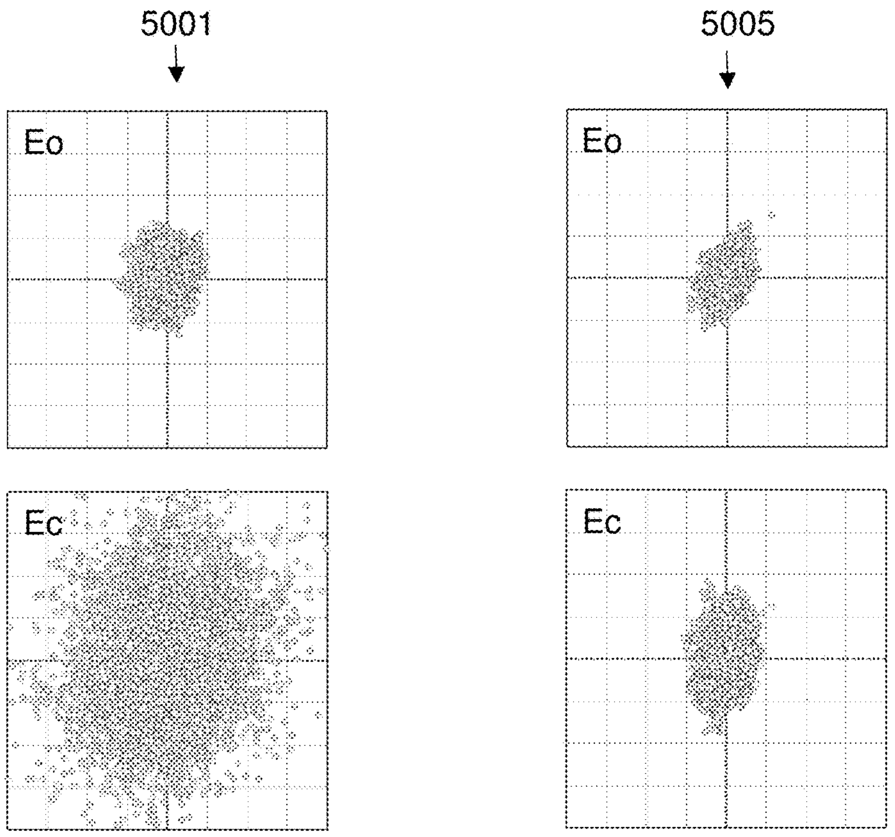
FIG. 50 shows example Eo and Ec PHYBRATA spatial scatter plots for a study participant measured prior to the first VST treatment session and following the 18th session.

FIG. 50 presents example eyes open (Eo) and eyes closed (Ec) PHYBRATA spatial scatter plots that reveal significant improvements in postural stability for the selected study participant measured prior to the first VST treatment session 5001 and following the $18^{th}$ session 5005.

Figure 51:
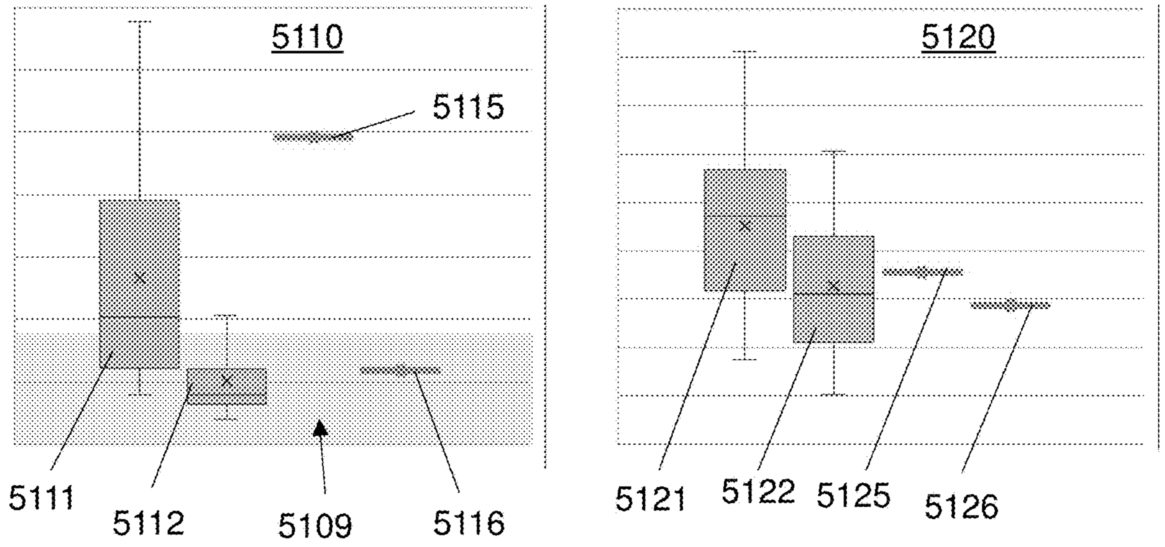
FIG. 51 shows changes in standing balance and walking stability from the beginning to the end of the 18-session VST treatment for the same study participant as in FIGS. 49 and 50, compared to changes for all 32 participants as a group.

FIG. 51 illustrates how both standing balance and walking stability changed from the beginning to the end of the 18-session VST treatment. The graphs 5110, 5120 include group data from all 32 participants in the pilot study in the box charts on the right, showing the individual results for the selected study individual participant. The balance and walking test scores are both derived from PHYBRATA sensor data, which is used to measure how well the vestibular system can keep the head steady during both stationary and moving tasks.

The data plots compare the selected study participants' balance and gait performance to the group's results at the start and end of the VST treatment, with lower PHBRATA powers (y-axis) indicating improvements for both balance and gait.

Graph 5110 shows results of the balance test with eyes closed (Ec). Box chart 5111 shows results for the group before the start of the VST treatments and box chart 5112 shows results for the group after the completion of the VST treatments. Data point 5115 shows the selected study participant's Ec results before VST treatments and data point 5116 shows the selected study participant's Ec results after the VST treatments. As can be easily seen in graph 5110, the selected study participant's Ec balance improved significantly as a result of the VST treatments, moving well into the grey shaded area 5109 (below the 0.89 biomarker) for the Ec balance test which highlights the target low fall risk range.

Graph 5120 shows results of the gait tests. Box chart 5121 shows results for the group before the start of the VST treatments and box chart 5122 shows results for the group after the completion of the VST treatments. Data point 5125 shows the selected study participant's gait test results before VST treatments and data point 5126 shows the selected study participant's gait test results after the VST treatments. As can be easily seen in graph 5120, the selected study participant's gait test results also improved as a result of the VST treatments. A gait test target low fall risk range corresponding to low fall risk similar to the grey shaded area 5109 of Graph 5110 could also be derived.

Figure 52:
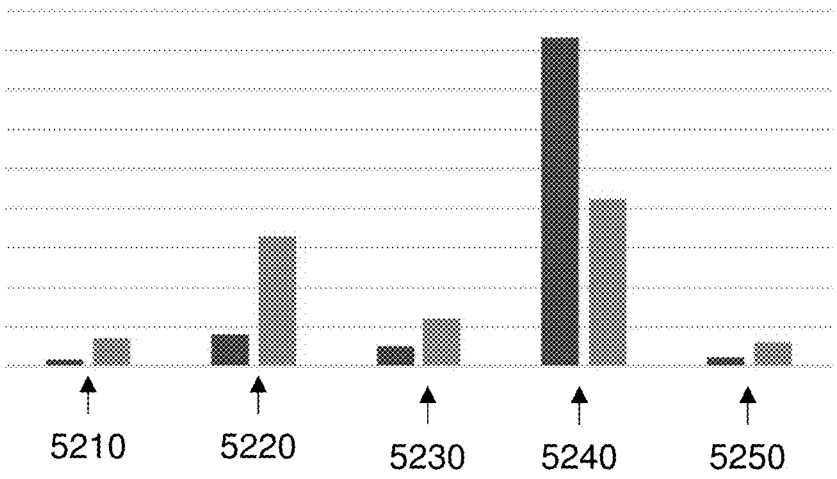
FIG. 52 shows example sensory reweighting plots for the same participant as above prior to the first VST treatment session and following the 18th VTS treatment session.

FIG. 52 presents sample sensory reweighting plots for the same selected study participant as above prior to the first VST session (blue bars—left bar of each pair) and following the $18^{th}$ VTS treatment (orange bars—right bar of each pair). Bars 5210 show the visual contribution to balance, bars 5220 show the vestibular contribution to balance, bars 5230 show the CNS contribution to balance, bars 5240 show the proprioceptive contribution to balance, and bars 5250 show the VCR contribution to balance. The results demonstrate that the balance and gait improvements result from a significant restoration of vestibular balance control, which also enables decreased reliance on proprioception, essentially reversing the effects of age-related vestibular loss.

Figure 53:
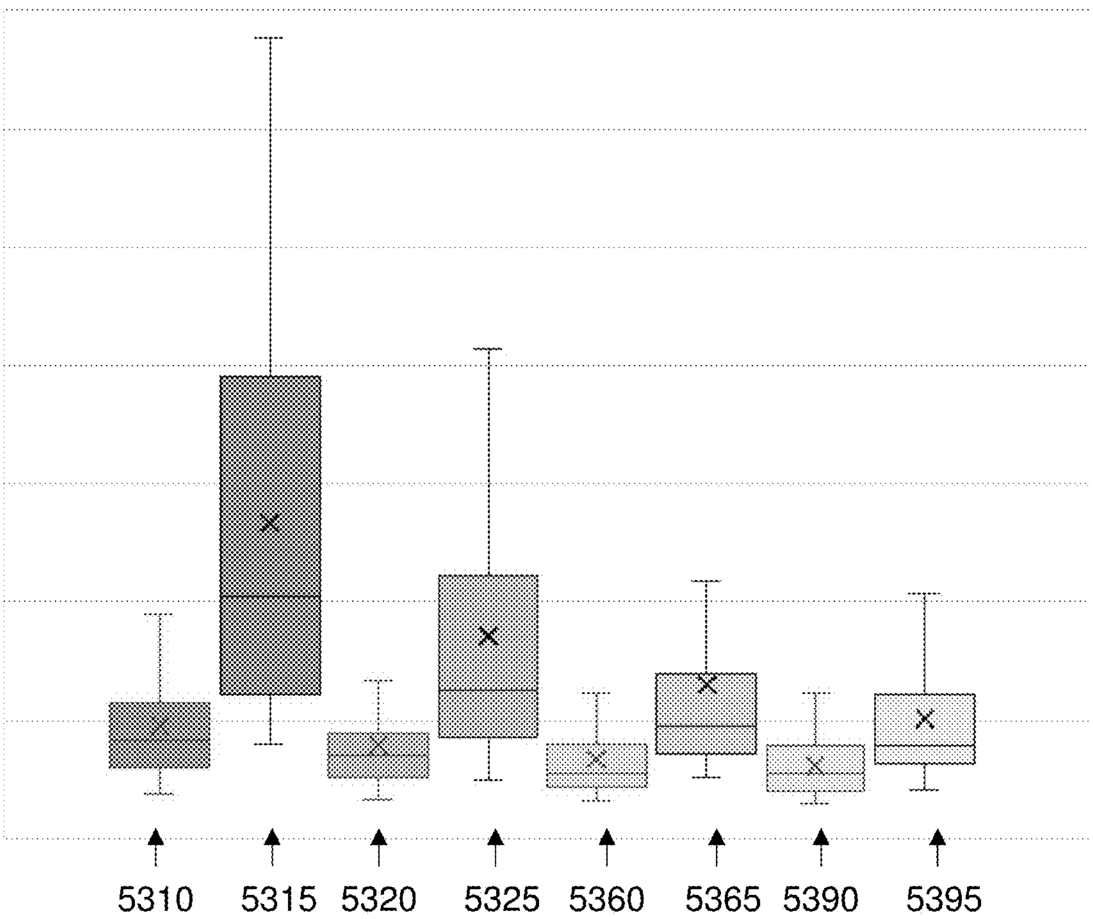
FIG. 53. shows postural stability for the study participants as a group measured using a PHYBRATA sensor throughout the 18-session VST treatment.

FIG. 53 demonstrates significant improvements in postural stability for the study participants as a group measured throughout the 18-session VST treatment. The y-axis shows PHYBRATA power. Box chart 5310 shows Eo tests and box chart 5315 shows Ec tests from before the first VST session. Box chart 5320 shows Eo tests and box chart 5325 shows Ec tests from after the second VST session. Box chart 5360 shows Eo tests and box chart 5365 shows Ec tests from after the sixth VST session and box chart 5390 shows Eo tests and box chart 5395 shows Ec tests from after the completion of the 18-session VST treatments.

Figure 54:
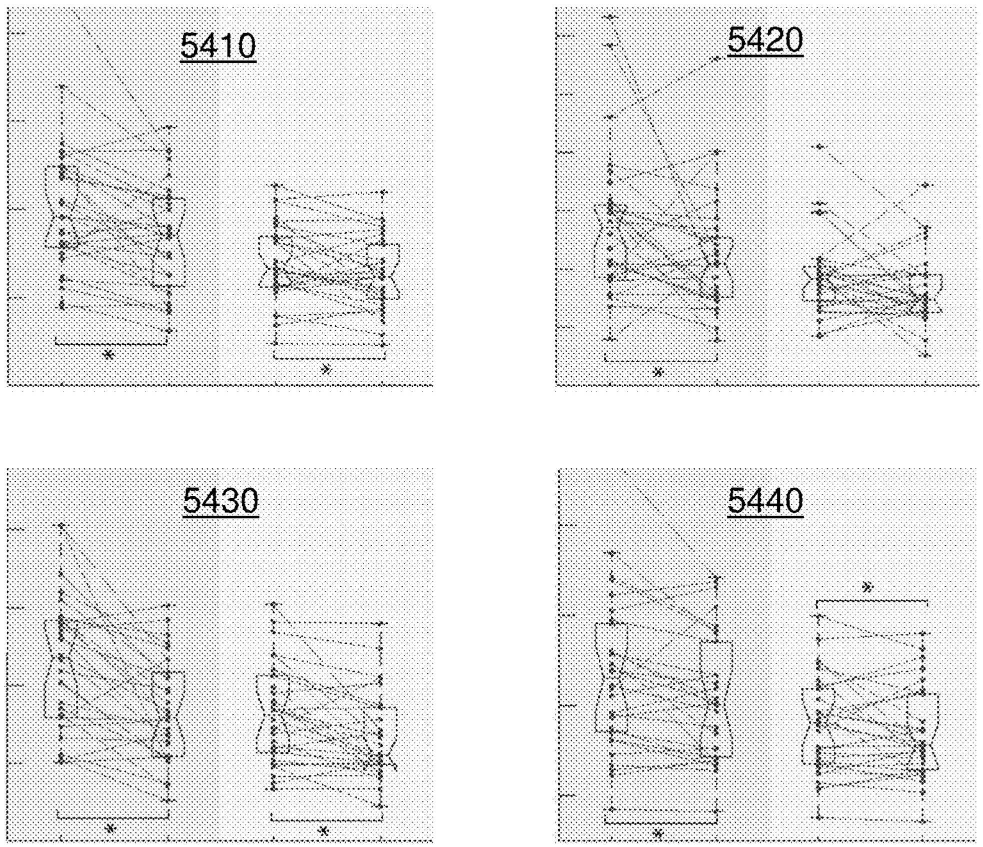
FIG. 54. shows gait stability for the study participants as a group measured at the beginning and the end of the 18-session VST treatment using a PHYBRATA sensor on the head and accelerometers on the feet.

FIG. 54 demonstrates significant improvements in gait stability for the study participants as a group measured throughout the 18-session VST treatment. Chart 5410 shows total power of the PHYBRATA data, chart 5420 shows forward power, chart 5430 shows lateral power, and chart 5440 shows vertical power. The left side of each chart 5410, 5420, 5430, 5440 show results from a 20 meter (m) test while the right sides show results from a 7.6 m test. Each pair of box charts show the results from before the VST on the left and the results after completion of the 18-session VST treatment on the right. Gait biomarkers derived from the head-mounted IMU were shown to be more sensitive to EVS-induced performance recovery than standard gait metrics derived from IMUs attached to the feet or body. EVS treatment significantly reduced head acceleration power across both distances, with the largest reductions in the lateral direction. Variability in step time and stride width decreased during 20 m walking, while 7.6 m trials primarily showed reductions in head power. These findings indicate that head-based biomarkers are sensitive to EVS-induced improvements even in short clinical walking tests, whereas longer walking distances are required to capture changes in stride-to-stride gait parameters.

Figure 55:
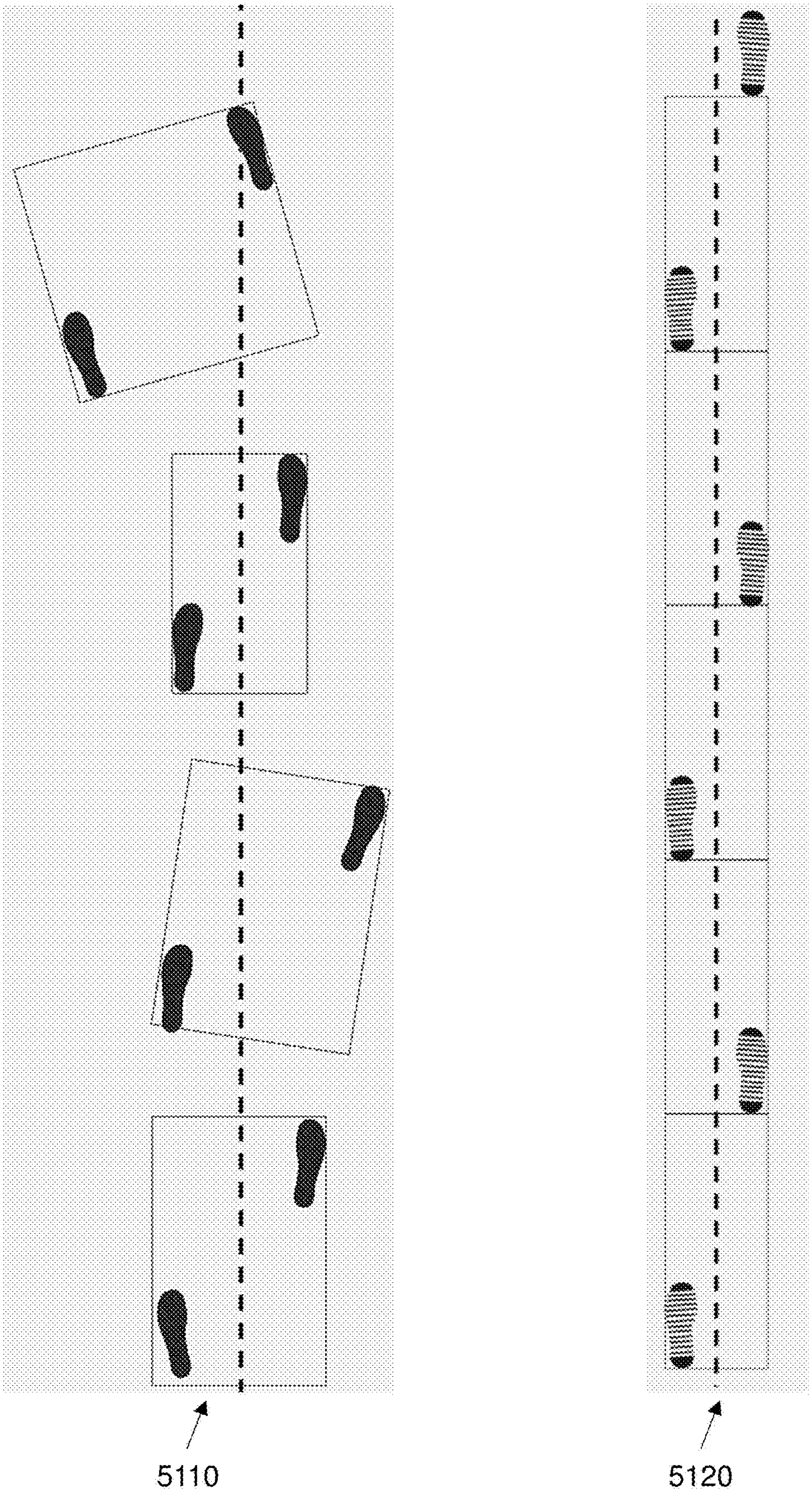
FIG. 55 illustrates improved gait stability for the study participants as a group measured before and after the 18-session VST treatment.

FIG. 55 further illustrates the improvements in gait stability for the study participants as a group measured throughout the 18-session VST treatment. While quantitative changes are not shown, gait tests were given to study participants who had finished an 18-session VST treatment. By the end of the treatment, the patients were walking at a faster speed with a more linear trajectory (lower VGH). They took longer strides with more regular stride length and a narrower and more regular stride width. They also spent less time with the foot flat on the ground between toe strike and heel lift.

Figure 56:
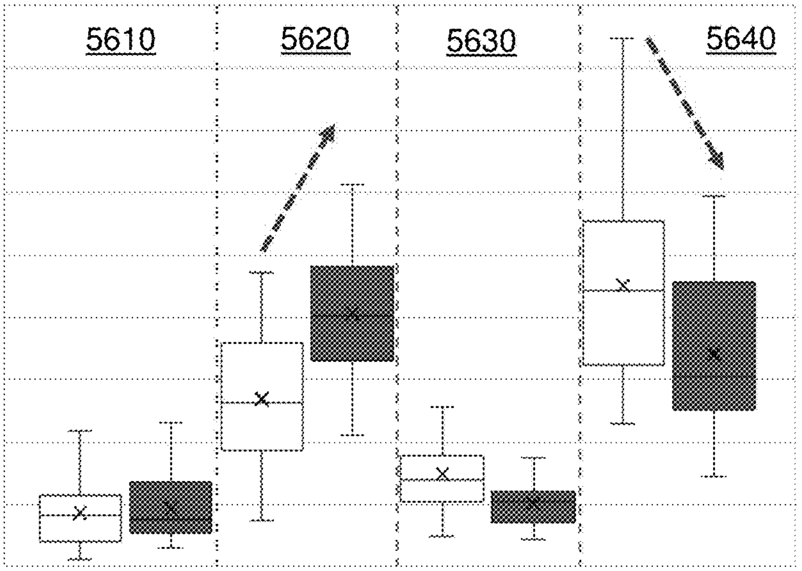
FIG. 56 shows sensory reweighting plots for older adults before and after completing the 18-session VST balance restoration treatment.

FIG. 56 shows sensory reweighting plots for the study participants as a group. The white boxes show the sensory reweighting for the study participants before the 18-session VST therapy, and the dark boxes show the sensory reweighting for the study participants after completion of the 18-session VST therapy. Section 5610 shows the visual contribution to balance, section 5620 shows the vestibular contribution to balance, section 5630 shows CNS contribution to balance, and section 5640 shows the proprioceptive contribution to balance. These results reveal that the observed improvements in balance and gait and reductions in fall risk are accompanied by a significant restoration of vestibular balance control that is offset by decreased reliance on proprioceptive balance control, essentially reversing the effects of age-related vestibular loss.

Figure 57:
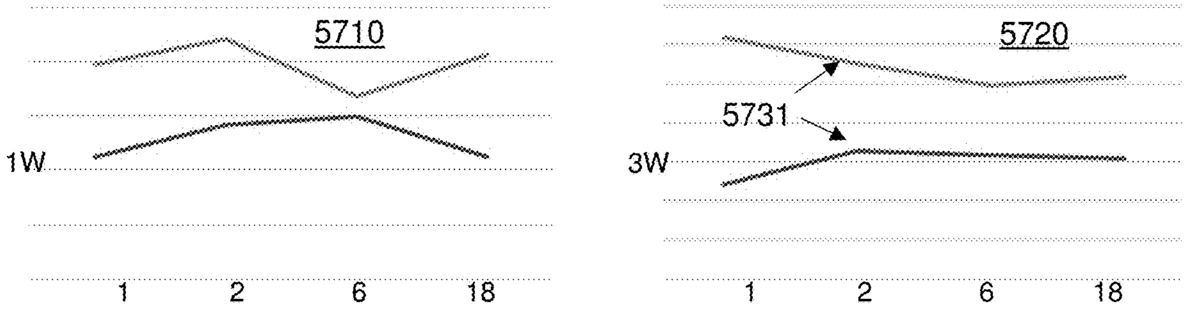
FIG. 57 shows PHYBRATA power for 2 non-responders measured throughout the 18-session VST treatment.
Figure 58:
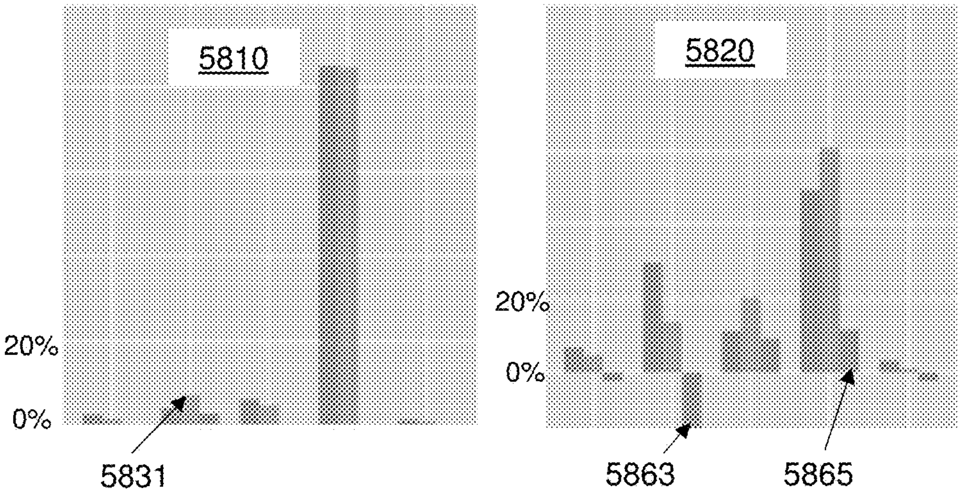
FIG. 58 shows sensory reweighting data measured for the 2 non-responders prior to the initial VST treatment session.

FIG. 57 and FIG. 58 show that PHYBRATA balance and sensory rebalancing biomarkers can be used to screen out non-responders in the 1st two treatment sessions, which limits costs and unproductive time for payers, providers, and patients alike. Graph 5710 in FIG. 57 shows the Eo results for the two non-responders before the first session, after the second session, after the sixth session and after completion of the 18 sessions. Graph 5720 show the Ec results for the two non-responders before the first session, after the second session, after the sixth session and after completion of the 18 sessions.

FIG. 58 shows sensory reweighting 5810 for the first non-responder and sensory reweighting 5820 for the second non-responder. Each group of bars show Eo on the left in blue, Ec in the middle in green, and Ec-Eo on the right in red. The 5 groups of bars represent, from left to right, the visual contribution to balance, the vestibular contribution to balance, the CNS contribution to balance, the proprioceptive contribution to balance, and the VCR contribution to balance.

Non responders are characterized in the first two treatment sessions by eyes closed (Ec) PHYBRATA powers above 3 Watts 5731, vestibular sensory reweighting contributions less than 10% 5831, or a large decrease in the vestibular sensory reweighting contributions from eyes open (Eo) testing to Ec testing 5863 that is accompanied by a large increases in proprioceptive balance control 5865.

Figure 59:
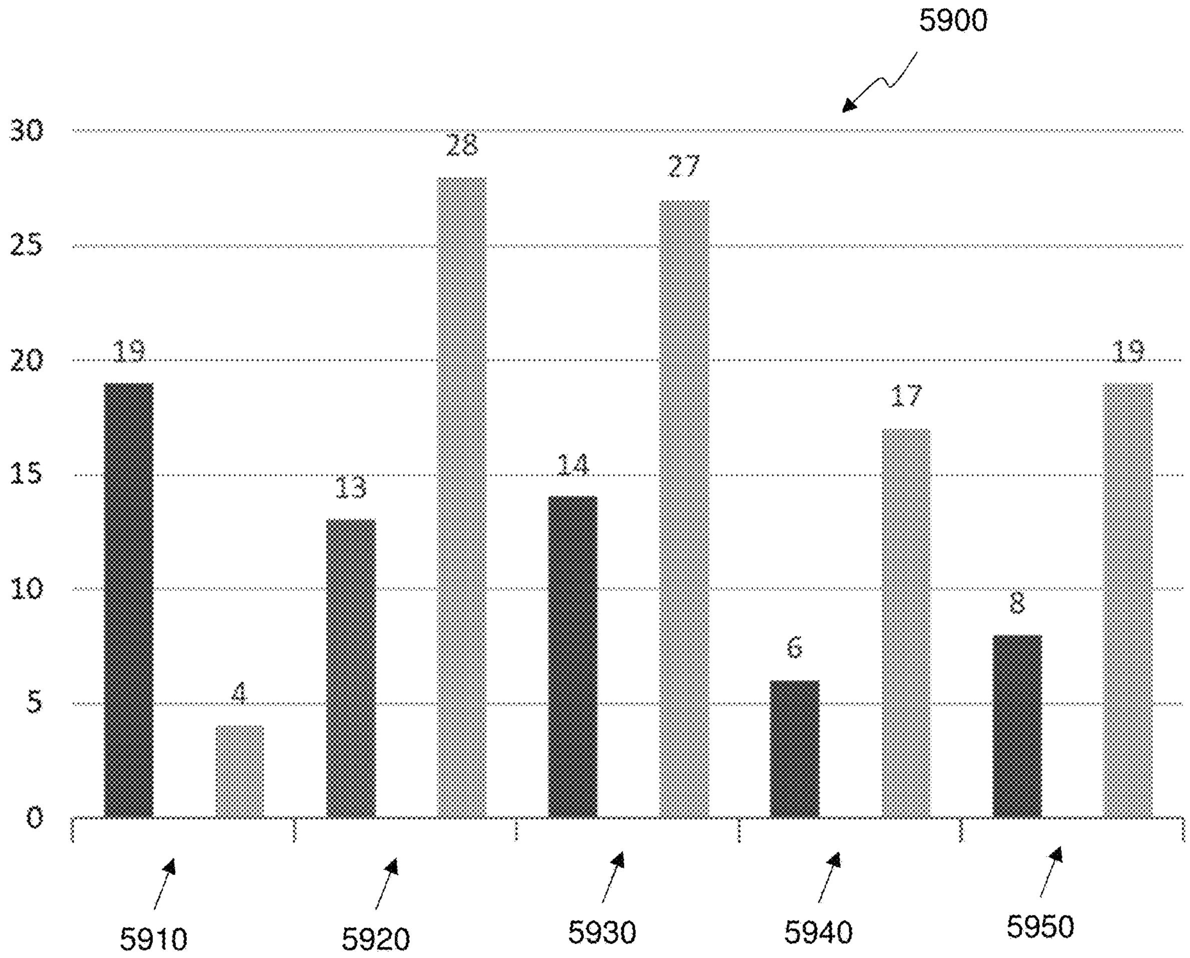
FIG. 59 summarizes changes in fall risk and balance performance measures for 32 pilot participants in response to the 18-session VST treatment.

FIG. 59 summarizes results of the additional balance performance tests and fall risk assessments for the 32 participants who completed the pilot. Graph 5900 shows the results from before VST therapy in red (on the left) and the results after completion of VST therapy in green (on the right), with the y-axis being the number of participants. The number of participants able to stand for a full minute on a foam balance pad with eyes closed 5930 increased from 14 to 27. Those capable of standing on one leg for 10 seconds with eyes open on a hard floor increased from 6 to 17 (left leg) 5940 and from 8 to 19 (right leg) 5950. The number of participants classified as high fall risk was reduced from 19 to 4 after treatment 5910 and thus, the number of participants shown that were classified as low fall risk 5920 increased from 13 to 38. These results highlight the opportunity to combine more detailed and quantitative balance testing with targeted interventions to mitigate adverse health outcomes.

No adverse events were reported during the above VST pilots. Many participants reported immediate improvements in balance and walking within the first two treatment sessions. The two most common improvements are feeling more secure walking down stairs and hiking over uneven terrain and having enhanced ability to perform exercises that require standing on one leg. Physical therapists involved in VST pilot deployments have noted that the VST-induced improvements in vestibular control, balance, and mobility enabled patients to progress to more advanced and challenging physiotherapy activities that were previously limited by unstable posture or fear of falling. These mobility gains also extend to cognition (e.g., increased dual-task capacity without instability) and enhanced psychological well-being, with reduced fear of falling leading to a greater willingness to engage. This represents a significant reversal of the typical decline in mobility and social engagement experienced by many older adults.

These results demonstrate that PHYBRATA digital biomarkers enabled home care providers to carry out rapid objective assessment of changes in balance, gait, fall risk, and sensory reweighting in older adults before, during, and after a multi-session EVS treatment protocol.

Neuromotor decline triggers impairments to both static balance and dynamic balance which in turn increases fall risks. Rapid and simple tests that can provide clinically useful biomarkers of both static balance and dynamic balance impairments are thus important to diagnose and treat degraded neuromotor performance. As illustrated above, PHYBRATA balance biomarkers enable rapid, real-time assessment of individual changes in balance performance, sensory reweighting, and fall risk. Many metrics for dynamic balance performance have been proposed using data from sensors mounted on different parts of the body. Several gait biomarkers demonstrate significant correlations with PHYBRATA balance markers and can be derived from rapid and simple gait tests with a duration as short as 3 minutes or less, using inertial motion unit (IMU) sensors mounted on the head, on the body, or on the feet. These gait biomarkers include, but are not limited to:

- Absolute values of gait heading (GH) and magnitude of variations in gait heading (VGH), measured in degrees.
- Absolute values of stride velocity (SV) and magnitude of variations in stride velocity (VSV), measured in meters per second.
- Absolute values of lateral foot deviation (LFD) and magnitude of variations in lateral foot deviation (VLFD), measured in meters.
- Absolute values of external rotation of the feet (ERF) and magnitude of variations in the external rotation of the feet (VERF) about the vertical axis, measured in degrees.
- Variations in the external rotation of the feet about the vertical axis per meter of lateral foot deviation, which we refer to here as variations in gait steering (VGS), measured in degrees per meter.

During a 3-minute walking test, the above gait biomarkers demonstrate much higher correlation with PHYBRATA balance biomarkers such as Ec and much higher sensitivity in identifying increasing gait instability with increasing age than other standard gait metrics that have previously been reported. The variability in gait heading (VGH), for example, measures the degree to which an individual is unable to maintain a straight-ahead trajectory while walking, indicative of degraded vestibular control that results in a walking trajectory with a greater degree of weaving or wandering toward the left or right when measured over multiple steps. Similarly, the variability in gate steering (VGS) measures the degree to which this inability to maintain a straight-ahead trajectory while walking due to degraded vestibular control also results in greater lateral separation of the feet in order to maintain a wider and more stable base of support. The present invention discloses balance and gait biomarkers that together enable statistically significant assessments of both static and dynamic balance impairments and response to treatment interventions such as EVS with a simple balance test as short as 2 minutes or less and a simple walking test as short as 3 minutes or less. Alternative gait assessment metrics typically require much longer measurement times of >10 minutes to many hours, which are not compatible with simple and rapid testing in many senior living environments. These alternative gait assessment metrics also do not demonstrate significant correlations with PHYBRTA balance metrics such as Ec.

The NEURVESTA system 3300 can enable a VST treatment protocol for therapeutic treatment of patients with Benign Paroxysmal Positional Vertigo (BPPV), a common vertigo condition caused by otoconia migrating and becoming lodged in the semicircular canals. Patients with BPPV typically report symptoms such as short bouts of intense dizziness, spells of spinning dizziness that may be brought on by going from sitting to lying down, dizziness from turning over in bed, being very sensitive to sound when having a headache, dizziness caused by placing their head in a certain position, an unsteadiness on their feet, being anxious, and feeling dizzy almost daily or even all of the time. It has been found that five consecutive days of swsEVS treatment is sufficient to reduce the BPPV-induced balance impairment back to healthy levels.

Modelling of EVS indicates that the swsEVS stimulation at a current level of 350 μA will generate an electric field on the order of 10-20 milli-Volt per meter (mV/m) in the peripheral vestibular organs. This electric field strength is sufficient to generate a pressure difference exceeding 100 μPa (micro-Pascals) within the endolymph fluid in the vestibular balance organs, which is sufficient for swsEVS to deflect the motion sensing hair cells (stereocilia) and flush displaced otoconia from the semicircular canals by inducing stochastic Brownian motion.

Figure 60:
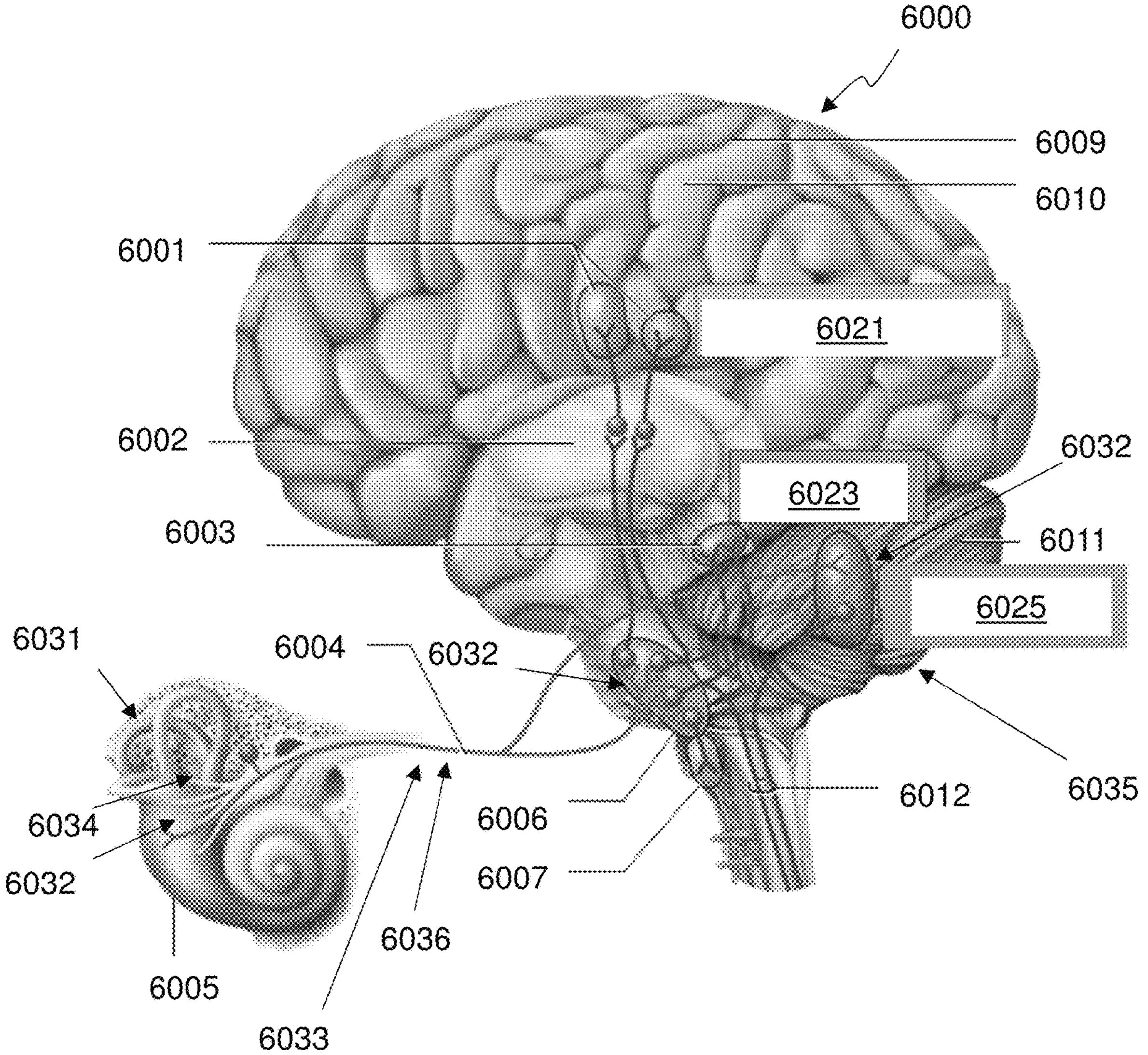
FIG. 60 shows an image of a human brain and vestibular apparatus with several different areas identified.

FIG. 60 shows an image of a human brain 6000 and vestibular apparatus 6005 with several different areas identified. An awareness of spatial orientation and movement 6021 is controlled by the vestibular cortex 6001. Compensatory eye movements 6023 are controlled by the nuclei for eye movement 6003. Motor control 6025 is handled by the cerebellum 6011. Also shown are the thalamus 6002, the reticular formation 6007, the central sulcus 6009, the vestibulospinal tracts 6012, and the postcentral gyrus 6010. A vestibular apparatus 6005 is located near each ear and is connected to the vestibular nuclei 6006 by the vestibulocochlear nerve 6004.

Neurogenesis in the vestibular nuclei 6006 plays a key role in development and plasticity of neuromotor and neurocognitive processes. Neurogenesis is enabled by neural stem cells located primarily in specialized regions of the brain, called neurogenic niches, such as the subgranular zone of the dentate gyrus and the subventricular zone of the lateral ventricles.

However, other brain regions such as the hypothalamus and the vestibular nuclei 6006 have subsequently been discovered with a pool of neural stem cells. Following unilateral loss of vestibular function in laboratory experiments, quiescent neural stem cells present in the vestibular nuclei react to restore the posturolocomotor functions necessary for survival. Electrical stimulation of the vestibular system following loss of vestibular function triggers cell proliferation in the deafferented vestibular nuclei, even when the vestibular functional loss alone is not sufficient to activate the vestibular neurogenic niche.

The persistent increase in postural stability or gait stability in the present invention comprises one or more EVS-induced neuroplastic mechanisms, including:

- Regeneration of vestibular hair cells 6031;
- Increase in synaptic gain 6032;
- Increase in afferent vestibular nerve conductivity/excitability 6033;

Removal of otoconia from semicircular canals 6034;

Increase in central neural integration and processing of sensory signals (vestibular, visual, somatosensory) for motor control 6035; or Increase in efferent feedback from CNS to vestibular inner ear 6036 (possibly reflecting the changes listed above).

Note that the first four mechanisms are in the peripheral vestibular apparatus and the final two are in the CNS. The results described above demonstrate that a single 15-minute application of sub-threshold stochastic EVS induces significant sensory reweighting and reduction of age-related balance impairments that persist after completion of EVS therapy. The EVS-induced balance enhancements are larger when postural stability is challenged, and a trend toward larger relative balance improvements at lower ages is observed. These changes not only stabilize balance and movement but also enhance neuromotor control and sensory reweighting.

Figure 61:
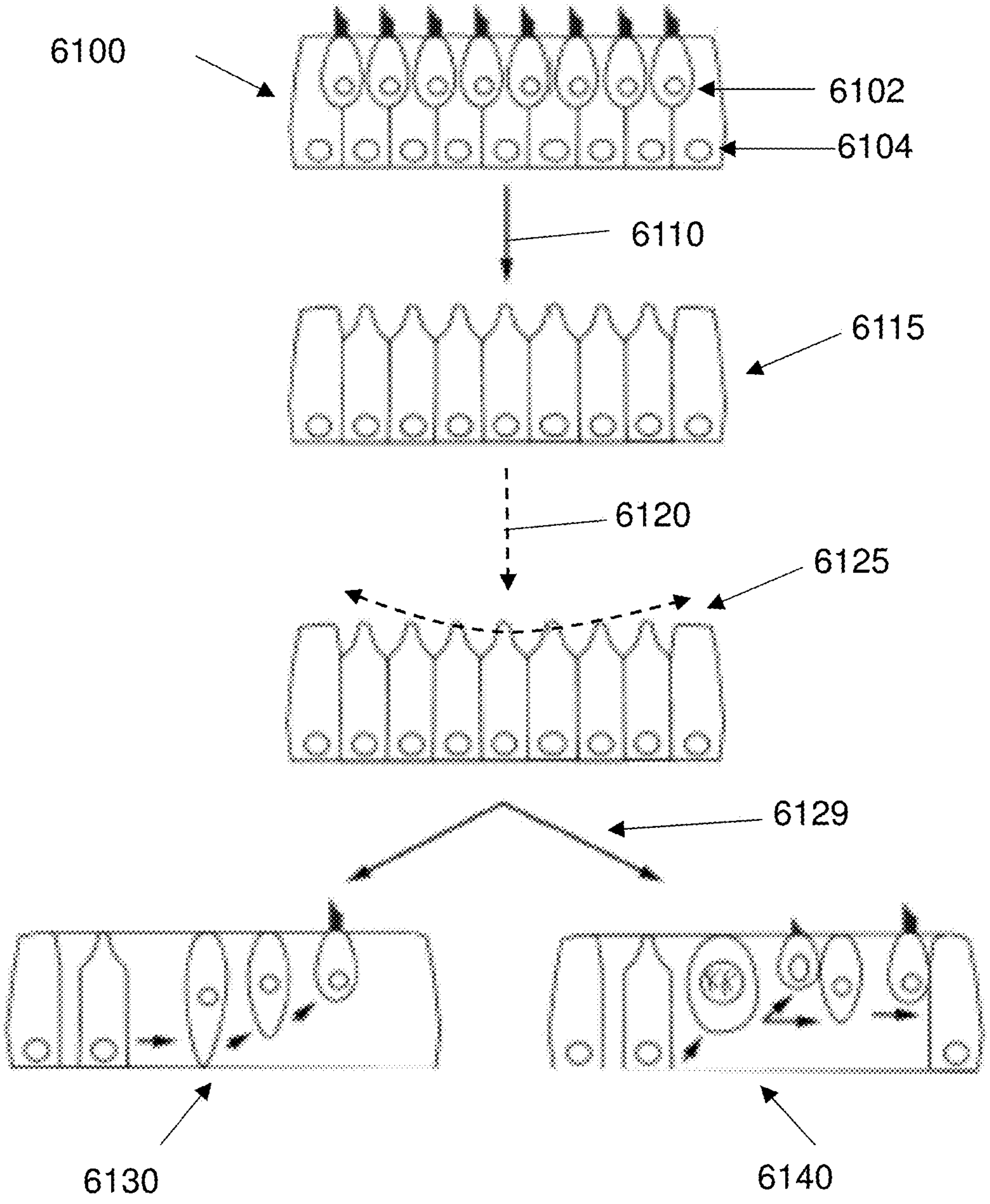
FIG. 61 illustrates vestibular hair regeneration.

FIG. 61 illustrates vestibular hair regeneration, which is one of the neuroplastic mechanisms that can be induced by EVS. Healthy cells lining the vestibular apparatus 6100 include the hair cell layer 6102 and supporting cell layer 6104. Through aging, injury, or other causes, hair cell death 6110 may occur leaving only the undifferentiated supporting cells 6115.

EVS may then stimulate 6120 the cells 6115 and cause hair cell regeneration 6129 via direct trans-differentiation 6130 or division and trans-differentiation 6140 of the calls 6115 in one or more ways, such as, stochastic electric field stimulation of the cells 6125, induced direct stochastic electrical enervation of undifferentiated supporting cells 6125, stochastic endolymph fluid motion 6125, and/or induced stochastic electromechanical stimulation of undifferentiated supporting cells via electrohydrodynamic endolymph fluid motion 6125. Any of these phenomena may also be considered neurogenesis in the peripheral vestibular system.

It has also been discovered that proteomic blood biomarkers may be indicative of swsEVS-induced neurogenesis. Blood biomarkers may be utilized in conjunction with PHYBRATA biomarkers to further refine the discovery and delivery of swsEVS waveforms and treatment protocols to maximize the magnitude of the therapeutic benefits, minimize the duration of individual treatment sessions or the required number of treatment sessions, and maximize the duration over which the therapeutic benefits persist after treatment has been completed. Multiple candidate biomarkers are present following multiple stages of restoration of peripheral or central vestibular function. Biomarkers that can be identified with standard assessment panels from blood samples as small as 25 μL may be utilized in some treatment protocols. Candidate biomarkers include, but are not limited to:

Neuro-growth factor biomarkers VEGF-A, VEGF-B, and VEGF-C.

TNF inflammatory factors TNF-α and Nf-Kb: structural damage to the peripheral vestibular system induces degeneration of vestibular nerve afferents, releasing inflammatory signals into the vestibular nuclei.

SOX2 and GFAP: These transcription factors and glial proteins colocalize in cells that are reactive to lesions in the vestibular nuclei.

Nestin: This marker indicates the presence of stem cells.

BrdU: This marker indicates cell proliferation.

NeuN: This marker indicates neuronal differentiation.

Figure 62A:
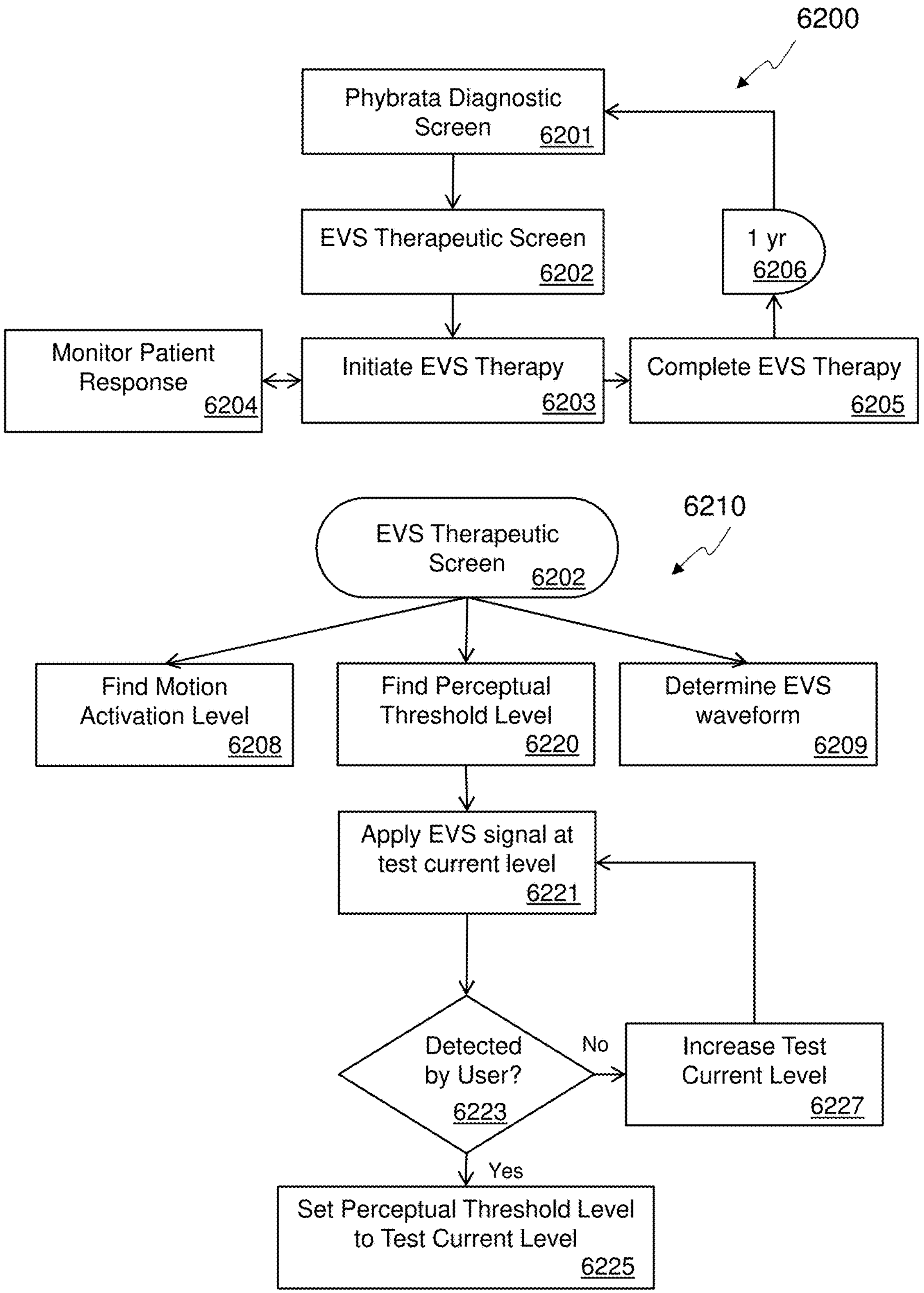
FIG. 62A, FIG. 62B, and FIG. 62C show flowcharts illustrating methods of using the NEURVESTA system.
Figure 62B:
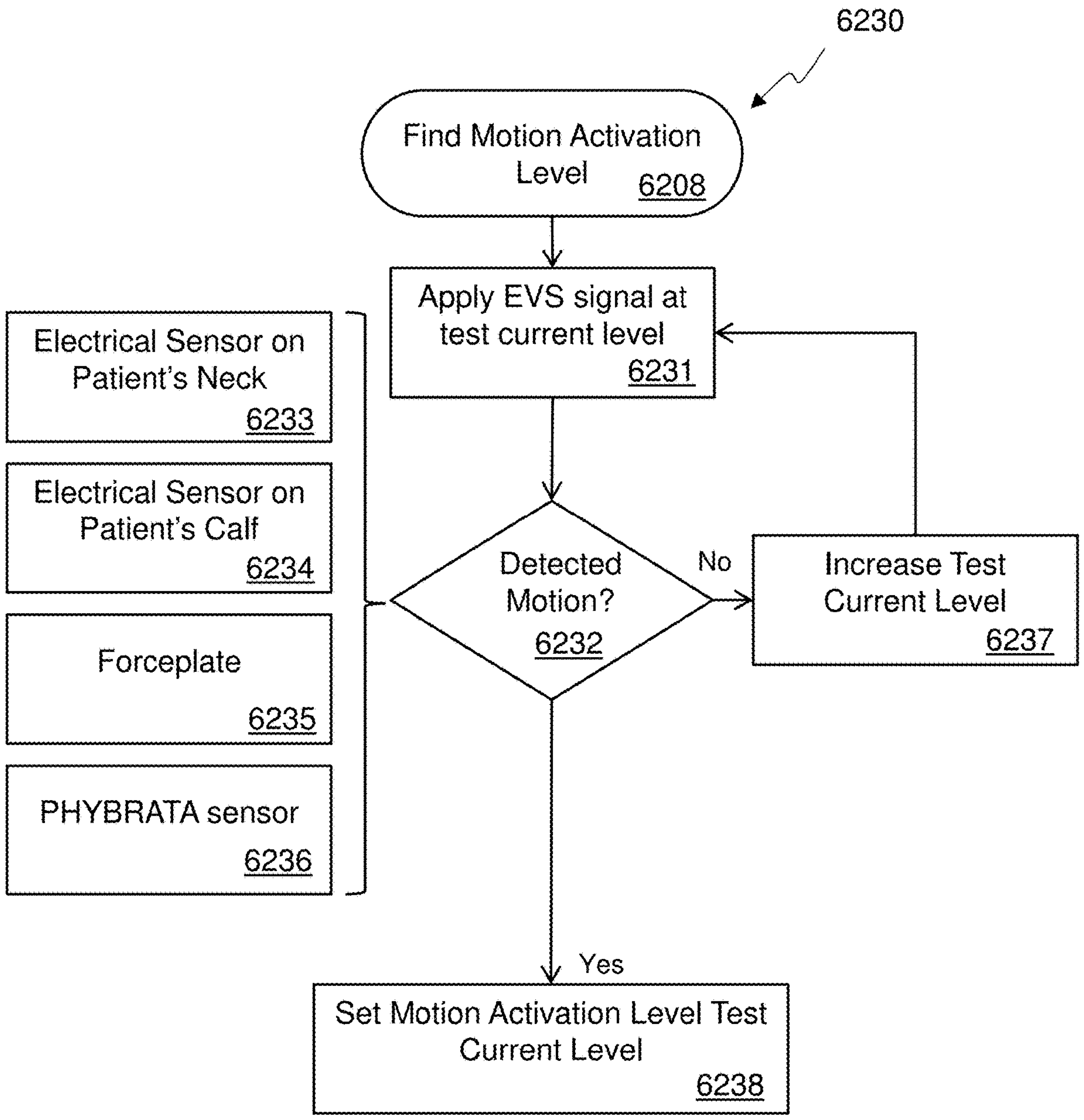
Figure 62C:
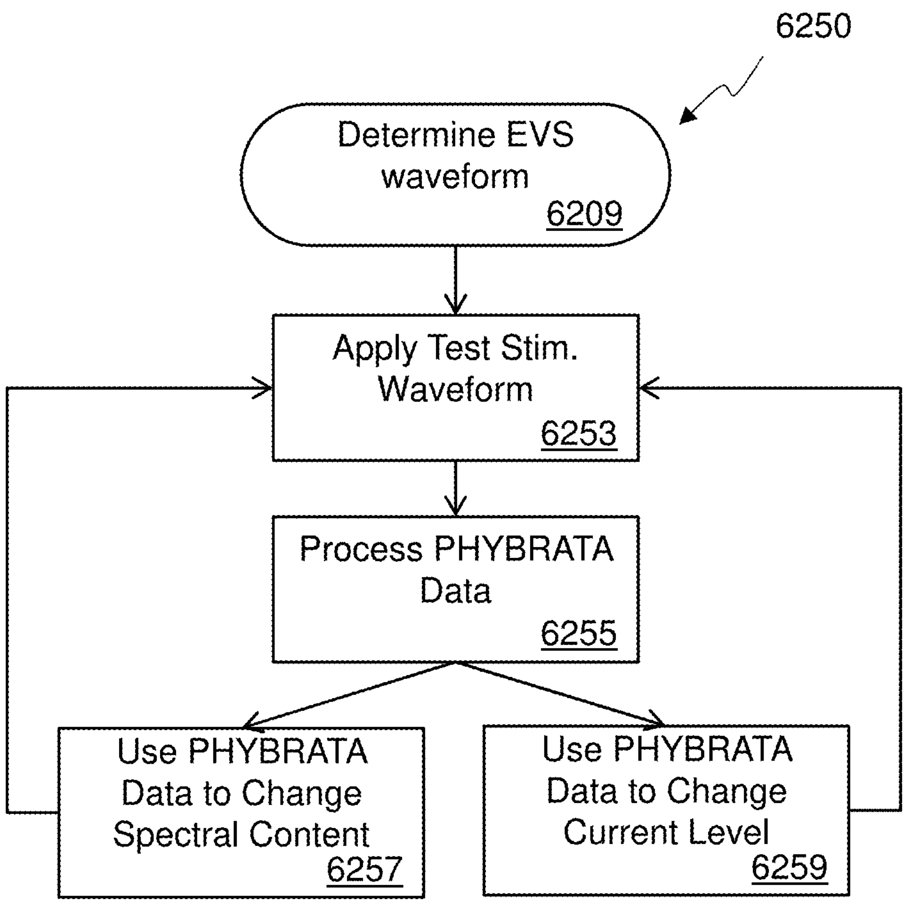

FIG. 62A, FIG. 62B, and FIG. 62C show flowcharts illustrating methods of using the NEURVESTA system. A method for providing VST treatment is shown in flowchart 6200 in FIG. 62A. The combination of PHYBRATA diagnostics and EVS therapeutics, including as separate devices or their integration into the same device, allows clinicians to first utilize the PHYBRATA physiological diagnostic sensing function to screen for multiple physiological system impairments, including impairments to the vestibular balance system. As such, the NEURVESTA device may be utilized for routine screening 6201 for balance impairments. The initial screening 6201 can include any number of trials with eyes open, eyes closed, feet together, feet apart, solid footing, or unstable footing (e.g., a foam pad) and can take any period of time, but in one example a screening may include two 60 second trials, one with eyes open and the second with eyes closed. A baseline blood biomarker sample may also be collected. The screening 6201 may identify that the patient has impaired balance or that their balance is normal. It may also identify specific physiological system impairments, such as visual, vestibular, CNS, proprioceptive, or VCR impairments.

Thus, the method 6200 of providing restoration of vestibular function of a user may include performing the evaluation of the user's balance before the plurality of treatment sessions. The swsEVS waveform may be created based on the evaluation of the user's balance, based on another therapeutic screen, based on demographic data for the user, of from data acquired from a large population of users to generate a standardized swsEVS waveform.

The evaluation of the user's balance may include affixing a PHYBRATA sensor to a head of the user, collecting first data from the PHYBRATA sensor from the user while standing with eyes of the user open, collecting second data from the PHYBRATA sensor from the user while standing with the eyes of the user closed, and analyzing the first data and the second data to determine spectral content for the swsEVS waveform. It may further include collecting third data from the PHYBRATA sensor from the user while standing with the eyes of the user open with feet of the user spread apart, where the first data is collected with the feet of the user close together, and collecting fourth data from the PHYBRATA sensor from the user while standing with the eyes of the user open with the feet of the user spread apart, where the second data is collected with the feet of the user close together. The first data, the second data, the third data, and the fourth data may then be analyzed to determine spectral content for the swsEVS waveform. In addition or alternatively to collecting third and fourth data with the user's feet spread apart, the method may include collecting fifth data from the PHYBRATA sensor from the user while standing on a foam pad with the eyes of the user open, wherein the first data is collected while from the user is standing on a solid surface, collecting sixth data from the PHYBRATA sensor from the user while standing on the foam pad with the eyes of the user closed, where the second data is collected while the user is standing on the solid surface, and analyzing the fifth data, and the sixth data, along with some combination of first, second, third and fourth data, to determine spectral content for the swsEVS waveform.

If a vestibular impairment is identified, the NEURVESTA device may then be used for a therapeutic screen 6202. The therapeutic screen 6202 is optional as a standardized EVS waveform may be used in some case. The therapeutic screen 6202 can include any number of trials with eyes open, eyes closed, feet together, feet apart, solid footing, or unstable footing (e.g., a foam pad) and can take any period of time, and providing any number of different EVS waveforms but in one example the therapeutic screen 6202 may take 10 minutes, with 5 different EVS waveforms used for a 60 second trial with eyes open, and a 60 second trial with eyes closed. One or more blood biomarker samples may be collected and analyzed to determine accompanying degree of vestibular neurogenesis triggered by optimized swsEVS parameters.

The therapeutic screen 6202 allows clinicians to identify the EVS stimulation parameters that optimize balance improvement. Optimal EVS waveforms, current levels, and frequencies may be different for each patient. The therapeutic screen 6202 may include scans to determine a motion activation level and/or a perceptual threshold level and the EVS waveform may be applied at a current level between the motion activation level and the perceptual threshold level. The therapeutic screen 6202 may allow for identification of the EVS stimulation parameters that optimize balance or gait improvement, including EVS current levels and frequencies, utilizing one or more PHYBRATA biomarkers. These PHYBRATA biomarkers are derived from spatial domain PHYBRATA data, time domain PHYBRATA data, frequency domain PHYBRATA data, and/or PHYBRATA sensory reweighting data.

The EVS waveform may be subthreshold wideband stochastic electrical vestibular stimulation (swsEVS) waveform. Subthreshold may be interpreted as being below a tactile sensation threshold or below a level that can induce subtle bodily motion. Thus, the swsEVS may be applied at a current level that is low enough to not induce detectable bodily motion by the user and/or applied at a current level that is imperceptible by the user (i.e. no tactile sensation or noticeable bodily motion. The perceptual threshold is observed to typically lie in the range 500-1000 μA.

A stochastic electrical signal has a noise-like spectrum that includes frequencies distributed across the range of frequencies, such as, but not limited to, 0 Hz to 600 Hz. Various implementations may use other frequency ranges such as 0-300 Hz or 0-25 Hz. While the stochastic electrical signal consists essentially of the frequencies in the range specified, other frequencies may be incidentally included, but the other frequencies outside of the specified range provide less power than frequencies within the band, such as less than 5% of the total power of the electrical signal. The stochastic waveform may be white noise, meaning that the power is uniformly distributed across its spectrum, or colored noise, meaning that some frequencies or frequency sub-ranges within the frequency spectrum of the signal are accentuated, attenuated, or even omitted. In some cases, the stochastic waveform may have a gaussian frequency distribution. In some implementations, the swsEVS waveform may include only specific frequency ranges in which PHYBRATA sensory reweighting data demonstrate the patient's significant change in vestibular performance, as will be discussed below.

In some implementations, the therapeutic screen 6202 may include determining the patient's EVS perceptual threshold by scanning the current applied at the EVS electrodes, for example in steps of 50 μA beginning at 100 μA and asking the patient to indicate when they are able to first perceive a sensation at the application site on their mastoid. An initial therapeutic current level may be selected based on the perceptual threshold, such as a current level of between 25% and 75% of the perceptual threshold although some implementations may use current levels outside of that range.

In some implementations, the therapeutic screen 6202 may include determining a maximum stochastic resonance response by scanning the current applied at the EVS electrodes, for example in steps of 50 μA mA beginning at a level equal to 10% of the patient's perceptual threshold, and monitoring the patient's vestibular balance performance improvement as indicated, for example, by spatial domain PHYBRATA acceleration data, time domain PHYBRATA acceleration and power data, frequency domain and time-resolved frequency domain PHYBRATA data, and/or PHYBRATA sensory reweighting data.

So, in some implementations, the therapeutic screen 6202 may include affixing a PHYBRATA sensor to a head of the user, applying a test stimulation waveform to the user at a test current level through the first electrode starting at an initial test current level, and increasing the test current level of the test stimulation waveform while monitoring an output of the PHYBRATA sensor. The treatment current level may then be based, at least in part, on the output of the PHYBRATA sensor, such as by determining at what current level the output power level of the PHYBRATA sensor has a local minimum. The swsEVS waveform may be applied to the user through the electrodes at the treatment current level during at least one treatment session of the plurality of treatment sessions.

EVS frequency buckets that maximize the patient's vestibular balance performance improvement may be determined by scanning the stochastic EVS current frequencies applied at the EVS electrodes, for example in buckets of width 0.2 Hz beginning at 0-0.2 Hz and ending at 24.8-25 Hz, or in buckets of width of 2 Hz from 0 to 300 Hz or 0 to 600 Hz, and monitoring the patient's vestibular balance performance improvement as indicated by one or more PHYBRATA data sources selected from spatial domain PHYBRATA acceleration data, time domain PHYBRATA acceleration and power data, frequency domain and time-resolved frequency domain PHYBRATA data, and PHYBRATA sensory reweighting data. Any range of frequencies may be used for the various buckets, including non-uniform frequency ranges, such as those discussed in relation to FIG. 6.

In at least one implementation, individual responses to a wide range of potential EVS stimulation parameters are assessed for large numbers of participants to identify one or more specific classes of EVS waveforms that deliver very large therapeutic benefits across a wide age range and a wide range of initial levels of balance impairment, without the need to personalize stimulation parameters at the outset of treatment or adapt stimulation parameters during treatment. A standard treatment protocol is then utilized in conjunction with a NEURVESTA wearable device optimized for the delivery of such a standard VST treatment protocol.

Clinicians may prescribe EVS therapy which is then initiated 6203 with the patient. The EVS therapy provided to the patient may include any number of treatment sessions over any period of time, depending on the circumstances, but for one non-limiting example, the EVS therapy may be provided as between 1 and 36 treatment sessions over a period of 12 weeks or less. As another example, the EVS therapy may include between 3 and 36 treatment sessions provided over a period of between 3 and 84 days. In some cases, a treatment session is provided to the patient on multiple consecutive days (e.g., 3 to 15 days) to start the therapy but may then decrease in frequency to one treatment session every 2 days or one per week. Each treatment session may include application of the electrical stimulation to the user through one or more electrodes of the NEUR- VESTA device for a period of time, such as for between 2 and 60 minutes. PHYBRATA data may be monitored while the EVS therapy is being administered, and in some cases, the EVS stimulation parameters may be changed in real time based on the PHYBRATA data captured during the treatment session. In some cases, a therapeutic screen 6202 may be performed between some treatments, such as at the half-way point through the therapy. Treatment sessions may be separated by any period of time, such as being separated by at least 60 minutes, occurring daily, being administered on weekdays only, or being separated by 1 or more days. In another scenario, a patient may wear the NEURVESTA device 3 times a week for 10-30 minutes during each session, during which the optimized EVS signal from Step 2 is applied. It may be common for the EVS therapy to consist of 15 to 20 treatment sessions provided over a period of 4 to 6 weeks with each treatment session including the application of electrical stimulation to the user for between 15 and 25 minutes through one or more electrodes attached to the head and/or neck of the user.

Single-session EVS therapeutic improvement may persist for 24-72 hours. Multi-session (e.g., 18 sessions over 4-6 weeks) therapeutic improvements may persist for at least 7 days after the final treatment sessions and up to 6 months or even longer. The ability to monitor the patient's response as the EVS is being applied and progress over time enables adaptive therapeutic treatments that are personalized to each patient's unique balance impairment profile at the outset of treatment and unique recovery trajectory as treatment progresses.

Vestibular performance improvement may be monitored 6204 over the length of the EVS therapy treatment to allow the clinician to continuously assess the patient's response to the therapy. Additional periodic blood biomarker samples may be collected and analyzed during and following treatment to determine accompanying degree and persistence of vestibular neurogenesis. In some cases, the clinician may adjust the EVS stimulation parameters prior to or following each therapeutic session to achieve continuing improvement or to increase the level of improvement. In some cases, a target level of vestibular performance improvement to be achieved over the multi-week duration of the EVS therapy treatment may be set to the level observed when the optimized EVS signal is applied in the initial therapeutic screening 6202.

If and when no further vestibular performance improvement is observed, or if a predetermined target level for parameters based on the PHYBRATA data is achieved, the EVS therapy treatment may be deemed to be completed 6205 and therapy sessions terminated. In other cases, the EVS therapy may be terminated upon completion of the predetermined number of treatment sessions 6205. Patients then undergo regular follow-up assessments 6201, such as annually 6206, and the NEURVESTA therapy treatment can be repeated as indicated.

In one implementation a swsEVS treatment protocol includes six weeks of treatment with 3 treatment sessions per week for a total of 18 treatment sessions. Each treatment session includes a two-minute PHYBRATA balance test before and after a 20-minute swsEVS treatment to quantify balance improvements in each session, cumulative balance improvements throughput the multi-session treatment, and eventual plateau in each patient's balance improvement. In some cases, each treatment session includes a PHYBRATA gait test before and after a 20-minute swsEVS treatment to quantify gait improvements in each session, cumulative gait improvements throughput the multi-session treatment, and eventual plateau in each patient's response.

Thus, a method of providing restoration of vestibular function of a user may include providing a plurality of treatment sessions to the user, where each treatment session includes affixing a first electrode on or near a mastoid of a user and applying a subthreshold wideband stochastic electrical vestibular stimulation (swsEVS) waveform to the user through the first electrode. The swsEVS waveform used for an initial treatment session of the plurality of treatment sessions may be a predetermined swsEVS waveform that is independent of the user.

The swsEVS may be applied at a peak current level of between 50 μA and 750 μA and in some cases the swsEVS may be applied at a peak current level of 350 μA. A persistent restoration of vestibular function in the user is produced by the plurality of treatment sessions. The persistent restoration of vestibular function includes one or more of regeneration of vestibular hair cells, an increase in gain of synapses between the vestibular hair cells and vestibular nerve fibers, an increase in conductivity/excitability of afferent vestibular nerve fibers, removal of otoconia from semicircular canals, an increase in central neural integration and processing of vestibular, visual and/or proprioceptive signals, an increase in central neural generation of motor control signals, or an increase in efferent feedback from the user's central nervous system to their vestibular inner ear. The persistent restoration of vestibular function in the user may continue to be at least partially in effect for at least 7 days after a final treatment session of the plurality of treatment sessions.

In some cases, each step of the flowchart 6200 is carried out by a clinician. In other cases, the diagnostic screen 6201 and therapeutic screen 6202 (if used) are carried out by a clinician, who then prescribes at-home use of the NEURVESTA device, and the patient then performs the therapy 6203 at home until the prescribed number of treatments are completed 6205. In some cases, the steps of the flowchart 6200 are automated by the NEURVESTA platform system, as shown in FIG. 33, allowing the patient to obtain the NEURVESTA device from a clinical provider or a pharmacy and carry out each step shown in the flowchart 6200 at home. In some situations, the NEURVESTA device may be worn continuously by the patient to provide continuous assessment and adaptive correction of vestibular balance impairments, similar to the manner in which a hearing aid is worn continuously to provide continuous assessment and adaptive correction of hearing impairments.

More detail is now provided by flowchart 6210 in FIG. 62A about the therapeutic screening 6202 and how that may be accomplished. Several different aspects of the EVS signal may be tuned by the therapeutic screening 6202, including finding a motion activation level 6208, finding a perceptual threshold level 6220, and determining stimulation parameters 6209 of the EVS waveform.

The perceptual threshold level is a maximum current level which is at or below a threshold where the patient perceives any sensation from the application of the EVS waveform. As has already been described above, this can be accomplished by applying 6221 a test stimulation waveform to the user at a test current level through the electrodes affixed at or near the user's mastoid starting at an initial test current level, such as about 50 μA or 100 μA. The user is asked if they can detect any sensation from the signal 6223. If the user cannot detect any sensation, the test current level of the test stimulation waveform is increased 6227 and continued to be applied 6221 until the user indicates that a sensation is perceived 6223 at or near the mastoid of the user. The increase may be accomplished in an analog fashion, or with small, discrete steps, such as 50 μA steps. The current level at which the user indicates that the sensation is perceived may be determined to be a perceptual threshold level 6225. Then when the swsEVS waveform is applied to the user during a treatment session, the treatment current level may remain lower than the perceptual threshold level during the treatment session. Depending on the treatment plan, the current treatment level may be in a range of 25% to 75% of the perceptual threshold level.

Flowchart 6230 in FIG. 62B provides more detail on how the motion activation level is set 6208. The motion activation level may be found in the same test as finding the perceptual threshold level or may be done as a separate test. A sensor is then used to determine if any motion is being induced in the user 6232. Depending on the recruitment threshold chosen, an electrical sensor on the user's neck 6233 may be used to detect neck muscle activation via the vestibulocollic reflex (VCR, i.e., vestibulocervical reflex), an electrical sensor on the user's calf or leg 6234 may be used to measure leg muscle activation via the vestibulospinal reflex (VSR) or a force plate 6235 may be used to detect a change in center of gravity due to body motion via the vestibulospinal reflex (VSR). A PHYRATA sensor 6236 may be used to detect head motion for VCR in some cases, or to detect body motion for VSR in other cases. Some VST therapy protocols may use a sensor on an eyelid to detect eye motion via the vestibulo-ocular reflex (VOR). If no motion is detected 6232, the text current level is increased 6237 and applied to the user 6231 until motion is detected. The current level at which motion is detected may be determined to be the motion activation level 6238. Then when the swsEVS waveform is applied to the user during a treatment session, the treatment current level may remain higher than the motion activation level during the treatment session.

The motion activation level and/or the perceptual threshold level may be reestablished at any time during the course of treatment. This may occur by repeating a therapeutic screen 6202 or by performing one or more specific tests to determine the motion activation level and/or the perceptual threshold level.

Flowchart 6250 in FIG. 62C provides more detail on how the spectral content of the swsEVS signal is determined 6209. A test stimulation waveform is applied to the user 6253 and PHYBRATA data from the PHYBRATA sensor is collected and processed 6255. Any type of processing of the PHYBRATA data may be performed, including, but not limited to, generating spatial domain acceleration data, time domain acceleration data, time domain power data, frequency domain data, time-resolved frequency domain data, or sensory reweighting data. The spectral content of the swsEVS waveform 6257 may then be changed based on the PHYBRATA data. Alternatively, or additionally, the current level 6259 of the swsEVS may be changed based on the PHYBRATA data.

Thus, in some implementations, the therapeutic screen 6202 may include affixing a PHYBRATA sensor to a head of the user, applying a test stimulation waveform to the user while monitoring an output of the PHYBRATA sensor, and determining spectral content of the swsEVS waveform based, at least in part, on the output of the PHYBRATA sensor. This may be done before an initial treatment session. The spectral content of the swsEVS waveform may be determined using one or more of spatial domain acceleration data, time domain acceleration data, time domain power data, frequency domain data, time-resolved frequency domain data, or sensory reweighting data of the output of the PHYBRATA sensor. In at least one implementation, normalized power spectral densities (PSDs) are calculated for one or more frequency bands of the output of the PHYBRATA sensor, where the frequency bands may include one or more of a first frequency band consisting of frequencies between 0 Hz and 0.1 Hz, a second frequency band consisting of frequencies between 0.1 Hz and 0.5 Hz, a third frequency band consisting of frequencies between 0.5 Hz and 1 Hz, a fourth frequency band consisting of frequences between 1 Hz and 10 Hz, and a fifth frequency band consisting of frequencies greater than 10 Hz. In some cases, 4 or 5 of the aforementioned frequency bands are used. The spectral content of the swsEVS waveform may then be determined based on the normalized PSDs, such as, but not limited to determining of the spectral content of the swsEVS by adjusting an amplitude of one or more frequency bands of the swsEVS waveform.

The spectral content of the test stimulation waveform may be adjusted during the therapeutic screen 6202, such as increasing the relative amplitude of spectral content of the test stimulation waveform for one or more frequency bands with respect to other frequency bands. The output of the PHYBRATA sensor may then be analyzed to determine how to adjust the spectral content of the swsEVS waveform. In one non-limiting example, a frequency band related to vestibular function, such as a VST band that influences sensory reweighting within at least a portion of the 0.1 to 0.5 Hz PHYBRATA signal range, may be increased with respect to a frequency band related to proprioceptive function, such as a VST band that influences sensory reweighting within at least a portion of the 1.0 to 10.0 Hz PHYBRATA signal range, may be increased and if this reduces the overall power output of the PHYBRATA sensor, or increases the ratio of the vestibular contribution to the proprioceptive contribution, the relative amplitude of the corresponding VST frequency band influencing vestibular function may be increased in the swsEVS waveform used for at least one treatment sessions.

In some cases, the feedback to the changes in swsEVS stimulation parameters may be a real-time loop so that changes in the PHYBRATA data may be used to change the swsEVS waveform in real-time. Thus, the method of providing restoration of vestibular function of a user may include affixing a PHYBRATA sensor to a head of the user and monitoring an output of the PYBRATA sensor during the application of the swsEVS waveform of a treatment session. A current level or spectral content may be modified, at least in part, based on the output of the PHYBRATA sensor during the treatment session. This may be done during any treatment session during the therapy.

Examples of various embodiments are described in the following paragraphs:

Example 1. A method of providing restoration of vestibular function of a user, the method comprising: providing a plurality of treatment sessions to the user, each treatment session in the plurality of treatment sessions comprising affixing a first electrode on or near a mastoid of the user, and applying a subthreshold wideband stochastic electrical vestibular stimulation (swsEVS) waveform to the user through the first electrode as an application of an electrical stimulation; wherein a persistent restoration of vestibular function in the user is produced by the plurality of treatment sessions, the persistent restoration of vestibular function comprising one or more of: regeneration of vestibular hair cells, increased gain of synapses between the vestibular hair cells and vestibular nerve fibers, increased conductivity/excitability of afferent vestibular nerve fibers, removal of otoconia from semicircular canals, increased central neural integration and processing of vestibular, visual and/or proprioceptive signals, increased central neural generation of motor control signals, or increased efferent feedback from a central nervous system of the user to their vestibular inner ear.

Example 2. The method of example 1, wherein the plurality of treatment sessions consists of between 1 and 36 treatment sessions provided over a period of 12 weeks or less.

Example 3. The method of example 1 or 2, where each treatment session of the plurality of treatment sessions are respectively delivered on multiple consecutive days.

Example 4. The method of any of examples 1-3, wherein each treatment session in the plurality of treatment sessions comprises the application of the electrical stimulation to the user through the first electrode for between 10 and 30 minutes.

Example 5. The method of any of examples 1-4, wherein each treatment session in the plurality of treatment sessions comprises the application of the electrical stimulation to the user through the first electrode for between 2 and 60 minutes and consecutive treatment sessions in the plurality of treatment sessions are separated by at least 60 minutes.

Example 6. The method of any of examples 1-5, wherein the plurality of treatment sessions consists of 15 to 20 treatment sessions provided over a period of 4 to 6 weeks and each treatment session in the plurality of treatment sessions comprises the application of the electrical stimulation to the user through the first electrode for between 15 and 25 minutes.

Example 7. The method of any of examples 1-6, wherein the swsEVS waveform is applied at a current level that is low enough to not induce detectable bodily motion by the user.

Example 8. The method of any of examples 1-7, wherein the swsEVS waveform is applied at a current level that is imperceptible by the user.

Example 9. The method of any of examples 1-8, wherein the swsEVS waveform is applied at a peak current level of between 50 μA and 750 μA.

Example 10. The method of any of examples 1-9, wherein the swsEVS waveform is applied at a peak current level of 350 μA.

Example 11. The method of any of examples 1-10, wherein the swsEVS waveform has a frequency spectrum consisting essentially of a plurality of different frequencies under 300 Hz.

Example 12. The method of any of examples 1-10, wherein the swsEVS waveform has a frequency spectrum consisting essentially of a plurality of different frequencies uniformly distributed across a range from 0 Hz to 600 Hz.

Example 13. The method of any of examples 1-12, wherein the swsEVS waveform used for an initial treatment session of the plurality of treatment sessions is a predetermined swsEVS waveform that is independent of the user.

Example 14. The method of any of examples 1-13, wherein the swsEVS waveform comprises a stochastic frequency spectrum.

Example 15. The method of any of examples 1-14, wherein the swsEVS waveform comprises white noise.

Example 16. The method of any of examples 1-14, wherein the swsEVS waveform comprises a colored noise.

Example 17. The method of any of examples 1-16, wherein each treatment session in the plurality of treatment sessions further comprises: affixing the first electrode on or near a right mastoid of the user; affixing a second electrode on or near a left mastoid of the user; affixing a third electrode and a fourth electrode onto the user; applying a first swsEVS waveform to the user through the first electrode and third electrode; and applying a second swsEVS waveform to the user through the second electrode and fourth electrode.

Example 18. The method of example 17, wherein the first swsEVS waveform is different from the second swsEVS waveform.

Example 19. The method of example 17, wherein the first swsEVS waveform is identical to the second swsEVS waveform.

Example 20. The method of example 19, wherein a first polarity of the first swsEVS waveform at the first electrode is inverted from a second polarity of the second swsEVS waveform at the second electrode.

Example 21. The method of any of examples 1-20, wherein the persistent restoration of vestibular function in the user is at least partially in effect for at least 7 days after a final treatment session of the plurality of treatment sessions.

Example 22. The method of any of examples 1-21, further comprising: applying a test stimulation waveform to the user at a test current level through the first electrode starting at an initial test current level; and increasing the test current level of the test stimulation waveform until the user indicates that a sensation is perceived at or near the mastoid of the user, wherein the test current level at which the user indicates that the sensation is perceived is a perceptual threshold level; wherein the swsEVS waveform is applied to the user through the first electrode at a treatment current level that is lower than the perceptual threshold level during at least one treatment session of the plurality of treatment sessions.

Example 23. The method of example 22, further comprising: affixing a PHYBRATA sensor to a head of the user; and detecting a motion activation level of that test stimulation waveform based on an output of the PHYBRATA sensor as the test current level of the test stimulation waveform is increased; wherein that treatment current level is higher than the motion activation level during the at least one treatment session of the plurality of treatment sessions.

Example 24. The method of any of examples 22-23, further comprising: affixing an electrical sensor to a neck of the user and monitoring the test current level through the first electrode starting at the initial test current level; and detecting a neck muscle activation level of that test stimulation waveform based on an output of the electrical sensor as the test current level of the test stimulation waveform is increased; wherein that treatment current level is higher than the neck muscle activation level during the at least one treatment session of the plurality of treatment sessions.

Example 25. The method of any of examples 22-24, further comprising: affixing an electrical sensor to a leg of the user and monitoring the test current level through the first electrode starting at the initial test current level; and detecting a leg muscle activation level of that test stimulation waveform based on an output of the electrical sensor as the test current level of the test stimulation waveform is increased; wherein that treatment current level is higher than the leg muscle activation level during the at least one treatment session of the plurality of treatment sessions.

Example 26. The method of example 25, wherein that treatment current level is between the leg muscle activation level and the perceptual threshold level during each treatment session of the plurality of treatment sessions.

Example 27. The method of example 25 or 26, wherein the perceptual threshold level and the leg muscle activation level are determined before any treatment sessions of the plurality of treatment sessions and the at least one treatment session is an initial treatment session of the plurality of treatment sessions.

Example 28. The method of example 22, further comprising: affixing a second electrical sensor to a neck of the user and monitoring the test current level through the first electrode starting at the initial test current level; and detecting a neck muscle activation level of that test stimulation waveform based on an output of the second electrical sensor as the test current level of the test stimulation waveform is increased; wherein that treatment current level is higher than the neck muscle activation level during the at least one treatment session of the plurality of treatment sessions.

Example 29. The method of example 28, wherein that treatment current level is between the neck muscle activation level and the perceptual threshold level during each treatment session of the plurality of treatment sessions.

Example 30. The method of any of examples 28-29, wherein the perceptual threshold level and the neck muscle activation level are determined before any treatment sessions of the plurality of treatment sessions and the at least one treatment session is an initial treatment session of the plurality of treatment sessions.

Example 31. The method of any of examples 22-30, further comprising: reapplying the test stimulation waveform to the user at the test current level through the first electrode starting at the initial test current level after an initial treatment session of the plurality of treatment sessions has been completed; and increasing the test current level of the test stimulation waveform until the user indicates that a second sensation is perceived, wherein the test current level at which the user indicates that the second sensation is perceived is a second perceptual threshold level; wherein the swsEVS waveform is applied to the user through the first electrode at a second treatment current level that is lower than the second perceptual threshold level during a second treatment session of the plurality of treatment sessions after the initial treatment session.

Example 32. The method of any of examples 22-31, wherein initial test current level is no greater than 100 μA and the test current level is increased in steps of 50 μA.

Example 33. The method of any of examples 22-32, wherein the treatment current level that is in a range of 25% to 75% of the perceptual threshold level.

Example 34. The method of any of examples 1-33, further comprising: affixing a PHYBRATA sensor to a head of the user; applying a test stimulation waveform to the user at a test current level through the first electrode starting at an initial test current level; increasing the test current level of the test stimulation waveform while monitoring an output of the PHYBRATA sensor; and determining a treatment current level based, at least in part, on the output of the PHYBRATA sensor; wherein the swsEVS waveform is applied to the user through the first electrode at the treatment current level during at least one treatment session of the plurality of treatment sessions.

Example 35. The method of example 34, further comprising determining spectral content of the swsEVS waveform based, at least in part, on the output of the PHYBRATA sensor.

Example 36. The method of any of examples 22-34, further comprising: affixing a PHYBRATA sensor to a head of the user; applying a test stimulation waveform to the user while monitoring an output of the PHYBRATA sensor; and determining spectral content of the swsEVS waveform based, at least in part, on the output of the PHYBRATA sensor.

Example 37. The method of example 36, wherein the spectral content of the swsEVS waveform based, at least in part, on the output of the PHYBRATA sensor is determined before an initial treatment session of the plurality of treatment sessions.

Example 38. The method of example 36 or 37, wherein one or more of spatial domain acceleration data, time domain acceleration data, time domain power data, frequency domain data, time-resolved frequency domain data, or sensory reweighting data of the output of the PHYBRATA sensor is used for determining the spectral content of the swsEVS waveform.

Example 39. The method of any of examples 36-38, further comprising: calculating normalized power spectral densities (PSDs) for at least one frequency bands of the output of the PHYBRATA sensor, the at least one frequency bands selected a first frequency band consisting of frequencies between 0 Hz and 0.1 Hz, a second frequency band consisting of frequencies between 0.1 Hz and 0.5 Hz, a third frequency band consisting of frequencies between 0.5 Hz and 1 Hz, a fourth frequency band consisting of frequences between 1 Hz and 10 Hz, or a fifth frequency band consisting of frequencies greater than 10 Hz; and using the normalized PSDs to determine spectral content of the swsEVS waveform.

Example 40. The method of any of examples 36-39, wherein the determining of the spectral content of the swsEVS waveform comprises adjusting an amplitude of one or more frequency bands of the swsEVS waveform.

Example 41. The method of any of examples 1-40, further comprising: affixing a PHYBRATA sensor to a head of the user; monitoring an output of the PHYBRATA sensor during the application of the swsEVS waveform of a treatment session of the plurality of treatment sessions; and modifying spectral content of the swsEVS waveform and/or peak current level applied through the first electrode based, at least in part, on the output of the PHYBRATA sensor.

Example 42. The method of any of examples 1-41, wherein the spectral content of the swsEVS waveform and/or the peak current level is modified during the treatment session.

Example 43. The method of any of examples 1-42, wherein the spectral content of the swsEVS waveform and/or the peak current level is modified for a subsequent treatment session of the plurality of treatment sessions.

Example 44. The method of any of examples 41-43, wherein one or more of spatial domain acceleration data, time domain acceleration data, time domain power data, frequency domain data, time-resolved frequency domain data, or sensory reweighting data of the output of the PHYBRATA sensor is used for determining the spectral content of the swsEVS waveform and/or the peak current level.

Example 45. The method of any of examples 41-44, wherein the modifying of the spectral content of the swsEVS waveform comprises adjusting an amplitude of one or more frequency bands of the swsEVS waveform.

Example 46. The method of any of examples 1-45, further comprising: affixing a PHYBRATA sensor to a head of the user; monitoring an output of the PHYBRATA sensor during the application of the swsEVS waveform of a treatment session of the plurality of treatment sessions; and modifying a current level through the first electrode based, at least in part, on the output of the PHYBRATA sensor.

Example 47. The method of any of examples 1-46, wherein the current level through the first electrode is modified during the treatment session.

Example 48. The method of any of examples 1-47, wherein the current level through the first electrode is modified for a subsequent treatment session of the plurality of treatment sessions.

Example 49. The method of any of examples 1-48, further comprising: performing an evaluation of balance of the user before the plurality of treatment sessions; and creating the swsEVS waveform based on the evaluation of the balance of the user; the evaluation of the balance of the user comprising: affixing a PHYBRATA sensor to a head of the user; collecting first data from the PHYBRATA sensor from the user while standing with eyes of the user open; collecting second data from the PHYBRATA sensor from the user while standing with the eyes of the user closed; and analyzing the first data and the second data to determine spectral content for the swsEVS waveform.

Example 50. The method of example 49, the evaluation of the balance of the user further comprising: collecting third data from the PHYBRATA sensor from the user while standing with the eyes of the user open with feet of the user spread apart, wherein the first data is collected with the feet of the user close together; collecting fourth data from the PHYBRATA sensor from the user while standing with the eyes of the user closed with the feet of the user spread apart, wherein the second data is collected with the feet of the user close together; and analyzing the first data, the second data, the third data, and the fourth data to determine spectral content for the swsEVS waveform.

Example 51. The method of example 49 or 50, the evaluation of the balance of the user further comprising: collecting third data from the PHYBRATA sensor from the user while standing on a foam pad with the eyes of the user open, wherein the first data is collected while the user is standing on a solid surface; collecting fourth data from the PHYBRATA sensor from the user while standing on the foam pad with the eyes of the user closed, wherein the second data is collected while the user is standing on the solid surface; and analyzing the first data, the second data, the third data, and the fourth data to determine spectral content for the swsEVS waveform.

Unless otherwise indicated, all numbers expressing quantities, properties, measurements, and so forth, used in the specification and claims are to be understood as being modified in all instances by the term "about." The recitation of numerical ranges by endpoints includes all numbers subsumed within that range, including the endpoints (e.g. 1 to 5 includes 1, 2.78, π, $3.\overline{33}$, 4, and 5).

As used in this specification and the appended claims, the singular forms "a", "an", and "the" include plural referents unless the content clearly dictates otherwise. Furthermore, as used in this specification and the appended claims, the term "or" is generally employed in its sense including "and/or" unless the content clearly dictates otherwise. As used herein, the term "coupled" includes direct and indirect connections. Moreover, where first and second devices are coupled, intervening devices including active devices may be located there between.

The description of the various embodiments provided above is illustrative in nature and is not intended to limit this disclosure, its application, or uses. Thus, different variations beyond those described herein are intended to be within the scope of embodiments. Such variations are not to be regarded as a departure from the intended scope of this disclosure. As such, the breadth and scope of the present disclosure should not be limited by the above-described exemplary embodiments but should be defined only in accordance with the following claims and equivalents thereof.

We claim as follows:

1. A method of providing restoration of vestibular function of a user, the method comprising:

affixing a test electrode on or near a mastoid of the user;

applying a test stimulation waveform to the user at a test current level through the test electrode starting at an initial test current level;

increasing the test current level of the test stimulation waveform until the user indicates that a sensation is perceived at or near the mastoid of the user, wherein the test current level at which the user indicates that the sensation is perceived is a perceptual threshold level; and providing a plurality of treatment sessions to the user, each treatment session in the plurality of treatment sessions comprising affixing a first electrode on or near a mastoid of the user, and applying a subthreshold wideband stochastic electrical vestibular stimulation (swsEVS) waveform to the user through the first electrode as an application of an electrical stimulation, wherein the swsEVS waveform is applied to the user at a treatment current level that is lower than the perceptual threshold level during at least one treatment session of the plurality of treatment sessions;

wherein a persistent restoration of vestibular function in the user is produced by the plurality of treatment sessions, the persistent restoration of vestibular function comprising one or more of:

increased conductivity/excitability of afferent vestibular nerve fibers, increased central neural integration and processing of vestibular, visual and/or proprioceptive signals, or increased central neural generation of motor control signals.

2. The method of claim 1, wherein each treatment session in the plurality of treatment sessions comprises the application of the electrical stimulation to the user through the first electrode for between 2 and 60 minutes and consecutive treatment sessions in the plurality of treatment sessions are separated by at least 60 minutes.

3. The method of claim 1, wherein the swsEVS waveform is applied at a current level that is low enough to not induce detectable bodily motion by the user.

4. The method of claim 1, wherein the swsEVS waveform is applied at a current level that is imperceptible by the user.

5. The method of claim 1, wherein the swsEVS waveform has a frequency spectrum consisting essentially of a plurality of different frequencies under 300 Hz.

6. The method of claim 1, wherein the swsEVS waveform used for an initial treatment session of the plurality of treatment sessions is a predetermined swsEVS waveform that is independent of the user.

7. The method of claim 1, wherein each treatment session in the plurality of treatment sessions further comprises:

affixing the first electrode on or near a right mastoid of the user;

affixing a second electrode on or near a left mastoid of the user;

affixing a third electrode and a fourth electrode onto the user;

applying a first swsEVS waveform to the user through the first electrode and third electrode; and applying a second swsEVS waveform to the user through the second electrode and fourth electrode.

8. The method of claim 7, wherein the first swsEVS waveform is different from the second swsEVS waveform.

9. The method of claim 1, wherein the persistent restoration of vestibular function in the user is at least partially in effect for at least 7 days after a final treatment session of the plurality of treatment sessions.

10. The method of claim 1, further comprising:

affixing a physiological vibration acceleration (PHYBRATA) sensor to a head of the user; and detecting a motion activation level of that test stimulation waveform based on an output of the PHYBRATA sensor as the test current level of the test stimulation waveform is increased;

wherein that treatment current level is higher than the motion activation level during the at least one treatment session of the plurality of treatment sessions.

11. The method of claim 1, further comprising:

affixing an electrical sensor to a neck of the user and monitoring the test current level through the test electrode starting at the initial test current level; and detecting a neck muscle activation level of that test stimulation waveform based on an output of the electrical sensor as the test current level of the test stimulation waveform is increased;

wherein that treatment current level is higher than the neck muscle activation level during the at least one treatment session of the plurality of treatment sessions.

12. The method of claim 1, further comprising:

affixing an electrical sensor to a leg of the user and monitoring the test current level through the test electrode starting at the initial test current level; and detecting a leg muscle activation level of that test stimulation waveform based on an output of the electrical sensor as the test current level of the test stimulation waveform is increased;

wherein that treatment current level is higher than the leg muscle activation level during the at least one treatment session of the plurality of treatment sessions.

13. The method of claim 12, wherein that treatment current level is between the leg muscle activation level and the perceptual threshold level during each treatment session of the plurality of treatment sessions.

14. The method of claim 12, wherein the perceptual threshold level and the leg muscle activation level are determined before any treatment sessions of the plurality of treatment sessions and the at least one treatment session is an initial treatment session of the plurality of treatment sessions.

15. The method of claim 12, further comprising:

affixing a second electrical sensor to a neck of the user and monitoring the test current level through the test electrode starting at the initial test current level; and detecting a neck muscle activation level of that test stimulation waveform based on an output of the second electrical sensor as the test current level of the test stimulation waveform is increased;

wherein that treatment current level is higher than the neck muscle activation level during the at least one treatment session of the plurality of treatment sessions.

16. The method of claim 15, wherein that treatment current level is between the neck muscle activation level and the perceptual threshold level during each treatment session of the plurality of treatment sessions.

17. The method of claim 15, wherein the perceptual threshold level and the neck muscle activation level are determined before any treatment sessions of the plurality of treatment sessions and the at least one treatment session is an initial treatment session of the plurality of treatment sessions.

18. The method of claim 1, further comprising:

affixing a new test electrode on or near a mastoid of the user after an initial treatment session of the plurality of treatment sessions has been completed;

reapplying the test stimulation waveform to the user at the test current level through the new test electrode starting at the initial test current level; and increasing the test current level of the test stimulation waveform until the user indicates that a second sensation is perceived, wherein the test current level at which the user indicates that the second sensation is perceived is a second perceptual threshold level;

wherein the swsEVS waveform is applied to the user through the first electrode at a second treatment current level that is lower than the second perceptual threshold level during a second treatment session of the plurality of treatment sessions after the initial treatment session.

19. The method of claim 1, wherein initial test current level is no greater than 100 μA and the test current level is increased in steps of 50 μA.

20. The method of claim 1, wherein the treatment current level that is in a range of 25% to 75% of the perceptual threshold level.

21. The method of claim 1, further comprising:

affixing a PHYBRATA sensor to a head of the user;

applying a test stimulation waveform to the user at a test current level through the first electrode starting at an initial test current level;

increasing the test current level of the test stimulation waveform while monitoring an output of the PHYBRATA sensor; and determining a treatment current level based, at least in part, on the output of the PHYBRATA sensor;

wherein the swsEVS waveform is applied to the user through the first electrode at the treatment current level during at least one treatment session of the plurality of treatment sessions.

22. The method of claim 21, further comprising determining spectral content of the swsEVS waveform based, at least in part, on the output of the PHYBRATA sensor.

23. The method of claim 1, further comprising:
affixing a PHYBRATA sensor to a head of the user;
applying a test stimulation waveform to the user while monitoring an output of the PHYBRATA sensor; and
determining spectral content of the swsEVS waveform based, at least in part, on the output of the PHYBRATA sensor.

24. The method of claim 23, wherein the spectral content of the swsEVS waveform based, at least in part, on the output of the PHYBRATA sensor is determined before an initial treatment session of the plurality of treatment sessions.

25. The method of claim 23, wherein one or more of spatial domain acceleration data, time domain acceleration data, time domain power data, frequency domain data, time-resolved frequency domain data, or sensory reweighting data of the output of the PHYBRATA sensor is used for determining the spectral content of the swsEVS waveform.

26. The method of claim 23, wherein the determining of the spectral content of the swsEVS waveform comprises adjusting an amplitude of one or more frequency bands of the swsEVS waveform.

27. The method of claim 1, further comprising:
affixing a PHYBRATA sensor to a head of the user;
monitoring an output of the PHYBRATA sensor during the application of the swsEVS waveform of a treatment session of the plurality of treatment sessions; and
modifying spectral content of the swsEVS waveform and/or peak current level applied through the first electrode based, at least in part, on the output of the PHYBRATA sensor.

28. The method of claim 27, wherein the spectral content of the swsEVS waveform and/or the peak current level is modified for a subsequent treatment session of the plurality of treatment sessions.

29. The method of claim 27, wherein one or more of spatial domain acceleration data, time domain acceleration data, time domain power data, frequency domain data, time-resolved frequency domain data, or sensory reweighting data of the output of the PHYBRATA sensor is used for determining the spectral content of the swsEVS waveform and/or the peak current level.

30. The method of claim 27, wherein the modifying of the spectral content of the swsEVS waveform comprises adjusting an amplitude of one or more frequency bands of the swsEVS waveform.

31. The method of claim 1, further comprising:
affixing a PHYBRATA sensor to a head of the user;
monitoring an output of the PHYBRATA sensor during the application of the swsEVS waveform of a treatment session of the plurality of treatment sessions; and
modifying a current level through the first electrode based, at least in part, on the output of the PHYBRATA sensor.

32. The method of claim 31, wherein the current level through the first electrode is modified for a subsequent treatment session of the plurality of treatment sessions.

33. The method of claim 1, the persistent restoration of vestibular function comprising increased conductivity/excitability of afferent vestibular nerve fibers.

34. The method of claim 1, the persistent restoration of vestibular function comprising increased central neural integration and processing of vestibular, visual and/or proprioceptive signals.

35. The method of claim 1, the persistent restoration of vestibular function comprising increased central neural generation of motor control signals.

36. A method of providing restoration of vestibular function of a user, the method comprising:
providing a plurality of treatment sessions to the user, each treatment session in the plurality of treatment sessions comprising affixing a first electrode on or near a mastoid of the user, and applying a subthreshold wideband stochastic electrical vestibular stimulation (swsEVS) waveform to the user through the first electrode as an application of an electrical stimulation;
wherein a persistent restoration of vestibular function in the user is produced by the plurality of treatment sessions, the persistent restoration of vestibular function comprising one or more of:
increased conductivity/excitability of afferent vestibular nerve fibers,
increased central neural integration and processing of vestibular, visual and/or proprioceptive signals, or
increased central neural generation of motor control signals
the method further comprising:
affixing a PHYBRATA sensor to a head of the user;
applying a test stimulation waveform to the user while monitoring an output of the PHYBRATA sensor;
determining spectral content of the swsEVS waveform based, at least in part, on the output of the PHYBRATA sensor;
calculating normalized power spectral densities (PSDs) for at least one frequency bands of the output of the PHYBRATA sensor, the at least one frequency bands selected a first frequency band consisting of frequencies between 0 Hz and 0.1 Hz, a second frequency band consisting of frequencies between 0.1 Hz and 0.5 Hz, a third frequency band consisting of frequencies between 0.5 Hz and 1 Hz, a fourth frequency band consisting of frequences between 1 Hz and 10 Hz, or a fifth frequency band consisting of frequencies greater than 10 Hz; and
using the normalized PSDs to determine spectral content of the swsEVS waveform.

37. A method of providing restoration of vestibular function of a user, the method comprising:
performing an evaluation of balance of the user comprising: affixing a PHYBRATA sensor to a head of the user; collecting first data from the PHYBRATA sensor from the user while the user is standing with eyes of the user open; collecting second data from the PHYBRATA sensor from the user while the user is standing with the eyes of the user closed; and analyzing the first data and the second data to determine spectral content for the a subthreshold wideband stochastic electrical vestibular stimulation (swsEVS) waveform;
creating the swsEVS waveform based on the evaluation of the balance of the user and including the spectral content; and
providing a plurality of treatment sessions to the user, each treatment session in the plurality of treatment sessions comprising affixing a first electrode on or near a mastoid of the user, and applying the swsEVS waveform to the user through the first electrode as an application of an electrical stimulation;
wherein a persistent restoration of vestibular function in the user is produced by the plurality of treatment sessions, the persistent restoration of vestibular function comprising one or more of:

increased conductivity/excitability of afferent vestibular nerve fibers, increased central neural integration and processing of vestibular, visual and/or proprioceptive signals, or increased central neural generation of motor control signals.

38. A method of providing restoration of vestibular function of a user, the method comprising:

affixing a test electrode on or near a mastoid of the user;

applying a test stimulation waveform to the user at a test current level through the test electrode starting at an initial test current level;

increasing the test current level of the test stimulation waveform until the user indicates that a sensation is perceived at or near the mastoid of the user, wherein the test current level at which the user indicates that the sensation is perceived is a perceptual threshold level; and providing a plurality of treatment sessions to the user, each treatment session in the plurality of treatment sessions comprising affixing a first electrode on or near a mastoid of the user, and applying a subthreshold wideband stochastic electrical vestibular stimulation (swsEVS) waveform to the user through the first electrode as an application of an electrical stimulation, wherein the swsEVS waveform is applied to the user at a treatment current level that is lower than the perceptual threshold level during at least one treatment session of the plurality of treatment sessions;

wherein a persistent restoration of vestibular function in the user is produced by the plurality of treatment sessions, the persistent restoration of vestibular function comprising one or more of:

regeneration of vestibular hair cells, increased gain of synapses between the vestibular hair cells and vestibular nerve fibers, removal of otoconia from semicircular canals, or increased efferent feedback from a central nervous system of the user to their vestibular inner ear.

39. The method of claim 38, wherein the swsEVS waveform has a frequency spectrum consisting essentially of a plurality of different frequencies uniformly distributed across a range from 0 Hz to 600 Hz.

40. The method of claim 38, wherein the swsEVS waveform comprises white noise.

41. The method of claim 38, wherein the swsEVS waveform comprises a colored noise.

42. The method of claim 38, further comprising:

affixing a PHYBRATA sensor to a head of the user;

monitoring an output of the PHYBRATA sensor during the application of the swsEVS waveform of a treatment session of the plurality of treatment sessions; and modifying spectral content of the swsEVS waveform and/or peak current level applied through the first electrode based, at least in part, on the output of the PHYBRATA sensor;

wherein the spectral content of the swsEVS waveform and/or the peak current level is modified during the treatment session.

43. The method of claim 38, further comprising:

affixing a PHYBRATA sensor to a head of the user;

monitoring an output of the PHYBRATA sensor during the application of the swsEVS waveform of a treatment session of the plurality of treatment sessions; and modifying a current level through the first electrode based, at least in part, on the output of the PHYBRATA sensor;

wherein the current level through the first electrode is modified during the treatment session.

44. The method of claim 38, further comprising:

performing an evaluation of balance of the user before the plurality of treatment sessions; and creating the swsEVS waveform based on the evaluation of the balance of the user;

the evaluation of the balance of the user comprising:

affixing a PHYBRATA sensor to a head of the user;

collecting first data from the PHYBRATA sensor from the user while standing with eyes of the user open;

collecting second data from the PHYBRATA sensor from the user while standing with the eyes of the user closed;

analyzing the first data and the second data to determine spectral content for the swsEVS waveform;

collecting third data from the PHYBRATA sensor from the user while standing with the eyes of the user open with feet of the user spread apart, wherein the first data is collected with the feet of the user close together;

collecting fourth data from the PHYBRATA sensor from the user while standing with the eyes of the user closed with the feet of the user spread apart, wherein the second data is collected with the feet of the user close together; and analyzing the first data, the second data, the third data, and the fourth data to determine spectral content for the swsEVS waveform.

45. The method of claim 38, further comprising:

performing an evaluation of balance of the user before the plurality of treatment sessions; and creating the swsEVS waveform based on the evaluation of the balance of the user;

the evaluation of the balance of the user comprising:

affixing a PHYBRATA sensor to a head of the user;

collecting first data from the PHYBRATA sensor from the user while standing with eyes of the user open;

collecting second data from the PHYBRATA sensor from the user while standing with the eyes of the user closed;

analyzing the first data and the second data to determine spectral content for the swsEVS waveform;

collecting third data from the PHYBRATA sensor from the user while standing on a foam pad with the eyes of the user open, wherein the first data is collected while the user is standing on a solid surface;

collecting fourth data from the PHYBRATA sensor from the user while standing on the foam pad with the eyes of the user closed, wherein the second data is collected while the user is standing on the solid surface; and analyzing the first data, the second data, the third data, and the fourth data to determine spectral content for the swsEVS waveform.

46. The method of claim 38, the persistent restoration of vestibular function comprising regeneration of vestibular hair cells.

47. The method of claim 38, the persistent restoration of vestibular function comprising increased gain of synapses between the vestibular hair cells and vestibular nerve fibers.

48. The method of claim 38, the persistent restoration of vestibular function comprising removal of otoconia from semicircular canals.

49. The method of claim 38, the persistent restoration of vestibular function comprising increased efferent feedback from a central nervous system of the user to their vestibular inner ear.

50. The method of claim 38, wherein the persistent restoration of vestibular function in the user is at least partially in effect for at least 7 days after a final treatment session of the plurality of treatment sessions.

* * * * *